US012409006B2

(12) United States Patent
Asadian et al.

(10) Patent No.: US 12,409,006 B2
(45) Date of Patent: *Sep. 9, 2025

(54) JOINT CALIBRATION FOR SURGICAL TOOL

(71) Applicant: Verb Surgical Inc., Santa Clara, CA (US)

(72) Inventors: Ali Asadian, San Jose, CA (US); Alireza Hariri, Berkeley, CA (US); Andrew Dahdouh, Campbell, CA (US)

(73) Assignee: Verb Surgical Inc., Santa Clara, CA (US)

( * ) Notice: Subject to any disclaimer, the term of this patent is extended or adjusted under 35 U.S.C. 154(b) by 196 days.

This patent is subject to a terminal disclaimer.

(21) Appl. No.: 18/081,055

(22) Filed: Dec. 14, 2022

(65) Prior Publication Data

US 2023/0117447 A1  Apr. 20, 2023

Related U.S. Application Data

(63) Continuation of application No. 16/814,422, filed on Mar. 10, 2020, now Pat. No. 11,547,511.

(Continued)

(51) Int. Cl.
*A61B 34/30* (2016.01)
*A61B 34/00* (2016.01)
(Continued)

(52) U.S. Cl.
CPC .............. *A61B 34/74* (2016.02); *A61B 34/25* (2016.02); *A61B 34/35* (2016.02); *A61B 34/37* (2016.02);
(Continued)

(58) Field of Classification Search
CPC ......... A61B 34/00; A61B 34/30; A61B 34/37; A61B 34/74; A61B 34/25; A61B 34/71; A61B 90/00
See application file for complete search history.

(56) References Cited

U.S. PATENT DOCUMENTS

| 5,947,996 A | 9/1999 | Logeman |
| 10,166,082 B1 | 1/2019 | Hariri |

(Continued)

FOREIGN PATENT DOCUMENTS

| CN | 101941192 A | 1/2011 |
| CN | 103481251 A | 1/2014 |

(Continued)

OTHER PUBLICATIONS

Chinese Office Action for Chinese App. No. 202080057750.6 mailed Apr. 7, 2024, with translation.

(Continued)

*Primary Examiner* — Vi X Nguyen
(74) *Attorney, Agent, or Firm* — Lempia Summerfield Katz LLC

(57) ABSTRACT

The disclosed embodiments relate to systems and methods for a surgical tool or a surgical robotic system. An end effector of the surgical tool is coupled to a tool driver. An actuator is driven by a motor of the tool driver and configured to drive a degree of freedom of the end effector. One or more processors are configured to receive a position command describing a desired position for the end effector, translate the desired position to a command for a joint associated with the end effector, calculate a compensation term to compensate for a source of hysteresis for backlash and/or compliance, and send a motor command for the motor coupled with the actuator based on the compensation term and the command for the end effector.

9 Claims, 25 Drawing Sheets

Related U.S. Application Data

(60) Provisional application No. 62/887,386, filed on Aug. 15, 2019.

(51) Int. Cl.
  *A61B 34/35* (2016.01)
  *A61B 34/37* (2016.01)
  *A61B 90/00* (2016.01)
  *B25J 9/12* (2006.01)
  *G16H 40/63* (2018.01)
  *A61B 17/00* (2006.01)

(52) U.S. Cl.
  CPC .............. *A61B 34/71* (2016.02); *A61B 34/77* (2016.02); *A61B 90/03* (2016.02); *A61B 90/06* (2016.02); *A61B 90/08* (2016.02); *B25J 9/12* (2013.01); *G16H 40/63* (2018.01); *A61B 2017/00398* (2013.01); *A61B 2017/00477* (2013.01); *A61B 2034/301* (2016.02); *A61B 2034/305* (2016.02); *A61B 2034/742* (2016.02); *A61B 2090/031* (2016.02); *A61B 2090/035* (2016.02); *A61B 2090/066* (2016.02); *A61B 2090/0807* (2016.02); *A61B 2090/0809* (2016.02); *A61B 2090/0811* (2016.02)

(56) References Cited

U.S. PATENT DOCUMENTS

| | | | |
|---|---|---|---|
| 10,595,836 | B2 | 3/2020 | Smaby et al. |
| 10,888,370 | B2 | 1/2021 | Shelton, IV et al. |
| 11,278,362 | B2 | 3/2022 | Shelton, IV et al. |
| 11,547,511 | B2 * | 1/2023 | Asadian ................ A61B 34/37 |
| 2007/0013336 | A1 | 1/2007 | Nowlin |
| 2009/0248038 | A1 | 10/2009 | Blumenkranz et al. |
| 2010/0234857 | A1 * | 9/2010 | Itkowitz ............... G09B 23/285 |
| | | | 700/259 |
| 2015/0157411 | A1 | 6/2015 | Choi |
| 2017/0087715 | A1 | 3/2017 | Komuro et al. |
| 2017/0172549 | A1 | 6/2017 | Smaby |
| 2017/0189130 | A1 | 7/2017 | Weir |
| 2018/0079090 | A1 | 3/2018 | Koenig |
| 2018/0085178 | A1 | 3/2018 | Komuro |
| 2018/0116741 | A1 | 5/2018 | Garcia Kilroy |
| 2018/0168762 | A1 | 6/2018 | Scheib et al. |
| 2018/0168763 | A1 | 6/2018 | Scheib et al. |
| 2018/0207798 | A1 | 7/2018 | Tsuzaki |
| 2018/0228561 | A1 | 8/2018 | Shelton, IV et al. |
| 2019/0029678 | A1 | 1/2019 | Shelton, IV |
| 2019/0053801 | A1 | 2/2019 | Wixey et al. |
| 2020/0029945 | A1 * | 1/2020 | Brisson .................. A61B 34/35 |
| 2020/0054401 | A1 | 2/2020 | Yu |
| 2020/0315721 | A1 | 10/2020 | Rabindran et al. |
| 2021/0052340 | A1 | 2/2021 | Rabindran et al. |
| 2025/0099194 | A1 | 3/2025 | Overmyer et al. |

FOREIGN PATENT DOCUMENTS

| | | |
|---|---|---|
| CN | 107847235 A | 3/2018 |
| CN | 109689305 A | 4/2019 |
| KR | 20180083306 A | 7/2018 |
| WO | 2007111737 A2 | 10/2007 |
| WO | 2016201313 A1 | 12/2016 |
| WO | 2020040796 A1 | 2/2020 |

OTHER PUBLICATIONS

International Search Report and the Written Opinion for International Patent Application PCT/US2020/045598mailed Dec. 2, 2020.
European Search Report for European Application No. 20852625.1-1113 mailed Aug. 11, 2023.

* cited by examiner

JOINT CALIBRATION FOR SURGICAL TOOL

CROSS REFERENCE TO PRIOR APPLICATION

This application is a continuation under 37 C.F.R. § 1.53(b) and 35 U.S.C. § 120 of U.S. patent application Ser. No. 16/814,422, filed Mar. 10, 2020, which claims priority benefit of Provisional Application No. 62/887,386 filed Aug. 15, 2019, each of which is hereby incorporated by reference in its entirety.

FIELD

This disclosure relates to engagement, calibration, and/or additional control of a surgical robotic tool with one or more actuators.

BACKGROUND

Surgical robotic systems give an operator or user, such as an operating surgeon, the ability to perform one or more actions of a surgical procedure. In the surgical robotic system, a surgical tool or instrument, such as an endoscope, clamps, cutting tools, spreaders, needles, energy emitters, etc., is mechanically coupled to a robot joint of a surgical robotic arm, so that movement or actuation of the robot joint directly causes a rotation, pivoting, or linear movement of a part of the tool. Once the tool is attached to (e.g., in contact with) a tool drive in the arm, operator commands may cause movements and activate functions of the attached tool.

Due to the varied nature of surgical procedures, different surgical tools or instruments may be selectively attached to the same arm of a surgical robotic system before and during a surgical procedure. In order to avoid equipment malfunctions during a surgical procedure, it is important that the surgical tool or instrument not only be attached to but also mechanically engaged to the robot joint of the surgical robotic arm. That is, mechanisms in the surgical tool that impart motion or enable the activation of instrument features should be mechanically engaged to the actuators that are in the tool drive of the arm of the surgical robotic system before the surgical tool is in use during the surgical procedure. Challenges arise in performing the engagement, for example, in relation to detection of engagement or synchronization of engagement, and arise in subsequent operation of the surgical tool related to recoil and safety procedures.

SUMMARY

Disclosed herein is a robotically-assisted surgical electromechanical system designed for surgeons to perform minimally-invasive surgery. A suite of compatible tools can be attached/detached from an instrument driver mounted to the distal end of a robotic arm, enabling the surgeon to perform various surgical tasks. The instrument drivers can provide intracorporeal access to the surgical site, mechanical actuation of compatible tools through a sterile interface, and communication with compatible tools through a sterile interface and user touchpoints.

Unlimited range of motion is a desired clinical feature for the rotary axis of a surgical instrument. However, lack of mechanical hardstops in such a design makes engagement of the tool driver to the instrument challenging. A method or apparatus to engage the driving motor of the rotary actuator to the instrument's roll tool disk while the instrument has no hardstop to constrain its motion and can freely move is described. An example method may include detecting an attachment of the surgical tool to a tool driver, such that the roll tool disk of the surgical tool is engageable with a drive disk of the tool driver, driving the drive disk through the rotary motor, and determining whether a measured torque of the rotary motor exceeds a preset torque threshold for a preset period of time since the actuation.

A method or apparatus to synchronize two motors during engagement and homing of a coupling mechanism is described. Using two or more coupled motors, the end effector load is divided between the two or more motors that are constrained through the coupling mechanism. The method or apparatus includes a two-stage method to safely synchronize motors in this coupled system and engage and home the coupling mechanism against its hard stop. An example method may include sending a low torque command to the first motor coupled to the closure joint of the surgical tool and to the second motor coupled to the closure joint of the surgical tool, determining whether the first motor and the second motor meet one or more hold engagement criteria, sending a high torque command to the first motor and the second motor in response to the first motor and the second motor meeting the one or more hold engagement criteria.

A method or apparatus to calibrate and control a constrained mechanism with backlash and/or compliance is also described. In a surgical instrument, the mechanical design of the end effector, as well as properties of the drive train may exhibit backlash and/or compliance. A method or apparatus is configured to control for backlash and/or compliance and achieve acceptable position tracking performance. An example method may include receiving a position command describing a desired position for an end effector of the surgical tool or an actuator to drive the end effector of the surgical tool, translating the desired position to a command associated with the actuator, calculating a backlash compensation term to compensate for a source of backlash, and sending a motor command for the actuator based on the backlash compensation term and the command for the end effector.

Finally, a method or apparatus to provide safety enhancements is described. Towards this goal, an algorithm may actively adjust actuator motion to account for interaction between the instrument and its environment. An example method includes receiving an initial joint command for the joint of the surgical tool, determining a joint torque based on motor torque of a motor for the joint of the surgical tool, calculating a tip force based on an effective geometry (e.g., length) associated with the joint and based on the joint torque, comparing the tip force to a predetermined threshold, calculating an admittance control compensation term in response to the comparison of the estimated tip force and the predetermined threshold, and generating a command for the motor based on the admittance control compensation term and the initial joint command.

DETAILED DESCRIPTION

Surgical Robotic System

Figure 1:
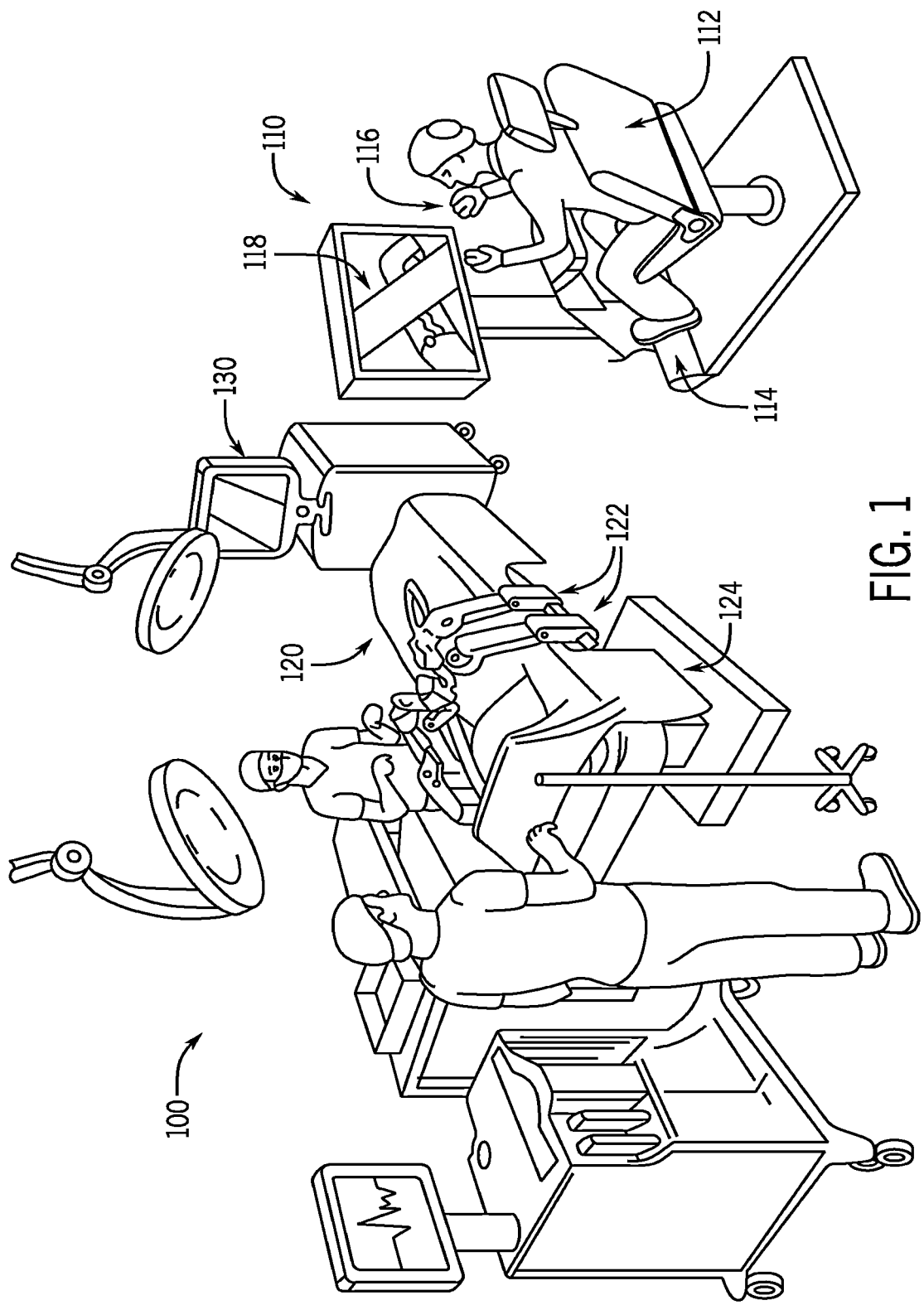
FIG. 1 depicts an example operating room environment including a surgical robotic system.

FIG. 1 is a diagram illustrating an example operating room environment with a surgical robotic system 100. As shown in FIG. 1, the surgical robotic system 100 comprises a user console 110, a control tower 130, and a surgical robot 120 having one or more surgical robotic arms 122 mounted on a surgical platform 124 (e.g., a table or a bed etc.), where surgical tools with end effectors are attached to the distal ends of the robotic arms 122 for executing a surgical procedure. The robotic arms 122 are shown as table-mounted, but in other configurations, the robotic arms may be mounted in a cart, a ceiling, a sidewall, or other suitable support surfaces.

Generally, a user, such as a surgeon or other operator, may be seated at the user console 110 to remotely manipulate the robotic arms 122 and/or surgical instruments (e.g., teleoperation). The user console 110 may be located in the same operation room as the robotic system 100, as shown in FIG. 1. In other environments, the user console 110 may be located in an adjacent or nearby room, or teleoperated from a remote location in a different building, city, or country. The user console 110 may comprise a seat 112, pedals 114, one or more handheld user interface devices (UIDs) 116, and an open display 118 configured to display, for example, a view of the surgical site inside a patient. As shown in the exemplary user console 110, a surgeon sitting in the seat 112 and viewing the open display 118 may manipulate the pedals 114 and/or handheld user interface devices 116 to remotely control robotic arms 122 and/or surgical instruments mounted to the distal ends of the arms 122.

In some variations, a user may also operate the surgical robotic system 100 in an "over the bed" (OTB) mode, in which the user is at the patient's side and simultaneously manipulating a robotically-driven tool/end effector attached thereto (e.g., with a handheld user interface device 116 held in one hand) and a manual laparoscopic tool. For example, the user's left hand may be manipulating a handheld user interface device 116 to control a robotic surgical component, while the user's right hand may be manipulating a manual laparoscopic tool. Thus, in these variations, the user may perform both robotic-assisted minimally invasive surgery (MIS) and manual laparoscopic surgery on a patient.

An end effector may be configured to execute a surgical operation such as cutting, grasping, poking, or energy emission. The surgical tool may be manipulated manually, robotically, or both, during the surgery. For example, the surgical tool may be a tool used to enter, view, or manipulate an internal anatomy of the patient. In an embodiment, the surgical tool is a grasper that can grasp tissue of the patient. The surgical tool may be controlled manually, directly by a hand of a bedside operator or it may be controlled robotically, via sending electronic commands to actuate movement.

During an exemplary procedure or surgery, the patient is prepped and draped in a sterile fashion to achieve anesthesia. Initial access to the surgical site may be performed manually with the robotic system 100 in a stowed configuration or withdrawn configuration to facilitate access to the surgical site. Once the access is completed, initial positioning and/or preparation of the robotic system may be performed. During the procedure, a surgeon in the user console 110 may utilize the pedals 114 and/or user interface devices 116 to manipulate various end effectors and/or imaging systems to perform the surgery. Manual assistance may also be provided at the procedure table by sterile-gowned personnel, who may perform tasks including but not limited to, retracting tissues or performing manual repositioning or tool exchange involving one or more robotic arms 122. Nonsterile personnel may also be present to assist the surgeon at the user console 110. When the procedure or surgery is completed, the robotic system 100 and/or user console 110 may be configured or set in a state to facilitate one or more post-operative procedures, including but not limited to, robotic system 100 cleaning and/or sterilization, and/or healthcare record entry or printout, whether electronic or hard copy, such as via the user console 110.

In some aspects, the communication between the surgical robot 120 and the user console 110 may be through the control tower 130, which may translate user input from the user console 110 to robotic control commands and transmit the control commands to the surgical robot 120. The control tower 130 may also transmit status and feedback from the robot 120 back to the user console 110. The connections between the surgical robot 120, the user console 110 and the control tower 130 may be via wired and/or wireless connections, and may be proprietary and/or performed using any of a variety of data communication protocols. Any wired connections may be optionally built into the floor and/or walls or ceiling of the operating room. The surgical robotic system 100 may provide video output to one or more displays, including displays within the operating room, as well as remote displays accessible via the Internet or other networks. The video output or feed may also be encrypted to ensure privacy and all or portions of the video output may be saved to a server or electronic healthcare record system.

Prior to initiating surgery with the surgical robotic system, the surgical team can perform the preoperative setup. During the preoperative setup, the main components of the surgical robotic system (table 124 and robotic arms 122, control tower 130, and user console 110) are positioned in the operating room, connected, and powered on. The surgical platform 124 and robotic arms 122 may be in a fully-stowed configuration with the arms 122 under the surgical platform 124 for storage and/or transportation purposes. The surgical team can extend the arms from their stowed position for sterile draping.

After draping, the arms 122 can be partially retracted until needed for use. A number of conventional laparoscopic steps may be performed including trocar placement and installation. For example, each sleeve can be inserted with the aid of an obturator, into a small incision and through the body wall. The sleeve and obturator allow optical entry for visualization of tissue layers during insertion to minimize risk of injury during placement. The endoscope is typically placed first to provide hand-held camera visualization for placement of other trocars.

After insufflation, if required, manual instruments can be inserted through the sleeve to perform any laparoscopic steps by hand. Next, the surgical team may position the robotic arms 122 over the patient and attach each arm 122 to its corresponding sleeve. The surgical robotic system 100 has the capability to uniquely identify each tool (endoscope and surgical instruments) as soon as it is attached and display the tool type and arm location on the open or immersive display 118 at the user console 110 and the touchscreen display on the control tower 130. The corresponding tool functions are enabled and can be activated using the master UIDs 116 and foot pedals 114. The patient-side assistant can attach and detach the tools, as required, throughout the procedure. The surgeon seated at the user console 110 can begin to perform surgery using the tools controlled by two master UIDs 116 and foot pedals 114. The system translates the surgeon's hand, wrist, and finger movements through the master UIDs 116 into precise real-time movements of the surgical tools. Therefore, the system constantly monitors every surgical maneuver of the surgeon and pauses instrument movement if the system is unable to precisely mirror the surgeon's hand motions. In case the endoscope is moved from one arm to another during surgery, the system can adjust the master UIDs 116 for instrument alignment and continue instrument control and motion. The foot pedals 114 may be used to activate various system modes, such as endoscope control and various instrument functions including monopolar and bipolar cautery, without involving surgeon's hands removed from the master UIDs 116.

The surgical platform 124 can be repositioned intraoperatively. For safety reasons, all tooltips should be in view and under active control by the surgeon at the user console 110. Instruments that are not under active surgeon control are removed, and the table feet are locked. During table motion, the integrated robotic arms 122 may passively follow the table movements. Audio and visual cues can be used to guide the surgery team during table motion. Audio cues may include tones and voice prompts. Visual messaging on the displays at the user console 110 and control tower 130 can inform the surgical team of the table motion status.

Figure 2:
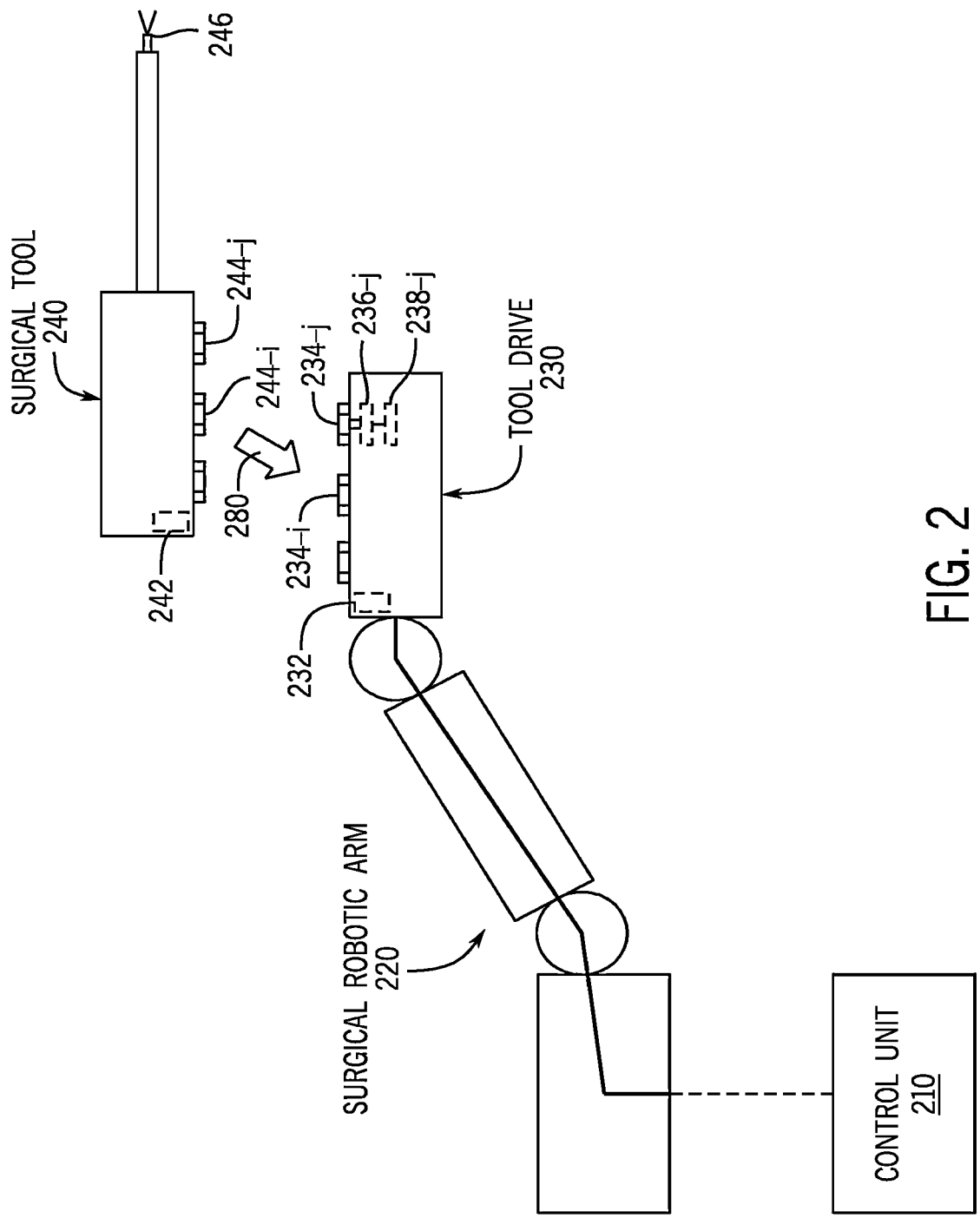
FIG. 2 depicts an example of the surgical tool and associated tool drive.

FIG. 2 is an illustration of a subsystem or a part of the surgical robotic system 100, for detecting engagement of a surgical tool 240 to a tool driver 230 (tool driver) of a surgical robotic arm 220. The surgical robotic arm 220 may be one of the surgical robotic arms 220 of surgical robotic system 100 illustrated and discussed with respect to FIG. 1. The control unit 210 may be part of for example the control tower in FIG. 1. As discussed in more detail herein, the engagement may be detected by control unit 210 based on one or more rotary motor operating parameters of one or more actuators (e.g., actuator 238-$j$) in the tool driver 230.

There is a tool driver 230 to which different surgical tools (e.g., surgical tool 240, as well as other detachable surgical tools for rotation of an endoscope camera, pivoting of a grasper jaw, or translation of a needle) may be selectively attached (one at a time.) This may be done by for example a human user holding the housing of the surgical tool 240 in her hand and moving the latter in the direction of arrow 280 shown until the outside surface of the surgical tool 240 in which there are one or more tool disks (e.g., tool disk 244-$i$) comes into contact with the outside surface of the tool driver 230 in which there are one or more drive disks (e.g., drive disk 234-$j$). The one or more tool disks and/or one or more drive disks may be implements by pucks, which may be formed of plastic or another durable material. In the example shown, the tool driver 230 is a segment of the surgical robotic arm 220 at a distal end portion of the surgical robotic arm 220. A proximal end portion of the arm 220 is secured to a surgical robotic platform, such as a surgical table that shown in FIG. 1 described above.

Control unit 210 is responsible for controlling motion of the various motorized joints in the surgical robotic arm 220 (including the drive disks 234) through which operation of end effector 246 (its position and orientation as well as its surgical function such as opening, closing, cutting, applying pressure, etc.) which mimics that of a user input device is achieved. This is achieved via a mechanical transmission in the surgical tool 240, when the surgical tool 240 has been engaged to transfer force or torque from the tool driver 230. The control unit 210 may be implemented as a programmed processor, for example as part of the control tower 130 of FIG. 1. It may respond to one or more user commands received via a local or remote user input (e.g., joystick, touch control, wearable device, or other user input device communicating via console computer system.) Alternatively, the control unit 210 may respond to one or more autonomous commands or controls (e.g., received form a trained surgical machine learning model that is being executed by the control unit 210 or by the console computer system), or a combination thereof. The commands dictate the movement of robotic arm 220 and operation of its attached end effector 246.

An end effector 246 may be any surgical instruments, such as jaws, a cutting tool, an endoscope, spreader, implant tool, etc. Different surgical tools each having different end effectors can be selectively attached (one at a time) to robotic arm 220 for use during a surgical or other medical procedure. The end effector 246 depicted in the example of FIG. 2 is jaws located at a distal end of the surgical tool 240 and that may be retracted into, or extend out of, a cannula as shown (e.g., a thin tube that may be inserted into a patient undergoing a surgical procedure).

The robotic arm 220 includes a tool driver 230, in which there are one or more actuators, such as actuator 238-$j$. Each actuator may be a linear or rotary actuator that has one or more respective electric motors (e.g., a brushless permanent magnet motor) whose drive shaft may be coupled to a respective drive disk 234-$j$ through a transmission (e.g., a gear train that achieves a given gear reduction ratio). The tool driver 230 includes one or more drive disks 234 that may be arranged on a planar or flat surface of the tool driver 230, wherein the figure shows several such drive disks that are arranged on the same plane of the flat surface. Each drive disk (e.g., drive disk 234-*j*) is exposed on the outside surface of the tool driver 230 and is designed to mechanically engage (e.g., to securely fasten via snap, friction, or other mating features) a mating tool disk 244-*j* of the surgical tool 240, to enable direct torque transfer between the two. This may take place once for example a planar or flat surface of the surgical tool 240 and corresponding or mating planar or flat surface of the tool driver 230 are brought in contact with one another.

Furthermore, a motor driver circuit (for example, installed in the tool driver 230 or elsewhere in the surgical robotic arm 220) is electrically coupled to the input drive terminals of a constituent motor of one or more of the actuators 238. The motor driver circuit manipulates the electrical power drawn by the motor in order to regulate for example the speed of the motor or its torque, in accordance with a motor driver circuit input, which can be set or controlled by control unit 210, which results in the powered rotation of the associated drive disk (e.g., drive disk 234-*j*).

When the mating drive disk 234-*j* is mechanically engaged to a respective tool disk 244-*j*, the powered rotation of the drive disk 234-*j* causes the tool disk 244-*j* to rotate, e.g., the two disks may rotate as one, thereby imparting motion on, for example, linkages, gears, cables, chains, or other transmission devices within the surgical tool 240 for controlling the movement and operation of the end effector 246 which may be mechanically coupled to the transmission device.

Different surgical tools may have different numbers of tool disks based on the types of movements and the number of degrees of freedom in which the movements are performed by their end effectors, such as rotation, articulation, opening, closing, extension, retraction, applying pressure, etc.

Furthermore, within the surgical tool 240, more than one tool disk 244 may contribute to a single motion of the end effector 246 to achieve goals such as load sharing by two or more motors that are driving the mating drive disks 234, respectively. In another aspect, within the tool driver 230, there may be two or more motors whose drive shafts are coupled (via a transmission) to rotate the same output shaft (or drive disk 234), to share a load.

In yet another aspect, within the surgical tool 240, there may be a transmission which translates torque from two drive disks 234 (via respective tool disks 244) for performing complementary actions in the same degree of freedom, e.g., a first drive disk 234-*j* rotates a drum within the housing of the surgical instrument 240 to take in one end of a rod, and a second drive disk 234-*i* rotates another drum within the housing of the surgical instrument 240 to take in the other end of the rod. As another example, the extension and the shortening of an end effector along a single axis may be achieved using two tool disks 234-*i*, 234-*j*, one to perform the extension and another to perform the retraction. This is in contrast to an effector that also moves in one degree of freedom (e.g., extension and shortening longitudinally along a single axis of movement) but that only needs a single tool disk to control its full range of movement. As another example, an effector that moves in multiple degrees of freedom (e.g., such as a wristed movement, movement along multiple axes, activation of an energy emitter in addition to end effector movement, etc.) may necessitate the use of several tool disks (each being engaged to a respective drive disk). In another type of surgical tool 240, a single tool disk 244 is sufficient to perform both extension and retraction motions, via direct input (e.g., gears). As another example, in the case of the end effector 246 being jaws, two or more tool disks 244 may cooperatively control the motion of the jaws, for load sharing, as discussed in greater detail herein.

In some embodiments, when surgical tool 240 is first attached to or installed on tool driver 230 such that the tool disks are brought substantially into coplanar and coaxial alignment with corresponding drive disks (though the tool and drive disks are perhaps not yet successfully engaged), control unit 210 initially detects the type of the surgical tool 240. In one embodiment, surgical tool 240 has an information storage unit 242, such as a solid state memory, radio frequency identification (RFID) tag, bar code (including two-dimensional or matrix barcodes), etc., that identifies its tool or end effector information, such as one or more of identification of tool or end effector type, unique tool or end effector ID, number of tool disks used, location of those tool disks being used (e.g., from a total of six possible tool disks 244-*e, f, g, h, i, j*), type of transmission for the tool disks (e.g., direct drive, cable driven, etc.), what motion or actuation a tool disk imparts on the end effector, one or more tool calibration values (e.g., a rotational position of the tool disk as determined during factor testing/assembly of the tool), whether motion of the end effector is constrained by a maximum or minimum movement, as well as other tool attributes. In one embodiment, the information storage unit 242 identifies minimal information, such as a tool ID, which control unit 210 may use to perform a lookup of the various tool attributes.

The tool driver 230 may include a communication interface 232 (e.g., a memory writer, a near field communications, near field communication (NFC), transceiver, RFID scanner, barcode reader, etc.) to read the information from the information storage unit 242 and pass the information to control unit 210. Furthermore, in some embodiments, there may be more than one information storage unit in surgical tool 240, such as one information storage unit associated with each tool disk 244. In this embodiment, tool driver 230 may also include a corresponding sensor for each possible information storage unit that would be present in a given tool.

After surgical tool 240 is attached with tool driver 230, such that tool disks are brought into alignment and are superimposed on corresponding drive disks (although not necessarily mechanically engaged), and after the tool disk information is obtained, e.g., read by control unit 210, the control unit 210 performs an engagement process to detect when all of the tool disks that are expected to be attached to respective drive disks are mechanically engaged with their respective drive disks (e.g., their mechanical engagement has been achieved, or the tool driver 230 is now deemed engaged with the tool). That is, attaching the surgical tool 240 with the tool driver 230 does not necessarily ensure the proper mating needed for mechanical engagement of tool disks with corresponding drive disks (e.g., due to misalignment of mating features). The engagement process may include activating one or more motors of an actuator (e.g., actuator 238-*j*) that drives a corresponding drive disk 234-*j*. Then, based on one or more monitored motor operating parameters of the actuator 238-*j*, while the latter is driving the drive disk 234-*j*, the mechanical engagement of the tool disk 244-*i* with a drive disk 234-*j* can be detected, as discussed in greater detail below. This process may be repeated for every drive disk 234 (of the tool driver 230) that is expected to be currently attached to a respective tool disk 244 (e.g., as determined based on the tool disk information obtained for the particular surgical tool 240 that is currently attached.)

Upon detecting that a particular type of surgical tool 240 has been attached with the tool driver 230, the control unit 210 activates one or more actuators (e.g., motors) of the tool driver 230 that have been previously associated with that type of surgical tool 240. In some embodiments, each actuator that is associated with a corresponding drive disk 234 of surgical tool 240 may be activated simultaneously, serially, or a combination of simultaneous and serial activation.

As an alternative to the system of FIG. 2, in one variation, the tool driver 230 may include an elongated base (or "stage") having longitudinal tracks and a tool carriage, which is slidingly engaged with the longitudinal tracks. The stage may be configured to couple to the distal end of a robotic arm such that articulation of the robotic arm positions and/or orients the tool driver 230 in space. Additionally, the tool carriage may be configured to receive the base of the tool, which may also include a tool shaft extending from the tool base and through the cannula, with robotic wrist and the end effector 246 disposed at the distal end.

Figure 3:
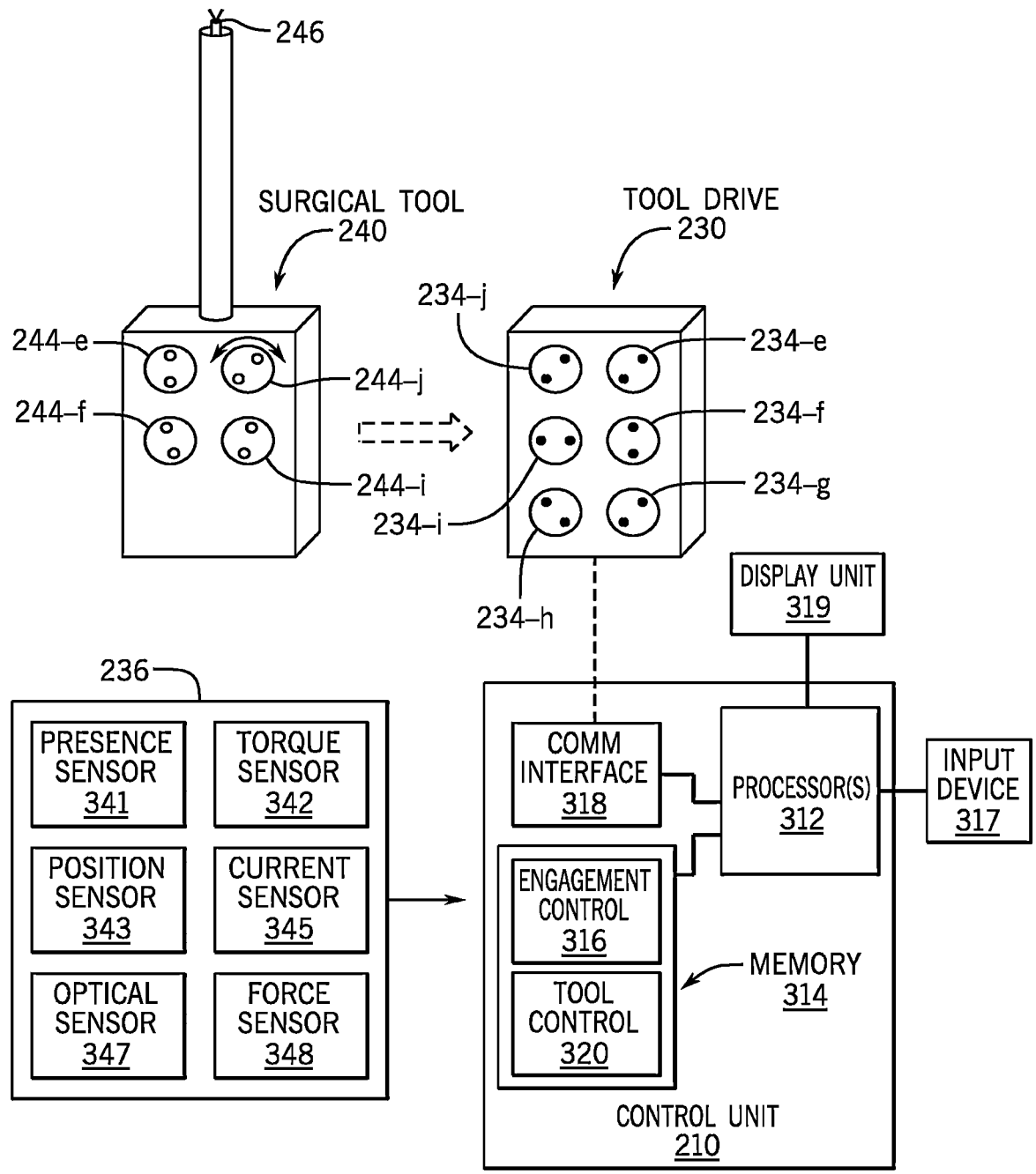
FIG. 3 illustrates an example control system for the surgical tool and associated tool drive of FIG. 2.

FIG. 3 illustrates an example of the surgical tool 240 that utilizes four tool disks, such as tool disks 244-e, f, i, j, arranged in a coplanar fashion on a mating surface of its housing. Each tool disk contributes to at least a portion of the movement and/or activation of end effector 246. Upon detecting the attachment of surgical tool 240 with tool driver 230 (e.g., joining of mating surfaces of the respective housings), control unit 210 (or its processor 312 while executing instructions stored in memory 314 as engagement control 316) performs a process which determines that only the corresponding four drive disks, such as drive disk 234-e, g, i, j, are to be turned (a corresponding actuator 238 is activated—see FIG. 2) to perform the engagement process.

In some embodiments, a physical constraint may be created by the use of coordinating movement of multiple drive disks, and/or by letting a single drive disk engage before engaging a second drive disk. For example, consider the case where two or more tool disks (in the same housing of a surgical tool 240) are connected by a transmission in the housing of the tool 240 to share a load (end effector 246) when turning in the same direction, such as when a cutting or clamping tool may need to apply force beyond that which a single actuator 238-j could supply. In such an embodiment, two or more actuators that are turning in the same direction (their respective drive disks are turning in the same direction) are driving the same output shaft that is inside the surgical tool 240 (due to the transmission in the surgical tool 240 that is connected to the corresponding tool disks.) Now, if the two actuators are signaled to move in opposing directions, then as soon as one of the drive disks engages its corresponding tool disk, this becomes a physical constraint to the other drive disk (when the other drive disk has engaged its corresponding tool disk.) When one of the two or more actuators engages (its drive disk engages its corresponding tool disk), the control unit 210 creates a constraint for the other actuator by signaling the engaged actuator to, for example, enter a position hold state. That is, a first actuator 238-j may be commanded by the control unit 210 to hold its position while the other, non-engaged actuator 238-i continues to be signaled to drive and thus turn or move (toward engagement between its drive disk 234-i and tool disk 244-i.) In this embodiment, one or both of the actuators' motor operating parameters can be monitored to detect engagement between a tool disk and drive disk pair.

Furthermore, if a hardstop (hard stop) does exist (the control unit 210 may be programmed for or access a configuration to determine that this particular tool 240 has a hardstop), then the actuator of an engaged drive disk can be signaled to continue to drive or turn in the same direction until the hardstop is detected. The other actuator may continue to turn in the opposing direction and attempt to engage while the already engaged actuator holds its position at the hardstop.

Returning to FIG. 2, during operation of actuator 238-j, after the detected attachment of surgical tool 240 with tool driver 230, one or more sensors 236-j measure one or more motor operating parameters of the actuator 238-j as its motor is signaled to start to move.

In one embodiment, the selected actuator 238 is signaled to turn so as to cause its attached tool disk 244 to rotate so that the end effector 246 that is connected to the tool disk 244 moves towards a physical constraint (e.g. a jaw opens until it stops against a cannula wall, a maximum in a range of motion is achieved when bumping against a hardstop in a fully open position, etc.) In yet another embodiment, such as an endoscope embodiment where two actuators are sharing the load being rotation of an endoscope camera where there may be no hardstops against rotation of the camera, the selected actuator 238 rotates its attached tool disk 244-i in a direction that opposes the motion of another tool disk 244-j that is also rotatably coupled to the same output shaft in the transmission housing of the tool 240. In that instance, as soon as one of the tool disks 244-i, 244-j engages, it acts as a physical constraint to the other tool disk. Other predetermined directions of movement may also be used consistent with the discussion herein.

Furthermore, in some embodiments, the actuator's movement is ramped or increased gradually by the control unit 210 (e.g., the control unit 210 signals or commands the actuator 238 to start to rotate at a slow speed at the beginning of movement and then progressively increase the speed, and then progressively decrease the speed at detection of engagement). In one embodiment, the calibration values stored in the information storage unit 242 of the surgical tool 240 may be used to expedite tool engagement. For example, the calibration values can include a factory determined position (angle) of a particular tool disk 244-j, recorded during product assembly or testing. The engagement process may include a predetermined home position of a corresponding drive disk 234-j, which may be obtained by the control unit 210 performing a tool driver calibration routine, in which it determines when a particular drive disk 234-j has reached a home position (as the control unit actuates the drive disk 234-j), such that position of that drive disk 234-j is now stored at or identified by the control unit 210. Note that the control unit 210 may do so while only relying on output from a position sensor that is in the tool driver 230, and the tool 240 itself may be passive in that it has no electronic sensors in it.

Next, the control unit 210 may activate the corresponding actuator 238 of the drive disk 234-j so that the drive disk 234-j turns at a high speed until a position variable of the drive disk 234-j comes close to the factory determined position. When the drive disk satisfies a threshold distance relative to the factory determined position (e.g., a home position of the tool disk) which implies that mating features of the tool disk and drive disk are near alignment, the speed may be reduced so as to increase the likelihood that the mating features engage one another upon their initial encounter.

In some embodiments, the motor operating parameters monitored by the control unit 210 (via sensors 236) are interpreted to mean successful mechanical engagement of a tool disk with a drive disk. The control unit 210 is in communication with and receives sensor data from sensor 236 in an example sensor array including any combination of a presence sensor 341, a torque sensor 342, a position sensor 343, an electrical sensor 345, an optical sensor 347, and a force sensor 348. The sensor array may include separate sensors for different degrees of freedom of the surgical tool (e.g., closure joint, roll joint, or other operation of the surgical tool). That is, the sensor array, or one or more sensors thereof, may be repeated for multiple tool disks 244 in the tool driver 230.

The measurements may include measurements of torque applied by the actuator 238-*j* as measured by the torque sensor 342 or the force sensor 348, measurements of current by the electrical sensor 345 supplied to a motor of the actuator 238-*j* when attempting to drive the actuator to move at a certain velocity (e.g., where the sensor 236-*j* may include a current sensing resistor in series with a motor input drive terminal), measurements of electrical impedance by the electrical sensor 345 as seen into the input drive terminals of the motor of the actuator 238 when attempting to drive the motor to move at a certain velocity (e.g., where the sensor 236-*j* may also include a voltage sensing circuit to measure voltage of the motor input drive terminal), speed of the actuator 238-*j* (e.g., where the optical sensor 347 may include a position encoder on an output shaft of the actuator 238-*j* or on a drive shaft of the motor), as well as other parameters referred to here as motor operating parameters. The measurements may include presence data from the presence sensor 341, implied from any sensor in the sensory array 236, or determined from the interaction between the information storage unit 242 and the communication interface 232. The position sensor 343 is illustrated separately but may be implemented using a combination of the presence sensor 341, the torque sensor 342, the electrical sensor 345, the optical sensor 347, and the force sensor 348. In one example, additional sensors of the same type may be used for the position sensor 343.

While monitoring the one or more motor operating parameters of a particular actuator, when one or more of these parameters satisfies (e.g., meets or reaches) a predetermined, condition or threshold, the detection of such a situation can be interpreted by control unit 210 as a mechanical engagement event. Note that satisfying the predetermined condition may for example mean that the monitored operating parameter exhibits certain changes, as per the threshold, relative to an operating parameter of another motor that is part of the same actuator 238-*j* or that is part of another actuator 238-*i* which his being controlled by the control unit 210 simultaneously during the engagement detection process.

In some embodiments, detection of certain motor operating parameters during operation of the actuator 238-*j*, such as one or more of i) torque that satisfies (e.g., rises and reaches) a torque threshold, ii) motor current that satisfies (e.g., rises and reaches) a current threshold, iii) impedance that drops below an impedance threshold, iv) motor speed dropping below a motor velocity threshold, or a combination thereof, are used by control unit 210 to determine that mechanical engagement of tool disk 244-*j* to drive disk 234-*j* has occurred. The following are some examples of such a process.

Returning to FIG. 2, and as discussed above, the tool identification performed by control unit 210 enables the latter to identify the characteristics of the end effector 246 of surgical tool 240. For example, the control unit 210 may use that identification process to determine whether two (or more) tool disks in the tool 240 act in concert to impart end effector 246 movement, whether one or more movements of the end effector 246 are subject to hardstops or physical constraints, what are the ranges of movement of the end effector 246, what actuators are used by the tool 240, and factory defined calibration values such as a home position of a tool disk. Note that a calibration value may encompass a range, e.g., 290 degrees+/−4 degrees. Based on such a calibration value, e.g., a home position of the tool disk 244-*i*, and based on the present position of the corresponding drive disk 234-*i* (determined using a position encoder in the tool driver 230), the control unit 210 can track the difference during the engagement process (as the actuator is signaled to turn.) So long as the difference is greater than a predetermined threshold, then the actuator is signaled to turn rapidly (fast rotation), and then in response to the difference becoming smaller than the threshold (implying that the drive disk is nearing the calibration value home position) the actuator is signaled to turn slowly (slow rotation), and that is expected to increase the chances of a reliable engagement being detected.

The control unit 210 including its programmed processor 312 may be integrated into the surgical robotic system 100 (FIG. 1) for example as a shared microprocessor and program memory within the control tower 130. Alternatively, the control unit 210 may be implemented in a remote computer such as in a different room than the operating room, or in a different building than the operating arena shown in FIG. 1. Furthermore, control unit 210 may also include, although not illustrated, user interface hardware (e.g., keyboard, touch-screen, microphones, speakers) that may enable manual control of the robotic arm and its attached surgical tool 240, a power device (e.g., a battery), as well as other components typically associated with electronic devices for controlling surgical robotic systems.

Memory 314 is coupled to one or more processors 312 (generically referred to here as a processor for simplicity) to store instructions for execution by the processor 312. In some embodiments, the memory is non-transitory, and may store one or more program modules, including a tool control 320 and an engagement control 316, whose instructions configure the processor 312 to perform the engagement processes described herein. In other words, the processor 312 may operate under the control of a program, routine, or the execution of instructions stored in the memory 314 as part of the tool control 320 and engagement control 316 to execute methods or processes in accordance with the aspects and features described herein. The memory 314 may include one or more settings, coefficient values, threshold values, tolerance values, calibration values for the surgical tool 240 and/or the tool driver 230. These values may be stored in memory 314 as a configuration file, table, or matrix. Some values in the configuration file may be provided by the user, some may be accessed or retrieved based on identifiers of the surgical tool 240 or tool driver 230, and others may be set by the control unit 210.

In response to detecting the attaching of the surgical tool 240 with the tool driver 230, engagement control 316 performs (or rather configures the processor 312 to perform) a process for detecting the mechanical engagement of tool disks with corresponding drive disks (which are actuator driven), such as engagement of tool disk 244-*i* with corresponding drive disk 234-*i*. The engagement control 316 may signal (through the tool control 320) that one or more of the actuators of tool driver 230 impart motion of their respective drive disks. In some embodiments, these instructions or signals include instructions to energize, activate or otherwise provide power to a motor so that the motor can produce or apply a specific amount of torque, cause the drive disk to rotate at a specific speed and direction, by applying a certain voltage command, current command, etc. Furthermore, the motion of each drive disk can be controlled to start rapidly initially during the engagement detection process, and then ramp down slowly once engagement is near, or proximity to alignment of mating features is detected or a predetermined time limit is reached without detecting engagement. For instance, based on the relative position of a drive disk to a tool disk (which may be based on a known calibration value), the actuator speed is ramped down to a predetermined speed (e.g., until the drive disk is within a threshold distance of where the mating features become aligned.

The engagement control 316 monitors one or more motor operating parameters of the motors of actuators of the tool driver 230. As discussed herein, the motor operating parameters can include torque imparted by a motor, voltage supplied to a motor, impedance as seen on the input drive terminals of a motor when attempting to drive the motor to move at a certain velocity, motor speed, as well as other motor operating parameters. One or more of these parameters may be monitored by comparing them to thresholds, so that when the thresholds are reached then a mechanical engagement event is deemed to have occurred (between, for example, tool disk 244-$i$ and drive disk 234-$i$.) As discussed herein, mechanical engagement is expected to be detected when corresponding mating features of a tool disk and a drive disk align and fasten with one another to that rotation of the drive disk causes for example both immediate and proportional rotation of the mechanically engaged tool disk (as one with the drive disk.) Such engagement is expected to be detected when one or more of the motor operating parameters satisfies a threshold (e.g., reaching or exceeding a threshold indicative of a hardstop being reached, a maximum torque, voltage, or impedance value, a torque, voltage, or impedance value greater than what would be needed to overcome friction that initially appears when the tool 240 is first attached to the tool driver 230. The engagement control 316 thus infers or deduces that tool disk 244-$i$ and drive disk 234-$j$ have engaged with one another (e.g., fastening of respective disk mating features with one another).

Note that engagement control 316 need not monitor sensor readings for all of the motor parameters that are available from the tool driver 230. Instead engagement control 316 could monitor only one or more characteristics of interest based on, for example, whether surgical tool 240 is subject to any hardstops or physical movement constraints, whether one or more tool disks operate in concert (cooperate with each other) to impart movement on surgical tool 240, whether tool disks impart movement on surgical tool 240 directly (e.g., through a gear box) in order to determine when a threshold associated with engagement is satisfied.

In some embodiments, engagement control 316 monitors patterns of motor operating parameters, such as patterns of torque, voltage, motor speed, impedance, etc. that are the result of drive disk 234-$j$ rotating over tool disk 244-$j$ but without mechanical engagement. That is, a certain amount of torque, force, voltage, etc. could be measured, which is greater than what is exhibited by a free moving drive disk (where the surgical tool 240 is not attached to the tool driver 230) and less than a mechanically engaged drive disk (when for example mating features of the tool and drive disks pass each other while the tool and tool drive housings are in contact, but without engaging.) When this motor parameter pattern changes as detected, such as due to a hardstop or physical motion constraint being encountered, engagement control 316 is said to have detected mechanical engagement. Monitoring and interpreting pattern based motor operating pattern also enables engagement control 316 to detect engagement (between tool disk 244-$j$ and drive disk 234-$j$) even when no hardstop or motion constraint is available, or without having to drive a drive disk to a tool's hardstop or other motion constraint.

In some embodiments, when engagement control 316 detects mechanical engagement of tool disks with drive disks, it may also initiate a verification process or engagement check in which the actuators of tool driver 230 are signaled to undergo a predetermined set of one or more motions, to verify the detected engagement. For example, the actuators may be instructed to cause their respective drive disks to rotate in a direction opposite to the direction of engagement (the latter being the direction in which the drive disks were rotating when engagement was initially detected. Then, the drive disks may be rotated back in the direction of engagement until a second engagement is detected (e.g., when a particular motor parameter reaches a threshold that is consistent with the tool disk reaching a hardstop or a motion constraint, when a particular motor parameter reaches a threshold that is consistent with resistance against the rotating tool disk that is not caused by friction alone (friction between the tool disk and a corresponding drive disk), or a combination thereof.

Engagement control 316, based on having detected engagement of tool disks to drive disks, or based on a countdown timer having expired without detecting engagement, generates a notification for an operator of the surgical robotic system. The notification may either indicate that engagement has occurred so that the surgical tool 240 is ready for use, or that engagement has not occurred and so the surgical tool 240 should be reattached.

Roll Joint Engagement without Physical Constraints

As described above some rotary devices, such as tool disk 244 and drive disk 234, have hard stops that facilitate the detection and engagement of the surgical tool 240 to the tool driver 230. In one example, in tool driver 230 at least one degree of freedom (e.g., corresponding to a rotary device) includes a hard stop. However, unlimited range of motion may be a desired clinical feature for at least one rotary axis of a surgical instrument. Unlimited range of motion may be defined as rotation of a rotary device (e.g., tool disk 244 or drive disk 234) through a full rotation of 360°, more than 360° such as up to 720°, or nearly 360° wherein nearly is within 10 degrees. Unlimited range of motion may be achieved through the omission of a hardstop or other physical constraint included in the surgical tool 204 or elsewhere to impede the motion of the tool disk 244 and/or the drive disk 234 at a prescribed maximum range of motion. The physical constraint may be omitted for one tool disk 244 and drive disk 234 pair and in at least one degree of freedom of movement from which motor operating parameters can be measured. One example may be rotation of the end effector 246 around its rotation axis. In addition to the omission of hardstop or other physical constraint, the end effector 246 is driven only by a single motor in the tool driver 230. Thus, limitation of one tool disk 244 and/or drive disk 234 by another tool disk 244 and/or drive disk 234 is not available. Alternatively, two motors may effectively apply a hard stop even when there is no physical constraint.

The lack of mechanical hardstops or other physical constraints may cause engagement of the tool driver 230 to the instrument challenging. Engagement detection methods which rely on simultaneous force and velocity saturation are not effective in this application. At least one of the following embodiments include apparatus and methods to engage the driving motor of the rotary actuator to the instrument's roll disk while the instrument has no hardstop or other physical constraint to constrain its motion and can freely move. An algorithm which takes into account the evolution of a force signal during rotary motion enables engagement of the instrument disk with tool driver and detect this event prior to manipulating the device is described.

Figure 4:
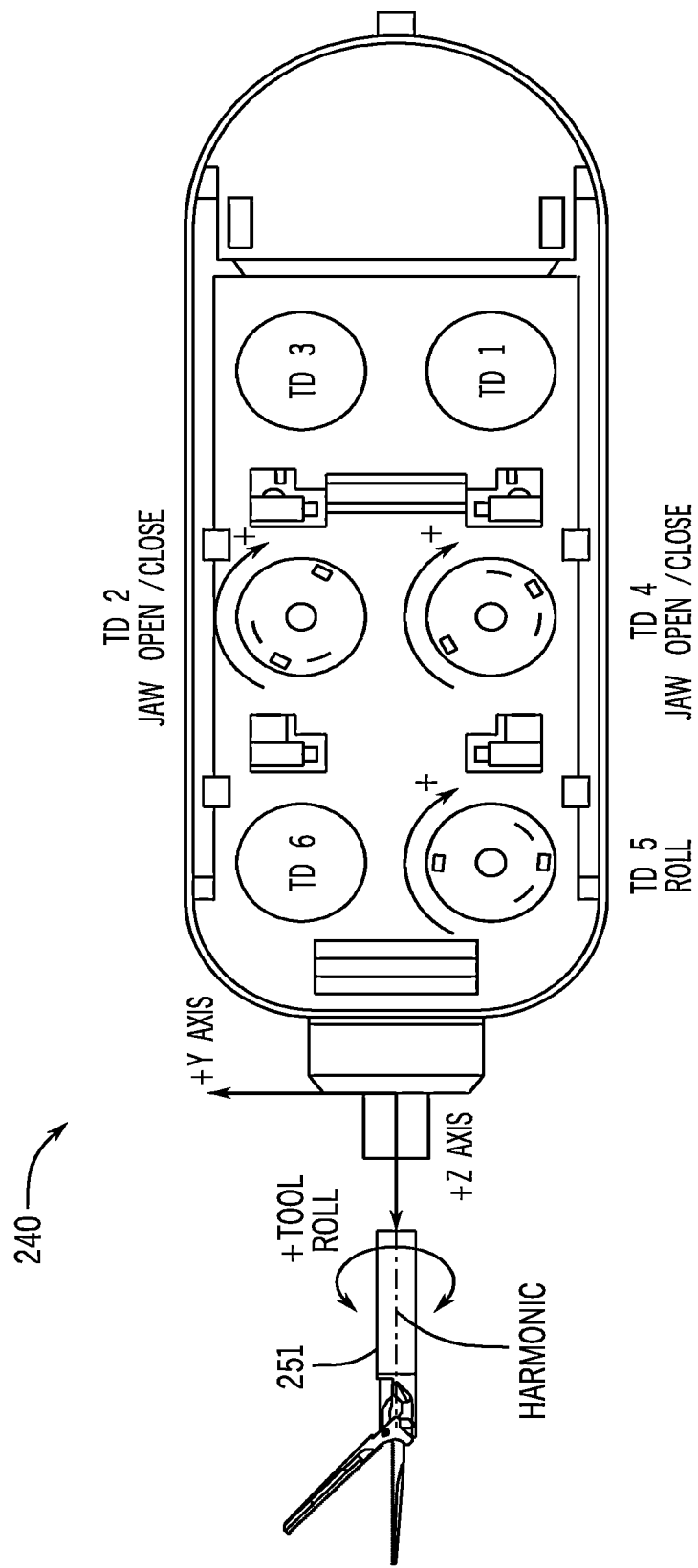
FIG. 4 illustrates an example of the surgical tool including rotary device assignment or mapping for a two degree of freedom surgical tool.

FIG. 4 illustrates an example of the surgical tool 240 including rotary device assignments or mapping for tool disks TD1-6. In this example, tool disks TD5 is mapped to the roll axis of the end effector, which is illustrated as jaw 251, tool disks TD2 and TD4 are mapped to the jaw 251, and tool disks TD1, TD3, and TD6 are unused or unmapped.

Figure 5:
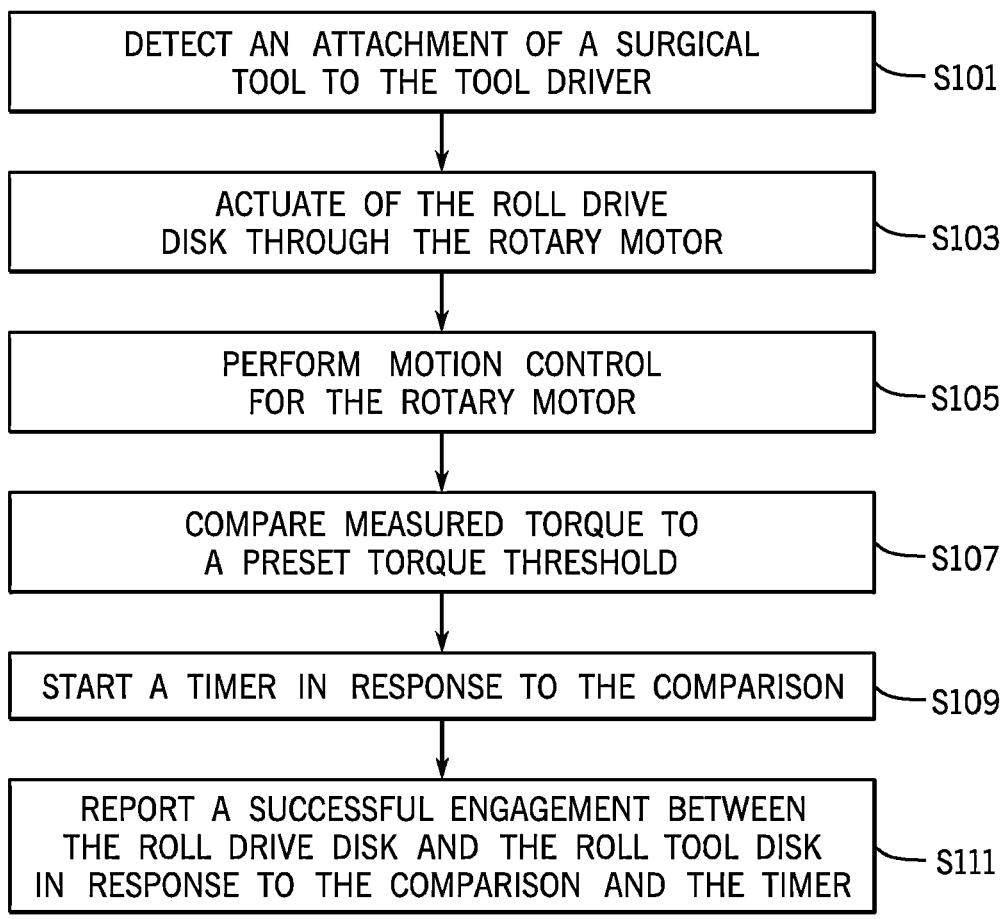
FIG. 5 illustrates an example flow chart for roll joint engagement.

FIG. 5 illustrates an example flow chart for one or more algorithms or processes for roll joint engagement in a tool driver with no physical constraints associated with the roll joint. The process may be performed by a programmed processor or controller configured according to software stored in memory. For example using the processor 312 and the memory 314 of FIG. 3, the processor 312 is configured according to the instructions of the tool control 320 and the engagement control 316. Additional, different, or fewer acts than those in FIG. 5 may be performed.

Figure 6:
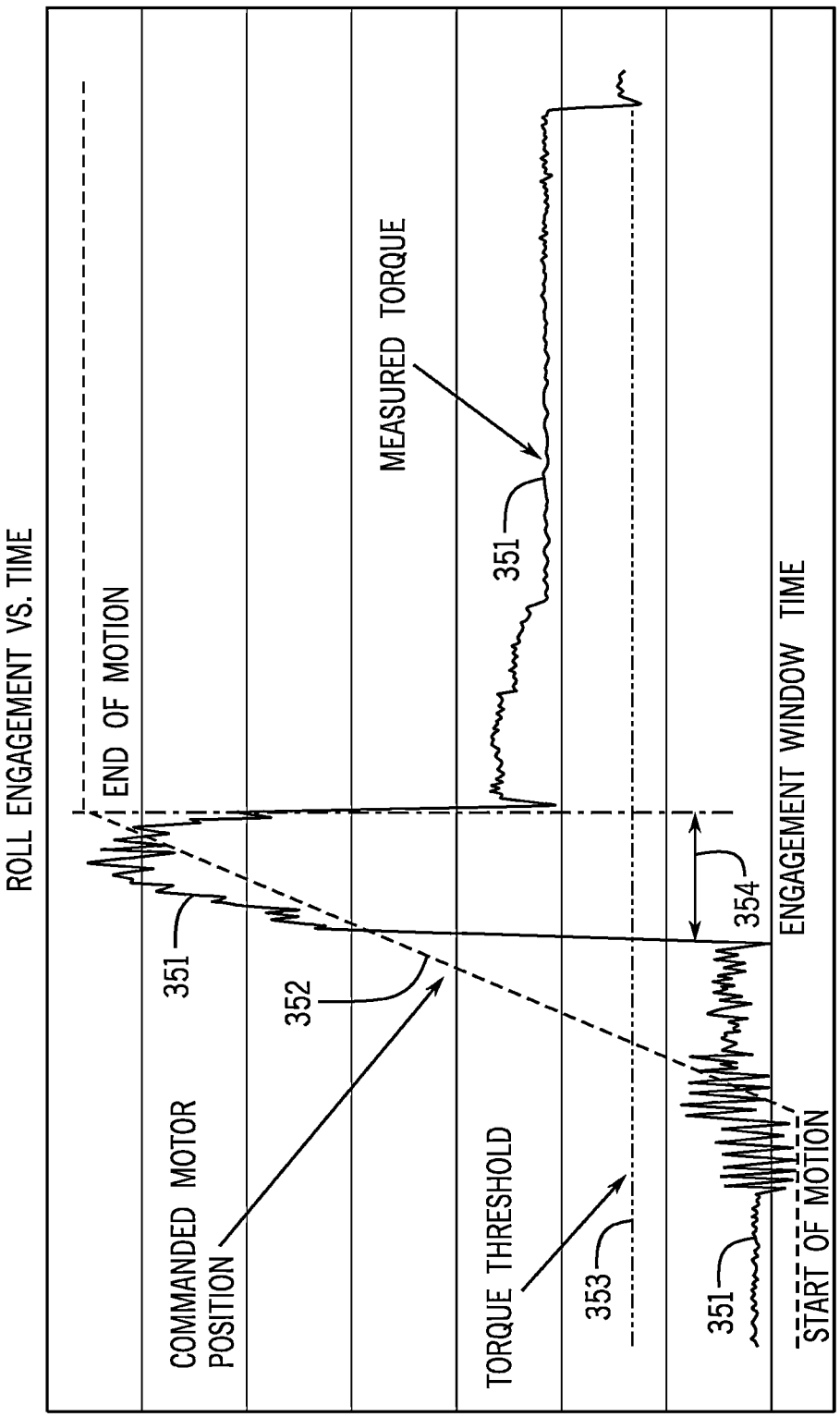
FIG. 6 illustrates an example timing chart for roll joint engagement.

The acts of FIG. 5 are described below with reference to FIG. 6. FIG. 6 illustrates an example chart for roll joint engagement versus time. The chart includes a measured torque plot 351 and a motor control plot 352 as well as an example torque threshold 353 and an example engagement time window 354.

At act S101, the processor 312 detects an attachment of the surgical tool 240 to the tool driver 230 of a robotic arm of a surgical robotic system. The attachment indicates roll tool disk 244 is engaged or positioned in contact with the roll drive disk 234 of the tool driver 230. The processor 312 may receive sensor data from one or more sensors of the sensor array 236 or access sensor data from memory 314. The sensor data is indicative of whether or not the surgical tool 240 is present (i.e., mechanically attached to the tool driver 230). The sensor data may be collected by presence sensor 341, which is any type of sensor operable to generate sensor data for the presence of the surgical tool. In some examples, presence may be detected according to an electrical contact or a communication path between the tool driver 230 and the surgical tool 240.

The attachment may be detected based on the communication path that results when the sensors of the tool driver 230 are within wireless detection range or being conductively connected (e.g., via the communication interface 232) with the information storage unit 242 in the detachable surgical tool 240. The information storage unit may include a tool identifier, and may also include additional tool attributes, such as which of several available tool disks in the tool housing are actually connected by a transmission in the housing to the end effector 246 in the detachable surgical tool 240, what direction of movement or rotation is allowed, if there are any ranges of such movement or rotation, calibration values (e.g., opening/closing polynomial curves as discussed herein, backlash size as discussed herein, maximum jaw opening threshold, rotational position of tool disks or a home position of a tool disk, etc.), as well as other tool attributes discussed herein.

Thus, in one alternative example, the sensor data for presence is provided by the existence of the sensor array 236 in communication with the tool driver 230. For example, the electrical contact may correspond to an electrical connection between the tool driver 230 and the surgical tool 240 such that data is transferred from the surgical tool 240 to the tool driver 230.

In another example, the presence of the surgical tool 240 at the tool driver 230 may be determined based on data collected by the torque sensor 342, the position sensor 343, the current sensor 345 (e.g., or another electrical sensor such as voltage sensor), the optical sensor 347 and/or the force sensor 348.

At act S103, the processor 312 is configured to actuate the roll drive disk 234 through the motor or actuator 238. For example, the processor 312 may generate one or more actuation commands for movement of the roll drive disk 234 through operation of the motor. The command may be a new position of the motor (e.g., angular position) or a directional instruction (e.g., clockwise or counterclockwise) by a certain amount. When mechanically engaged, the rotation of a drive disk (e.g., disk 234-*j*) may cause immediate or direct rotation of a corresponding tool disk (e.g., disk 244-*j*) of a surgical tool (e.g. surgical tool 240).

The processor 312 monitors one or more motor operating parameters of the actuator 238 that is causing the rotation of the drive disk while activating the motor. In some embodiments, the operating parameters of the motor being monitored may include torque, motor current, motor velocity, or a combination thereof. Torque is used as an example below.

In acts S105-S111, the processor 312 is configured to determine that a measured torque (e.g., measured torque plot 351) of the rotary motor exceeds a preset torque threshold for a preset period of time since the actuation. In act S105, the processor 312 performs motion control for the rotary motor. The following provide examples of the motion control in position control mode or velocity control mode applied to the rotary motor in order to monitor torque.

In motion control, the processor 312 may generate a ramp command, or series of ramp commands, for the rotary motor. The ramp commands may include position commands for a position control mode including a predetermined speed (e.g., slow speed) with smoothing at the initial state and the final state. For example, the motor control plot 352 of FIG. 6 illustrates the ramp of the rotary motor position from a first or beginning position at the initial start of motion, through various positions for a substantially constant velocity for the ramp, and finally to a second or end position at the end of motion.

The position control mode may include a linear segment with parabolic blends (LSPB). The ramp commands may include constant velocity commands for a velocity mode to achieve and maintain a constant velocity for the rotary motor.

Figure 7:
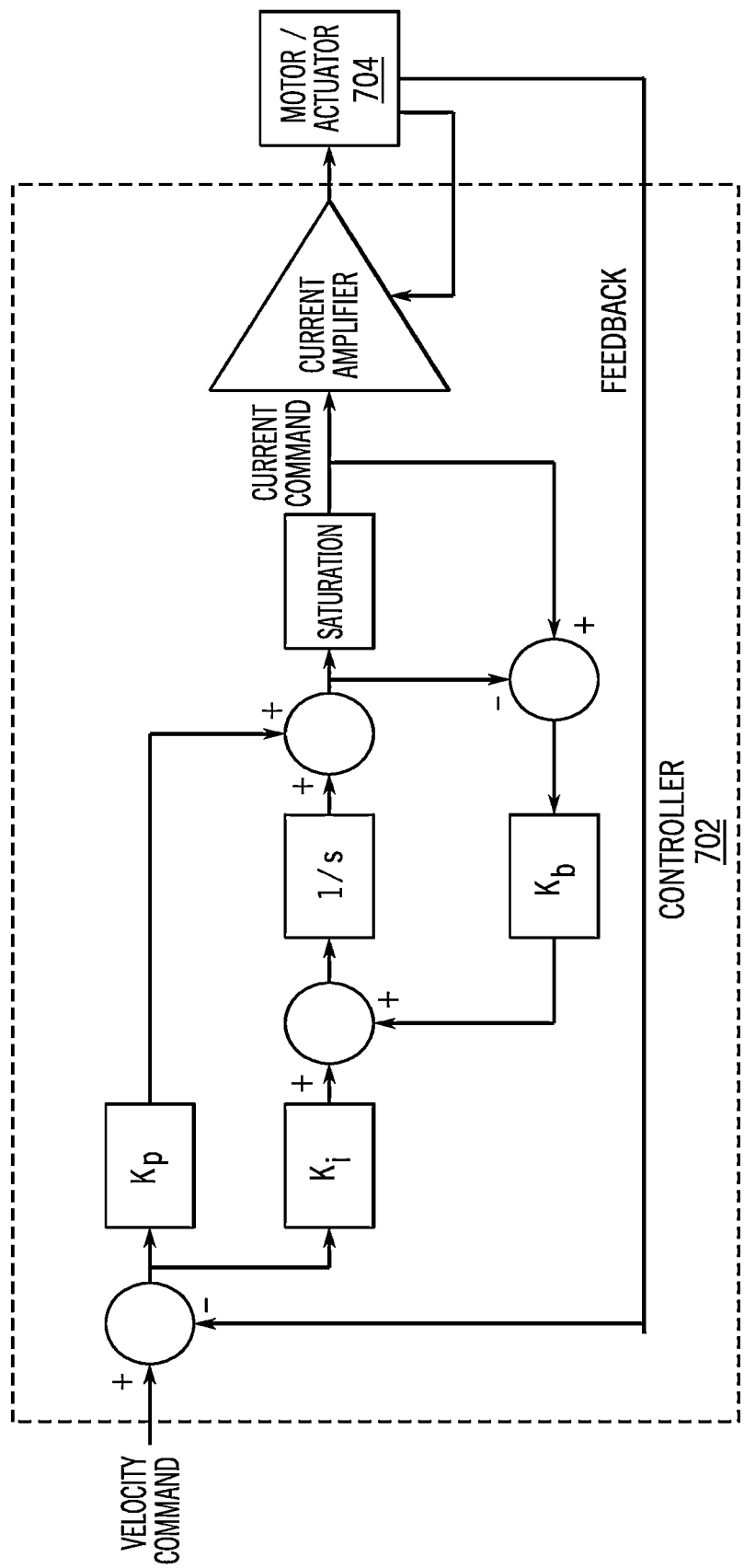
FIG. 7 illustrates an example control block diagram roll joint engagement.

FIG. 7 illustrates an example control block diagram for the velocity mode including a feedback loop implemented by a controller 702 for the rotary motor of the tool driver 230 (e.g., the controller 702 may be implemented by the control unit 210 and/or the processor 312 described herein). In one embodiment, the controller 702 is a proportional-integral (PI) controller may be implemented in part as hardware, firmware, software, or a combination thereof.

In this embodiment, the motor is placed in velocity control mode, and is commanded to rotate at a constant velocity. A velocity command (e.g., control variable setpoint) is received by controller 702. Controller 702 provides a loop/feedback mechanism to adjust and provide an appropriate current (e.g., the controller output) to drive motor/actuator 704 at the velocity and in the direction of the velocity command/setpoint.

In one embodiment, the controller 702 may use various values, such as maximum torque to achieve the velocity as a measure for generating the controller's current output to motor/actuator 704.

Adjustments are made to the original velocity command, such as proportional adjustment (e.g., block with $k_p$) to adjust the velocity proportional to an error (e.g., as determined by the feedback), as well as an integral adjustment (e.g., block with $k_i$) to adjust the velocity to account for past error integrated over time. The integral adjustment may further be adjusted using a restoring term generated by block $k_b$ which is in feedback loop for anti-windup, to further adjust the value of the integral adjustment. The integral adjusted value as shown by block 1/s is added to the proportional setpoint adjusted value.

In one embodiment, a saturation block may be used in controller 702 as shown, to ensure that a value controlling the current supplied to the motor does not exceed a threshold, e.g. a current threshold or limit, torque threshold or limit, etc. The current limit in the saturation block is set in such a way that generated torque is higher than joint friction and inertial effect.

After the adjustments are carried out by the blocks discussed above, and the resulting current command value does not exceed the value set in the saturation block, the current command (e.g., the adjusted command, which has been corrected based on the feedback and PI adjustments) is fed into the current amplifier, so that the commanded current into the motor/actuator 704 can be amplified by a factor. The factor may be fixed, based on properties of the motor/actuator 704, based on feedback from the motor/actuator 704, etc. The factor may be 1 (e.g., not amplified). The motor/actuator 704 is activated as per the commanded current, and feedback on the velocity response of the motor/actuator 704 is provided to the feedback loop implemented by controller 702. The feedback may include current speed or velocity values as determined from sensor data collected by the position sensor 343 (e.g., velocity as first derivative of position). The controller 702 may calculate speed or velocity from a series of position values.

The feedback may be used as a motor operating parameter value supplied to the processor for purposes of monitoring during the engagement process. Other variables computed in the controller 702 (e.g., adjusted and non-adjusted) may be used as a monitored motor operating parameter.

After engagement algorithm detects engagement, the actuator's position is recorded or designated as home position (e.g., in memory 314) and the rotary motor is placed in the position mode in order to hold the position of the motor.

At act S107 of FIG. 5, the processor 312 compares a measured torque (e.g., as indicated by measured torque plot 351) to a preset torque threshold 353. The measured torque may be determined from sensor data from the torque sensor 342. The torque sensor 342 may be an integrated torque sensor in the drive stack that is connected to the roll mechanism using tool disk 244 or drive disks 234 (e.g., a puck formed of plastic). The roll mechanism corresponds to the operation of the roll angle of the end effector 246. However, this embodiment may be applied to other angles of the end effector 246 such as the yaw angle or the pitch angle and/or any degree of freedom of the surgical tool 240 having no physical constraints.

It should be noted that because there is no mechanical hardstop or other physical constraint in the rotary design for the degree of freedom for roll angle, the shaft of the surgical tool 240 can freely rotate without any limit. So an engagement event (i.e., the mechanically coupling of the tool driver 230 and the surgical tool 240) cannot be identified through only a comparison of the measured torque to a threshold and a comparison of a measured velocity being zero or near zero (within noise limits). In other words, engagement cannot be detected through a single torque threshold where there are no hard stops (e.g., physical hard stops or effective hard stops).

Instead, a combination of a preset torque threshold and a time window (e.g., time window 354) under motion control provides detection of roll engagement. Once the rotary motor and instrument are coupled together, an instantaneous increase in the measured torque occurs. This torque value of the preset torque threshold corresponds to breaking static friction between the moving disk (e.g., tool disk 244) driven by the rotary motor and the drive disk 234 at the instrument interface. In addition, as soon as the friction is overcome and shaft starts to move, torque dramatically drops. These two force features are used in the algorithm to detect engagement and stop motion.

The processor 312 may access a preset torque threshold from the memory 314. The preset torque threshold may be selected using a variety of techniques. The preset torque threshold may be selected based on the moment of inertia for the surgical tool 240 and/or the drive system. For example, when the surgical tool 240 is coupled to the tool driver 230, the processor 312 may determine (e.g., through electrical contact, RFID tag, bar code, or other techniques) an identifier for the surgical tool 240 or end effector 246. In addition, data for the identifiers for the tool disks being used, the type of transmission for the tool disks, and/or one or more tool calibration values may be received at the processor 312. The processing 312 or memory 314 may include a lookup table that associates the possible identifiers for the surgical tool and/or drive system with inertial values or with preset torque thresholds.

In addition, the processor 312 may calculate or identify a torque offset that is used to tune or modify the torque threshold. Over time, for example, during each engagement procedure, or prior to act S101, the processor 312 modifies the torque threshold through addition or subtraction of the torque threshold. An initial torque offset from the mechanical alignment and weight of the surgical tool 240, the associated robotic arm, of the tool driver 230, or of another associated device is subtracted from torque readings for engagement detection.

The torque threshold may also be tuned or calibrated. If the torque threshold is set too low, inherent frictional forces of the motor drive stack and disks may cause false-positive detection signals. Similar effects may be seen from temporary variation in measured values due to noise. Small torque peaks are expected prior to the main torque spike that corresponds to engagement. If the torque threshold is set too high, engagement detection may fail. The friction of the rotary axis of the surgical tool 240 is greater than the total friction in motor gear box plus disks. The latter is a low-friction mechanical interface between tool driver 230 and the surgical tool 240.

At act S109, the processor 312 starts a timer or a counter in response to the comparison of S107, for example, when the measured torque of the rotary motor exceeds or meets the preset torque threshold. The timer may include a separate device (e.g., integrated circuit timer device) or allocated portion of the processor 312.

When the measured torque exceeds (or meets) the preset torque threshold, the timer is started. The processor 312 includes instructions to compare the timer to the predetermined period of time. The timer continues to run (increment time) as long as the measured torque continues to exceed (or meet) the preset torque threshold. The timer may output a signal when the timer reaches a predetermined time period (engagement window time).

The engagement window time may be selected according to a variety of techniques. Total engagement that impacts engagement window may be chosen based on clinical needs and high-level system requirements. However, engagement window time may be determined by some trials and errors and is a configurable parameter. The engagement window time may be set empirically to maximize system performance and minimize engagement detection failure rate. The engagement window time may be selected based on an identifier for the surgical tool 240 or end effector 246. In addition, data for the identifiers for the tool disks being used, the type of transmission for the tool disks, and/or one or more tool calibration values may be received at the processor 312. The engagement window time may be specified by other system requirements or clinical needs. Different procedures may be associated with different engagement window times. The processor 312 may include a lookup table that associates surgical tool models, surgical procedures, or other hardware with different engagement time windows.

In response to the signal output from the timer, the processor 312 determines that engagement of the tool driver 230 and the surgical tool 240 has occurred. At act S111, the processor 312 reports a successful engagement between the roll drive disk 234 and the roll tool disk 244 in response to the comparison of act S107 and the timer of act S109. That is, when the counter overflows because the torque remains above the threshold for the engagement window time, an engagement message is generated by the processor 312.

Once roll engagement is detected, the ramp position command is stopped by gradually decreasing commanded velocity followed by full stop using position hold mode. The processor 312 initiates a position hold mode in response to the successful engagement report or signal. The processor 312 sends a command for a full stop to the rotary motor. For example, the commands sent to the rotary motor may decrease a velocity for the actuation of the roll drive disk 234 through the rotary motor in response to the successful engagement. The position at successful engagement is recorded as home position of the rotary axis during teleoperation in response to the full stop.

For example, the processor 312 stores the home position with a code (e.g., a numeric value or alphanumeric value) for the current position of the drive disk 234, for example, as detected by the position sensor 343. Subsequently, the home position may be used to define further actuation commands for the operation of the surgical instrument 240. The control unit 210 may send data indicative of the successful engagement to the display unit 319 to report a successful engagement between the roll drive disk 234 and the roll tool disk 244. The display unit 319 may display such information to the user to report the successful engagement.

Since there is no hardstop to limit the motion, it is safe to start the motion and keep monitoring measured torque signal until engagement. However, when engagement is not successful, other output messages or output signals may be provided by the processor 312. For example, a warning may be generated if engagement is not successful before one or more limits. The warning message includes data indicative of a failure of the engagement procedure.

In one example, the one or more limits may include a travel distance for a rotary device (e.g., angular travel distance of the rotary motor, drive disk 234 and/or tool disk 244). The processor 312 is configured to determine a travel distance for the rotary device. The travel distance may be calculated based on the sensor data from position sensor 343. The travel distance may be the difference between the current position of the rotary device (e.g., along the ramp of the motor control plot 352) and the initial position of the rotary device while accounting for any number of rotations. The processor 312 compares the travel distance to a travel distance limit. The travel distance limit may be accessed from memory 314. The travel distance limit may be based on a tool identifier, a tool attribute, a calibration value, a type of end effector, or a type of surgical procedure. In one example, the travel distance is set to a set number of rotations (e.g., 1 or 2 rotations represented in radians or degrees) of the rotary device. The processor 312 generates a warning message in response to the travel distance exceeding the travel distance limit.

In one example, the one or more limits may include a maximum velocity for the rotary device. The processor 312 is configured to set a maximum rotation velocity, which may be a tool specific parameter. The maximum velocity may be based on a tool identifier, a tool attribute, a calibration value, a type of end effector, or a type of surgical procedure. The maximum rotation velocity is an algorithmic parameter. If the maximum rotation velocity is set too high, the engagement detection algorithm may be very sensitive to stiction, which is the static friction that opposes stationary surfaces from being set in relative motion under one or more forces. If the maximum rotation velocity is set too low, engagement may not be achieved within the desired time.

The warning message may be a warning message presented to a user, transmitted to a central controller, or a message internal to the control unit 210.

The warning message presented to the user (e.g., via the display unit 319) may indicate that the engagement is unsuccessful. The warning message may present instructions to detach the surgical tool and/or repeat the engagement process. The warning message may prompt the user to confirm the restart of the engagement process or to detach and reattach the surgical tool 240 or the tool driver 230. The engagement process may be automatically repeated through detachment and reattachment.

The warning message may be transmitted to a central controller. For example, the failure of the engagement process may be sent to a manufacturer for the purpose of logging the failure and monitoring tool drives in use. The central controller may dispatch maintenance or disable the tool driver 230 in response to a predetermined number of engagement failures.

An internal warning message may indicate to the control unit 210 that the engagement failure has occurred. In response, the control unit 210 may require the tool drive be placed in a maintenance mode for calibration to be performed. The control unit 210 may disable the tool drive after a predetermined number of failed engagement attempts. The control unit 210 may restart the engagement process in response to the internal warning message. That is, the processor 312 may return to act S101 in response to the warning message.

Returning to act S109, the engagement time window 354 may be interrupted or restarted in certain scenarios. If the measured torque returns to below the preset torque threshold during the engagement time window 354, the process may be repeated, in part. For example, the processor 312 may determine, after the actuation, that the measured torque of the rotary device is less than the preset torque threshold. The engagement process returns to act S107 and/or act S109. The processor 312 may return to act S107 to confirm that the measured torque is above the preset torque threshold. In addition, or in the alternative, the processor 312 may return to act S109 to reset the counter in response to the measured torque of the rotary motor being less than the preset torque threshold.

Closure Joint Engagement and Synchronization

One or more embodiments to synchronize two motors during engagement and homing of a coupling mechanism are described. Using two or more coupled motors, the end-effector load is divided, such as equally divided or substantially equally divided (e.g., within 10% of equal force), between two or more motors. The motors constrained through the coupling mechanism move together and theoretically carry half, or a nearly equal proportion, of the delivered torque. In this case, the coupling mechanism is utilized to generate a linear motion in order to operate the end effector of a surgical instrument. For example, the linear motion may open and close a jaw or other closure joint to provide desired clamp force at its distal end. Devices could be prone to bending and breakage if interaction between actuators is not safely controlled.

As a general description of the interaction between the surgical tool 240 and the tool driver 230, the engagement control 316 performs (or rather configures the processor 312 to perform) the process for detecting the mechanical engagement of tool disks with corresponding drive disks (which are actuator driven). Subsequently, the tool control 320 performs (or rather configures the processor 312 to perform) the process for one or more of the actuators of tool driver 230 to impart motion of their respective drive disks. The instructions or signals include instructions to energize, activate or otherwise provide power to a motor so that the motor can produce or apply a specific amount of torque, cause the drive disk to rotate at a specific speed and direction, or move to a particular position by applying a certain voltage command, current command, etc.

The operation of the tool control 320 may include a homing control or homing process in which one or more calibration settings are established. The calibration settings may include a home position or a zero position in which the relative position of the actuator 238 of the tool driver 230 to the surgical tool 240 is detected, or the actuator 238 is moved to the home position. After the tool is fully engaged, which may include both roll and closure joints engagement, the instrument shall be homed. The homing process may bring the tool from the post-engagement configuration, which has a random nature, to a predetermined orientation. In response to successful homing, the tool control 320 performs normal operation (or rather configures the processor 312 to perform) the process for one or more of the actuators of tool driver 230 impart motion of their respective drive disks under the direction of commands from the user cause the motor to operate at a specific amount of torque, the drive disk to rotate at a specific speed and direction, or other operation.

In certain embodiments two coupled actuators or motors are synchronized to drive a component of the tool driver 230. In another embodiment, more than two coupled actuators may drive a component. The component may be the closure joint that opens and closes jaws of the end effector 246. However, this embodiment may be applied to other tools having at least one degree of freedom limited by a hardstop or physical constraint included in the surgical tool 240 to impede the motion of a tool disk 244 and/or a drive disk 234 at a prescribed maximum range of motion.

FIGS. 8A, 8B, and 8C illustrate an example set of motor/actuators for a tool drive associated with a hardstop 239 and a hardstop switch 241. The set of motor/actuators includes a first motor/actuator 235 and a second motor/actuator 237. The set of motor/actuators may correspond to any of the tool disks 244 and/or the drive disks 234 described herein, for example, an opposing pair of tool disks, as illustrated in FIG. 4 as TD 2 and TD 4. The first motor/actuator 235 and the second motor/actuator 237 are physically coupled to one another through at least one coupling device or driven mechanism. The coupling device or driven mechanism may serve as a hardstop that substantially prevents one of the first motor/actuator 235 and the second motor/actuator 237 from moving in opposition or out of synchronization of the other of the first motor/actuator 235 and the second motor/actuator 237. Thus, the hardstop 239 may not be actually standalone components but rather implemented in the drive system that mechanically couples the first motor/actuator 235 and the second motor/actuator 237. The hardstop switch 241 is operable to be actuated in connection with a hardstop associated with the first motor and the second motor. In some examples, the hardstop switch 241 provides a signal to interrupt the first motor or the second motor.

FIG. 8A illustrates an example alignment of relative positions between the first motor/actuator 235 and the second motor/actuator 237 before any motion is imparted from the tool control 320. Due to random positioning of each tool driver disk, one axis may travel much longer than the other axis before initial engagement. If a torque ramp up activates right away and without syncing between the two motor/actuators, the first engaged actuator may contact a hardstop (e.g., yoke hardstop) much earlier than the other one of the motor/actuators contacts a hardstop.

FIG. 8B illustrates an example of this type of asynchronous motion. In this scenario, the first motor/actuator 235 and the second motor/actuator 237 have been operated asynchronously such that the position of the first motor/actuator 235 is substantially different than the second motor/actuator 237. An amount of deviation sufficient for asynchronous motion may be defined according to a predetermined distance between the first motor/actuator 235 and the second motor/actuator 237. The amount of deviation may be defined according to the type of hardstop 239 or other physical aspects of the tool driver 230. The asynchronous motion may impact the overall safety of motion as well as repeatability of a force delivered by the surgical tool 240. In extreme cases, asynchronous motion can lead to breaking the instrument, or a major drop in the force delivered by the surgical tool 240, causing an undesired medical event during surgery. Likewise, the bending of hardstop switch may cause damage to the instrument.

FIG. 8C illustrates synchronous motion of actuators 235 and 237 to prevent the tilting of hardstop 239 due to the asynchronous motion. In this embodiment, a two-stage sequential engagement and homing process can be adopted to ensure that there is no undesired rotation/tilting of the hardstop 239 (e.g., yolk). Moreover, the two-stage process reduces or prevents damage or other negative effects on the hardstop switch 241. For example, negative effects may include physical damage or distortion such as bending the switch or may include displacement or movement of the switch outside of intended operation. The homing process prevents these effects and, as a result, improves overall safety of motion as well as the repeatability of force delivered by the device.

Figure 9:
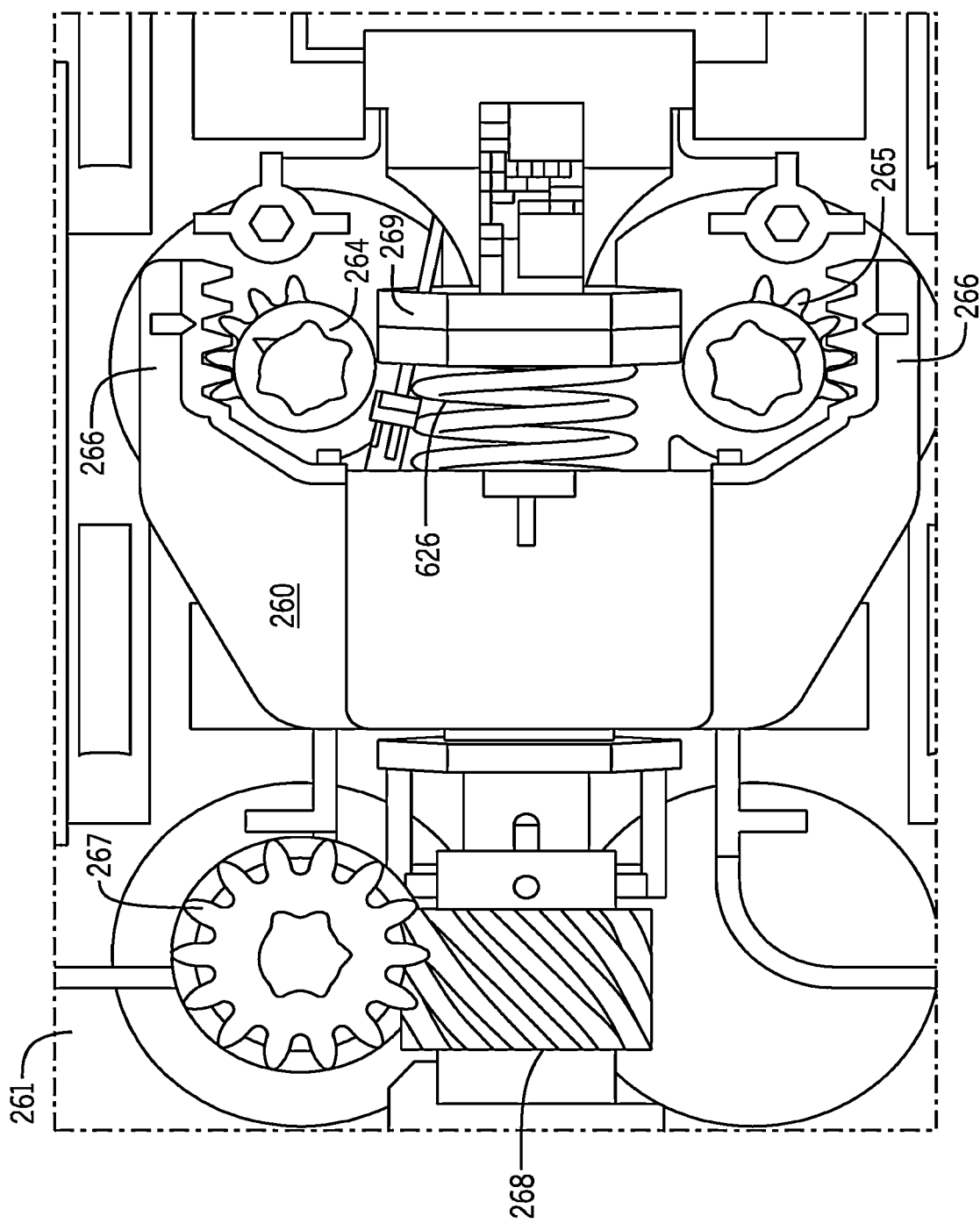
FIG. 9 illustrates a yoke mechanism for the example of FIG. 8.

FIG. 9 illustrates a specific example in which a yoke mechanism 260 is the coupling device associated with the first motor/actuator 235 and the second motor/actuator 237 such that the yoke mechanism 260 physically couples the first motor/actuator 235 and the second motor/actuator 237. The end of the yoke mechanism 260 may include a rack gear 266, which may include an abutment portion in line with the rack gear 266 that serves as a hardstop.

The coupling device may also include the spring 262, which provides a hardstop when the spring 262 reaches a maximum compression level defined by a spring characteristic, because the spring is pressed against a back stop 269. The spring 262 may be a wave spring that allows the coupling device to move only a set distance (e.g., 1 millimeter, 4.5 millimeters, 10 millimeters, or another value). Other hardstops may be implemented with tabs or adjustable limiters for any portion of the drivetrain.

One or more helical gears (e.g., helical gear 267 and helical gear 268) rotates the shaft for the roll degree of freedom. For the closure joint, the yoke mechanism 260 includes rack gears 266 that mesh with rack gears 264 and 265 that move in unison to slide the yoke mechanism 260 in order to open and close the jaw closure 251.

Figure 10A:
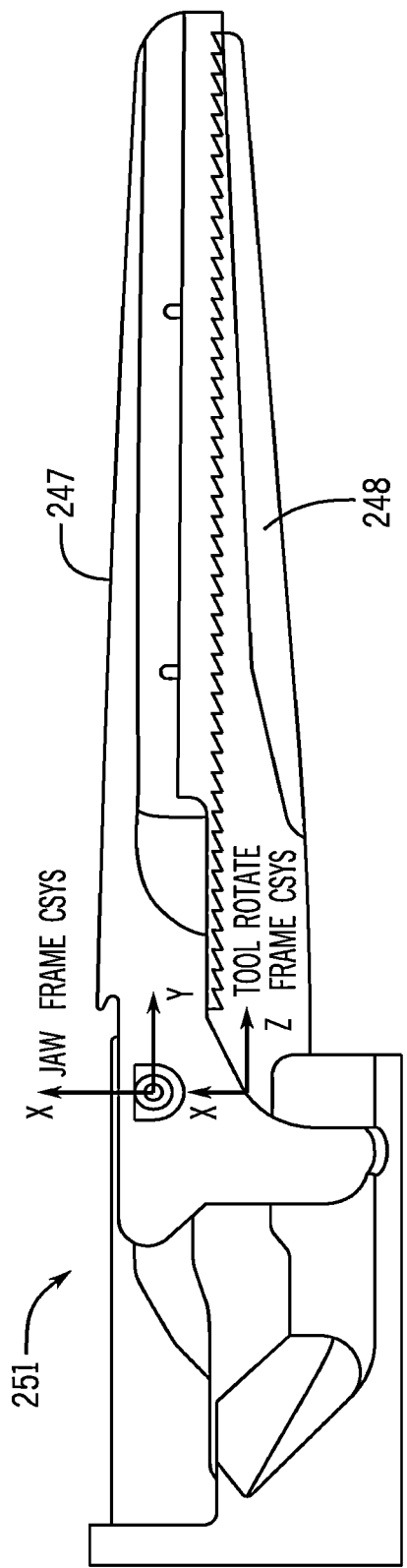
FIGS. 10A and 10B illustrate an example closure coupled to the yoke mechanism.
Figure 10B:
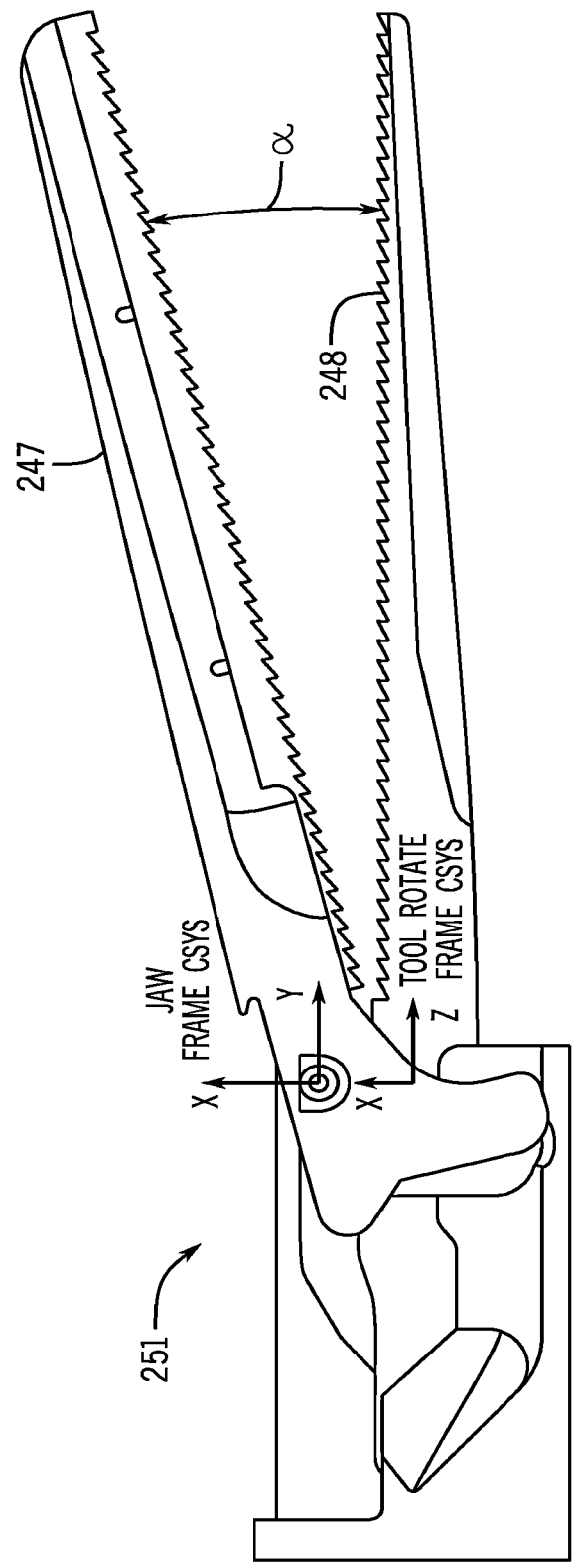

FIGS. 10A and 10B illustrates an example in which the end effector includes an example jaw closure 251 coupled to the yoke mechanism 260. The jaw closure 251 includes an upper jaw 247 and a lower jaw 248. The lower jaw 248 may be connected to an inner tube in the shaft that is fixed. The upper jaw 247 may be jointly moved by the rack gears 264 and 265 via a sliding output tube. The upper jaw 247 pivots about its center of rotation. The upper jaw 247 may be driven by the end effector gear 264 and/or gear 265 and the lower jaw 248 is stationary.

FIG. 10A includes a closed state for the jaw closure 251 and FIG. 10B illustrates an open state for the jaw closure 251. In some examples, only the upper jaw 247 is rotated relative to the lower jaw 248 or only the lower jaw 248 is rotated relative to the upper jaw 247. In other examples, both the upper jaw 247 and the lower jaw 248 are rotated toward and away from each other simultaneously. In one example, the jaw closure 251 varies from 0 to 44 degrees for the internal jaw angle.

A two-step algorithm may be applied to sequentially engage and home the closure joint. A combined torque-position controller is utilized to convert a desired torque command to a position command for driving and actuating the mechanism.

Figure 8:
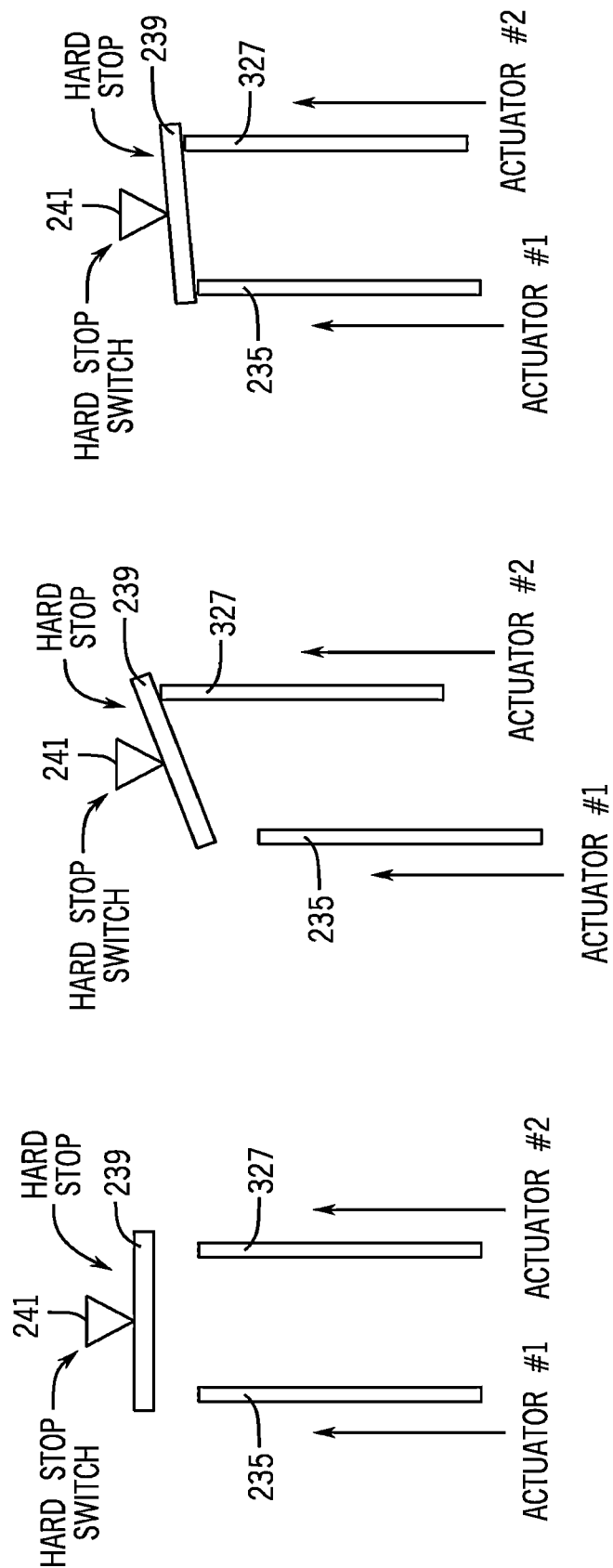
FIGS. 8A, 8B, and 8C illustrate example related sets of actuators for a tool drive associated with a hardstop.
Figure 11:
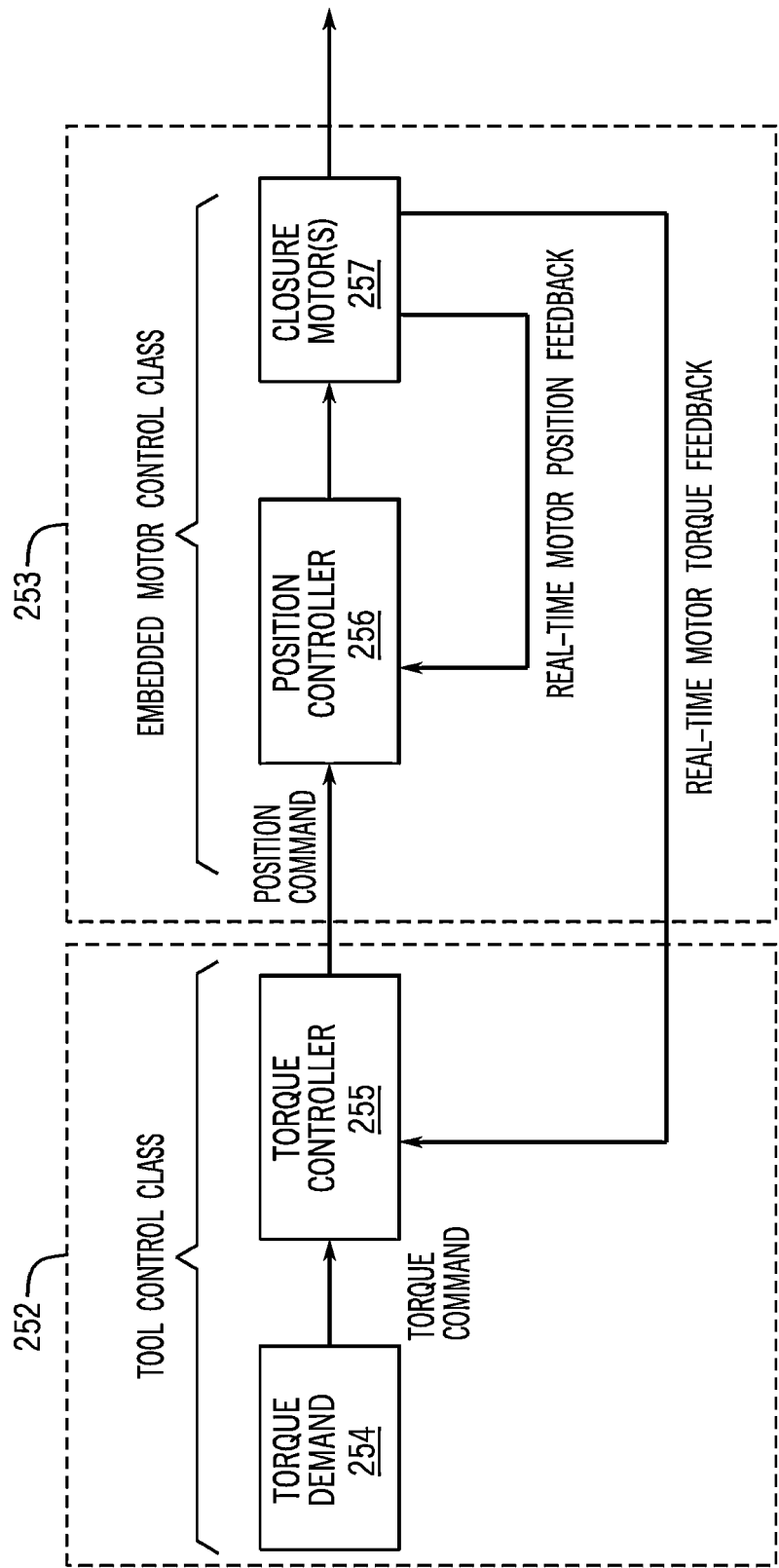
FIG. 11 illustrates an example block diagram for torque control and position control for the example of FIG. 8.

FIG. 11 illustrates an example block diagram for torque control and position control for the example of FIG. 8, which may be applied to the yoke mechanism 260 of FIG. 9 and the jaw closure 251 of FIGS. 10A and 10B. The two component motors may collaborate together to slide the yoke mechanism 260 during engagement of the tool driver 230 to the surgical tool 240. These embodiments including syncing during a two-stage sequential engagement and homing to ensure that the yoke mechanism 260 does not bend or hit its hardstop switch without causing undesired rotation of the hardstop.

The block diagram of FIG. 11 includes a tool control class 252 and an embedded motor control class 253. The tool control class 252 includes a torque demand 254 transmitted as a message or signal and a torque controller 255 for torque control as an example implementation of a PI (proportional-integral) controller that forms an outer loop of the control system. The embedded motor control class 253 includes a position controller 256 and the closure motor controls 257 (e.g., the first motor/actuator 235 and the second motor/actuator 237) as an example implementation of a PD (proportional-derivative) controller that forms an inner loop of the control system. The tool control class 252 may represent high-level control implementation, and the embedded motor control class 253 may represent the embedded level.

Torque demand 254 may include a command (e.g., torque command) that specifies an operation of the motor. A torque controller 255 that interprets the torque demand 254 and generates a position command sent to the position controller 256. The position controller 256 generates a position command for the closure motors 257 for operating the end effector. The operation of the closure motors, as detected by one or more sensors 236, such as position sensor 343, provides a first feedback, or real time motor position feedback, to the position controller 256. The operation of the closure motors, as detected by one or more sensors 236, such as torque sensor 342, also provides a second feedback, real time motor torque feedback to the torque controller 255.

Figure 12:
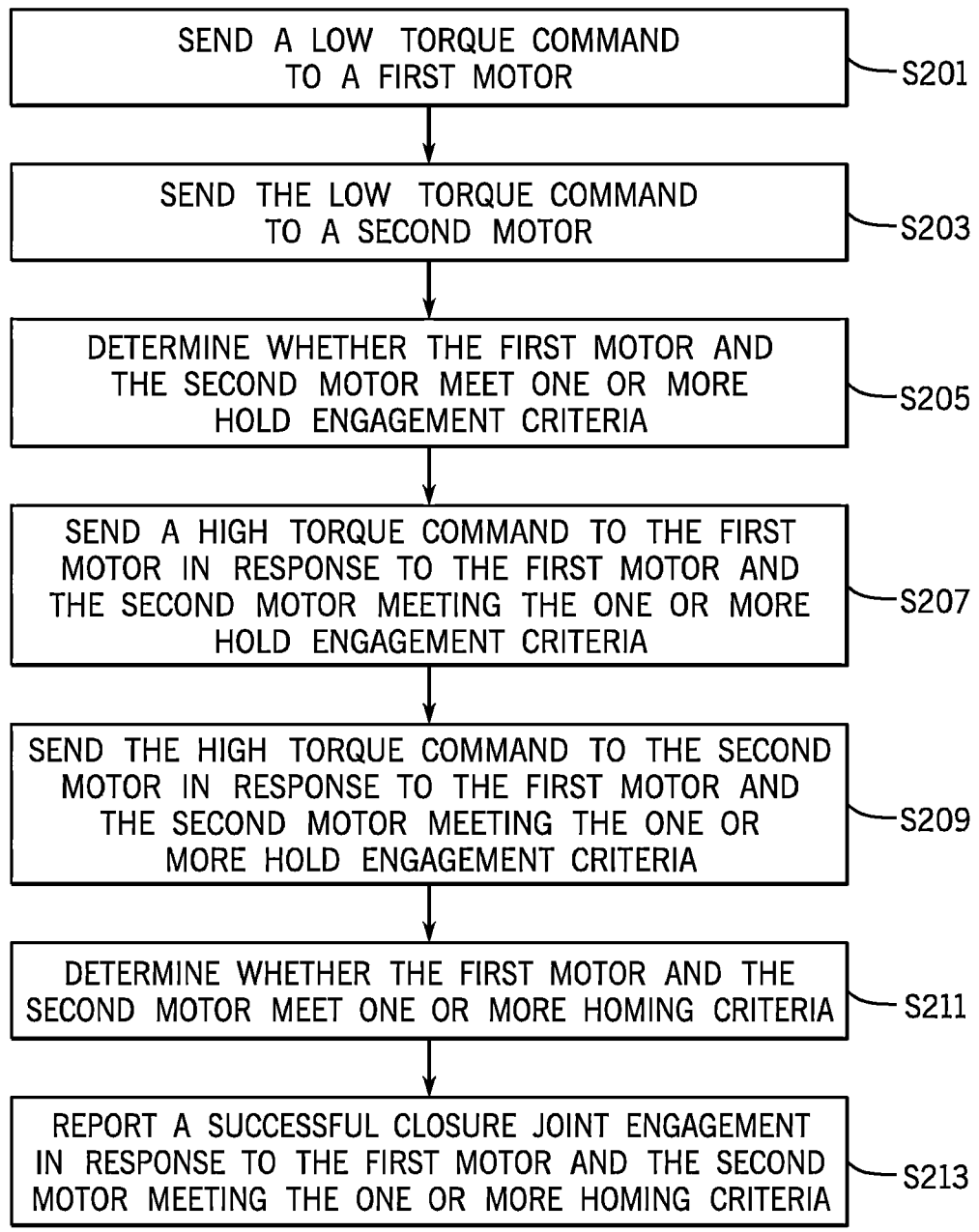
FIG. 12 illustrates an example flow chart for engagement of the joint for the closure.

FIG. 12 illustrates an example flow chart for engagement of the joint for the jaw closure 251 or other end effector tool. The process may be performed by a programmed processor (also referred to here as processor or controller), configured according to instructions stored in memory 314 and executed by the processor 312 of FIG. 3, where the processor 312 is configured according to the instructions of the tool control 320 and the engagement control 316. The processor 312 may be implemented according to a combination of the torque controller 255 and the position controller 256. Additional, different, or fewer acts than those in FIG. 12 may be performed.

As a preliminary stage, and as discussed previously with respect to act S101 of FIG. 5, the processor 312 detects an attachment of the surgical tool 240 to the tool driver 230 of a robotic arm of a surgical robotic system. The attachment indicates roll tool disk 244 is engaged with the roll drive disk 234 of the tool driver 230. The processor 312 may receive sensor data from one or more sensors of the sensor array 236 or access sensor data from memory 314. The sensor data is indicative of whether or not the surgical tool 240 is present (i.e., attached to the tool driver 230). The sensor data may be collected by presence sensor 341. The attachment may be detected based on the communication path that results when the sensors of the tool driver 230 are within wireless detection range or being conductively connected with an information storage unit in the detachable surgical tool. In other example, presence of the surgical tool 240 at the tool driver 230 may be determined based on data collected by the torque sensor 342, the position sensor 343, the electrical sensor 345, the optical sensor 347 and/or the force sensor 348.

Once tool attachment is detected, actuator disks linked directly to driving motors are commanded to move by the processor 312. Instrument closure joint is interfaced to the drive mechanism through at least one disk (e.g., tool disk 244), and interaction torque is measured by integrated torque sensors in the drive stack for each degree of freedom. Two torque sensors measure torques between actuators and tool drive disks 234 to modulate motion to engage and home the instrument safely.

Inside the instrument, two disks coupled together through the yoke mechanism 260 provide input torque to the closure degree of freedom. There also exists a mechanical hardstop (aka physical constraint) that limits the yoke translational motion, so it can freely slide until hitting the hardstop switch. If excessive force is transferred to the hardstop switch, damage to the device may occur. For this reason, the control algorithm prevents damage during use.

At act S201, the processor 312 (e.g., the torque controller 255) is configured to generate and send a low torque command to a first motor (e.g., the first motor/actuator 235). At act S203, the processor 312 (e.g., the torque controller 255) is configured to generate and send a low torque command to a second motor (e.g., the second motor/actuator 237). Acts S201 and S203 may occur at the same time. In other examples, acts S201 and S203 may be performed at nearly the same time. The low torque command initially engages the tool driver 230 to both actuation axes of the instrument for the end effector 246 that are coupled to the first motor and the second motor. To this end, two identical controllers, or control sequences, initialize and run in parallel to drive the two coupled axes. The torque command is set to be low in each in order to overcome friction in the drive stack, move each actuator and engage each actuator and drive disk 234 of the tool driver 230 at the interface level with the corresponding tool disk 244 of the surgical tool 240.

At act S205, the processor 312 determines whether the first motor and the second motor meet one or more hold engagement criteria. The hold engagement criteria may include a single criterion such as a velocity condition or a torque condition. The hold engagement criteria may include both the velocity condition and the torque condition. The hold engagement criteria apply to both the first motor and the second motor. That is, the hold engagement criteria are considered satisfied when both the first motor and the second motor meet the hold engagement criteria.

The velocity condition may be a set threshold such that this aspect of the hold engagement criteria is met when the velocity of the motor, or the corresponding drive disk 234 or the corresponding tool disk 244, is less than or equal to the set threshold. The measured velocity of the motor or corresponding drive may be determined by a sensor 236 such as the change in sensor data from the position sensor 343.

The torque condition may be a set threshold such that this aspect of the hold engagement criteria is met when the torque of the motor, or the corresponding drive disk 234 or the corresponding tool disk 244, is greater than or equal to the set threshold. The measured torque of the motor or corresponding drive may be determined by a sensor 236 such as the torque sensor 342.

In one embodiment, when the processor 312 determines that the velocity condition is satisfied because a velocity of an engaged motor (e.g., the first motor or the second motor) is less than the set threshold and determines that the torque condition is satisfied because the measured torque is also above an engagement torque threshold, the processor 312 generates a wait command for the engaged motor to hold at the set torque level wait for the other motor (e.g., the other of the first motor or the second motor that did not initially engage) to engage. For example, the wait command may be sent to the first motor when the first motor has met the one or more hold engagement criteria and before the second motor has met the one or more hold engagement criteria. Thus, the processor 312 pauses the engaged motor until the other motor has also met the velocity condition and the torque condition. The pause or stop command ends when the velocity condition is satisfied because the velocity of the other motor is less than the set threshold and when the torque condition is satisfied because the measured torque is above an engagement torque threshold. An alternative to the engagement torque may include a range of torque values that indicate the motor is engaged through the drive train with the surgical tool 240.

The processor 312 may determine, or access from memory 314, a synchronized engagement time period. The synchronized engagement period is applied to the two coupled actuators or motors that are synchronized to drive a component of the tool driver 230 that drives a component of the surgical tool 240. For example, the component may be the closure joint the opens and closes jaws of the end effector 246. The synchronized actuator engagement time period may be set according to a user input, a characteristic of the tool driver 230, and/or a characteristic of the surgical tool 240, and may be retrieved from a lookup table based on any of the attributes or identifiers described herein. The actuator engagement time period may be approximately 100 milliseconds, 1 second or another value. The hold engagement criteria may also be associated with the actuator engagement time period such that the processor 312 determines that the hold engagement criteria have been satisfied for the duration of the actuator engagement time period. Thus, in at least one example, the processor 312 determines that both motors have successfully engaged, meaning that both motors meet and hold engagement criteria for the velocity and torque conditions for the actuator engagement time period. The algorithm proceeds to act S207 and subsequent acts to continue synchronization of the first and second motors. If the hold engagement criteria are not met for the actuator engagement time period, the algorithm pauses in wait mode until the criteria are met for the actuator engagement time period.

At act S207, the processor 312 (e.g., the torque controller 255) is configured to send a high torque command to the first motor in response to the first motor and the second motor meeting the one or more hold engagement criteria. Likewise, at act S209, the processor 312 (e.g., the torque controller 255) is configured to send the high torque command to the second motor in response to the first motor and the second motor meeting the one or more hold engagement criteria. Acts S207 and S209 may occur at the same time. In other examples, acts S207 and S209 may be performed at nearly the same time. In other words, both the first motor and the second motor meet the one or more hold engagement criteria before the high torque command is sent to either of the first and second motors.

The high torque command instructs the first and/or second motors to rotate with a torque high enough to overcome the inertial and frictional forces of the surgical tool 240 as well as the drive train (e.g., tool disk 244 and drive disk 234). The high torque command is sent to both actuation axes (the first and second motors) in order to home the instrument against its internal hardstop. As described above, the coupling device provides a hardstop to inhibit relative motion between the plurality of drive disks corresponding to the first motor and the second motor.

The high torque command may include a ramp of torque levels such as a series of torque levels that are increasing over time. The same control scheme introduced beforehand is utilized here to move two motors while torque and/or velocity are being actively monitored.

At act S211, the processor 312 determines whether the first motor and the second motor meet one or more homing criteria. The one or more homing criteria may include a velocity condition, which may be considered a second velocity condition with the first velocity condition being designated for the one or more engagement criteria. The second velocity condition may necessitate a velocity range for the motor/actuators. The velocity range may include zero velocity and span from a positive velocity value to a negative velocity value. The range may be selected to account for noise limitations in the sensor data.

The one or more homing criteria may include a torque condition, which may be considered a second torque condition with the first torque condition being designated for the one or more engagement criteria. The second torque condition may include a torque threshold or a toque range which requires the measurement to be within a close distance of the desired torque target. Such torque criterion guarantees that torque difference between two axes is bounded, so asymmetric bending of the hardstop when hitting the switch is minimized. The torque condition may include a difference between a first torque for the first motor and a second torque for the second motor.

The one or more homing criteria may also be associated with a homing time period. The processor 312 may determine, or access from memory 314, a homing time period applied as the two coupled actuators or motors are synchronized to drive a component of the tool driver 230 that drive a component such as the closure joint that opens and closes jaws of the end effector 246. The processor 312 is configured to start a counter. The counter may include a separate device (e.g., integrated circuit timer device) or allocated portion of the processor 312. The processor 312 compares the counter to the homing time period value.

The homing time period may be set according to a user input, a characteristic of the tool driver 230, and/or a characteristic of the surgical tool 240, and may be retrieved from a lookup table based on any of the attributes or identifiers described herein. The homing time period may be selected to provide sufficient time for the torque control to stabilize. The homing time period may be approximately 100 milliseconds, 250 milliseconds, 1 second or another value. The homing criteria may also be associated with the homing time period such that the processor 312 determines that the homing criteria have been satisfied for the duration of the homing time period. Thus, in at least one example, the processor 312 determines that both motors have successfully homed, meaning that both motors meet the homing criteria for the velocity and torque conditions for the homing time period, the algorithm proceeds to act S213.

If the homing criteria is not met for the homing time period for either the first motor or the second motor, the algorithm pauses in wait mode until the criteria are met for the homing time period. For example, once the velocity condition and the torque condition are met and held within the homing time period for a particular axis or a particular motor, the axis is said to be successfully homed. After the homed axis or homed motor is identified, the processor logic activates the waiting period until the second motor or second actuator passes its own one or more homing criteria for the homing time period. In this way, the first and second motors are sync together to home the device safely.

At act S213, the processor 312 reports a successful closure joint engagement in response to the first motor and the second motor meeting the one or more homing criteria. In the alternative, the processor 312 generates a failure message when the counter exceeds the homing time limit before a successful closure joint engagement. The failure message may include instructions to detach an instrument from the robotic arm. The failure message may include data indicative of a failure.

In at least one example, the homing time period may be interrupted or restarted in certain scenarios. If during the homing time period, the processor 312 determines, after the high torque command is sent, whether the first motor or the second motor violates the one or more homing criteria including the velocity condition or the torque condition, the homing time period, or a counter corresponding to the homing time period is reset. Thus, in response to the counter for the homing time period being reset, the successful closure joint engagement may be identified after a subsequence satisfaction of the homing criteria after the duration of the restarting homing criteria. Therefore, during act S211, or in the alternative during any of acts S201 to S2011, in case the torque condition or the velocity condition of a motor/actuator is momentarily violated, internal counting pertaining to monitor engagement or homing condition is reset.

While in some embodiments the engagement process for the roll degree of freedom and the engagement and homing process for the closure joint are independent, in other embodiments, one or more acts of the algorithms of FIGS. 5 and 12 may depend on each other. For example, the successful engagement of the roll degree of freedom may be confirmed before the engagement process for the closure joint is performed (i.e., act S201 and subsequent acts may be performed in response to act S111). In another example, the successful engagement of the roll degree of freedom may be confirmed before the homing process for the closure joint is performed (i.e., act S211 and subsequent acts may be performed in response to successful completion of act S111 and act S209). In another example, the engagement of the closure joint may be confirmed before the engagement process for the roll degree of freedom (i.e., act S101 and subsequent acts is performed in response to the successful completion of act S209). In another example, the homing of the closure joint may be confirmed before the engagement process for the roll degree of freedom (i.e., act S101 and subsequent acts is performed in response to the successful completion of act S213).

Joint Calibration and Control (Roll and Closure)

One or more embodiments for use of a mathematical model including backlash, compliance and kinematics of the jaw mechanism in a combined form during opening and closing phases are described. A control algorithm is presented that incorporates the proposed modeling strategy for position control. In addition, a modeling strategy is described for roll control.

These embodiments calibrate and control a constrained mechanism with backlash and/or stiffness. The term mechanical recoil hysteresis, which may be referred to as "hysteresis" herein, encompasses backlash and compliance. That is hysteresis may be originated from the combined effect of backlash and compliance.

The hysteresis is a comeback or recoil experienced by one component of the device caused by one or more other components of the device. Backlash may be the play between the mechanical interaction of the components caused by a space or gap between the components. Backlash is a characteristic in a mechanical drive system. The stiffness, or compliance, results from the flexibility of the components. Compliance is characterized by deformation or deflection of a component under a load. Either backlash or compliance may be caused by design or manufacturing tolerances of the components. Either backlash or compliance may be measured as a mechanical distance or angle between the components when one component is moved without causing motion in the other component. For example, in the example of meshed gears, a driven gear experiences backlash when there is a space between the meshed teeth with a driving gear, and the driver gear experiences compliance when there is flexibility of the meshed teeth so that there is give between the meshing or meshed teeth.

Either backlash and/or compliance may result from one or more physical characteristics of the surgical tool 240 including an effector 246 (e.g., a surgical instrument for closing clamps or jaw), adjusting the bend of an endoscope, extending an instrument outside of cannula walls, applying pressure using a clamping tool, as well as other movements and actions, and/or one or more physical characteristics of the tool driver 230. When the surgical tool 240 includes a jaw closure 251, a desired clamp force may be provided at its distal end by the jaw. The shape of the jaw may be curved and contain a plastic pad in its inner side so, as the jaw closure 251 closes towards a blade at the end effector, the mechanism deflects and exhibits compliance. The surgical tool 240 may be a harmonic surgical instrument having at least one tool disk 244 coupled to a corresponding motor or actuator with a harmonic drive train for harmonic motion. The harmonic motion may include a blade is longitudinally vibrated by the energy generator during dissection. Circuits and electronics are all located in the very proximal part of the instrument.

In addition, backlash and/or compliance may be a component of the entire (any one or more part) drive stack which is distributed from actuators to the distal end of the surgical tool 240. There exist multiple sources of backlash which accumulate together and lead to an aggregate backlash size (e.g., up to 25 degrees or more). Backlash sources in the drive stack include the motor's gearbox, an instrument-to-tool driver interface, a transmission, an instrument's internal gear mechanism and inner/outer tube mechanism that drives the jaw. One or more other internal mechanisms (inner-tube/outer-tube, pin of the distal closure joint) may contribute to backlash. In addition, the drive stack components such as blade, pad, gear teeth, or others may contribute to compliance.

As a result, from an input-output perspective, the mapping between actuator angle and jaw angle is nonlinear (i.e., actuator angles do not necessary correspond to expected jaw angles using a rigid model of the drive stack). A mapping may be an associated or a pair in a database or matrix such as a lookup table. In addition, mappings may change over time. However, the surgical tool 240 may be a single use device that under the normal duration of time for the single use exhibits negligible variation in the calibration curves over repetitive cycles.

The mappings may differ depending on whether the jaw closure 251 is opening or closing. Thus, a conventional modeling scheme (e.g., using computer aided drawings or CAD to simulate the drive stack) may not suffice. Therefore, to achieve acceptable position tracking performance, the surgical instrument should be calibrated by identifying its input-output relationship that is instrument-specific. The model is utilized to control the device. Due to variation of part tolerances, some embodiments may not include a nominal and generic model for the type of surgical instrument but rather a specific model for each individual instrument to be calibrated and have its own parameters.

Figure 13:
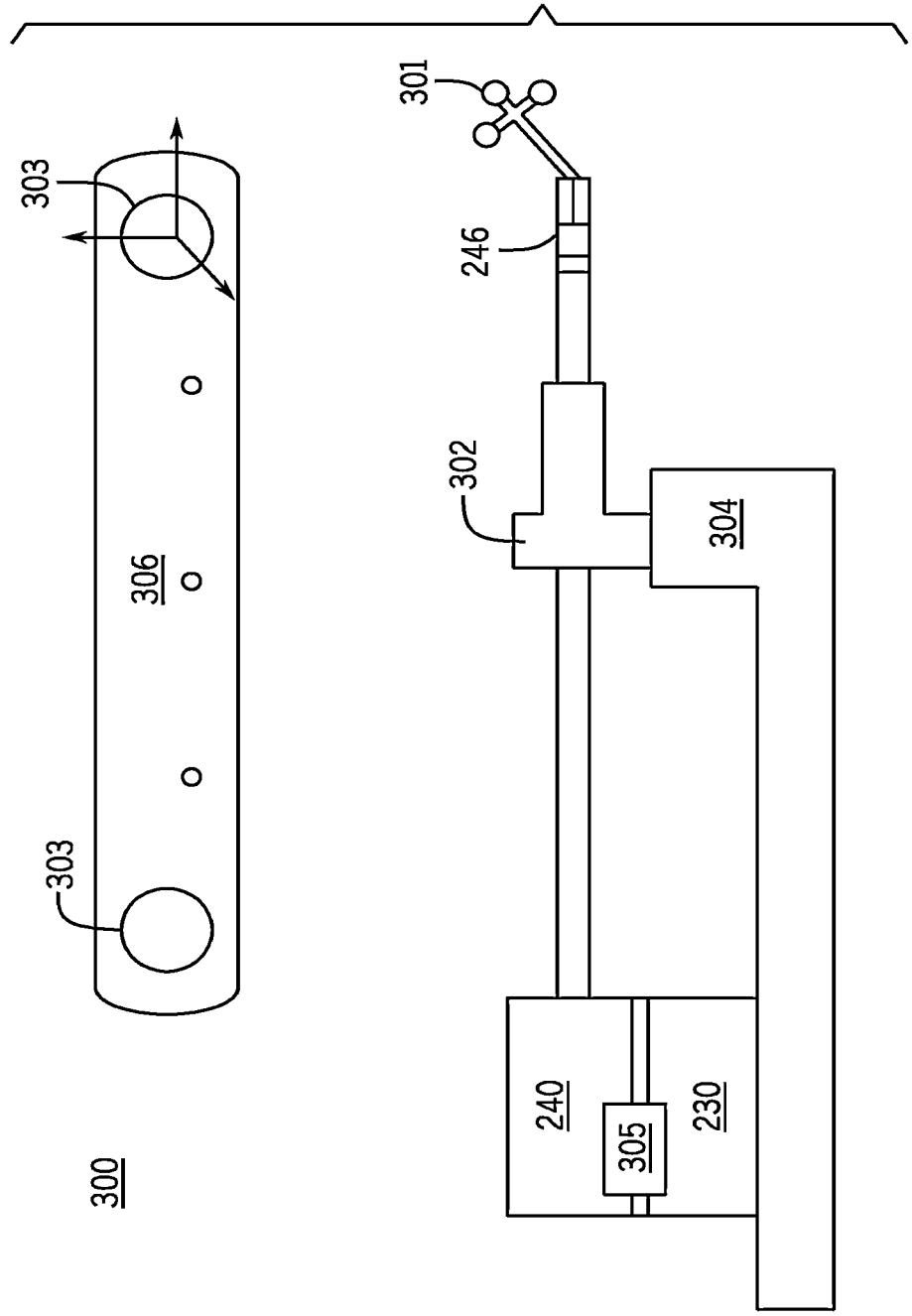
FIG. 13 illustrates an example optical tracking system for the surgical tool.

FIG. 13 illustrates a tracking system for the surgical instrument 240. A frame 304 may support the tool driver 230 coupled to the surgical instrument 240, which is further supported near the distal end by support 302. The end effector 246 of the surgical instrument 240 may be fed through the support 302. Additional, different, or fewer components may be included.

The tracking system includes an internal tracking system 305 and an external tracking system 306. The internal tracking system 305 may include components described earlier, such as an incremental encoder that measures motion at the motor before the transmission gear. The internal tracking system 305 may alternatively measure motion at the actuator, drive disk, etc. The internal tracking system 305 may include one or more of the sensors 236 such as position sensor 343 or optical sensor 347. For each degree of freedom in tool driver system, interaction torque between the drive mechanism and tool interface is measured by the torque sensor 342 in the drive stack. The surgical instrument 240 is also interfaced to three independent drive mechanisms, i.e., actuators, through three disk pairs (e.g., tool disk 244 and drive disk 234 in each pair) with two for closure joint and one for roll joint.

The external tracking system 306 measures motion at the surgical instrument 240. The external tracking system may be mounted at a prescribed distance and orientation from the surgical instrument 240. The external tracking system 306 may include one or more cameras 303 to track the surgical instrument 240. The cameras 303 may collect images of a marker 301 placed on or near the end effector 246 (e.g., on the tip of the jaw closure 251). The marker may include indicia such as a pattern, quick response (QR) code, or barcode that can be easily identified in the images collected by the cameras 303. Example image processing techniques for identification of the pattern in the image may include edge detection, template matching, feature matching, or other techniques. The shape, position, size, and other parameters measured in the images may be used to calculate the real time position and orientation of the end effector 246, which may include the jaw angle. In one example, an optical tracking system which is simpler than an image-based approach. For example, we a specialized marker with a predetermined type and/or geometry, may be registered with respect to the frame of the surgical instrument 240.

The processor 312 as implemented by the control unit 210 may receive data collected by the internal tracking system 305 and the external tracking system 306 in order to calculate or develop a model for the relationship between the motion at the surgical instrument 240 and the motion of the actuator or elsewhere in the drive stack. The model may alternatively be calculated or developed at an external device (e.g., server) in communication with the internal tracking system 305 and the external tracking system 306.

Figure 14:
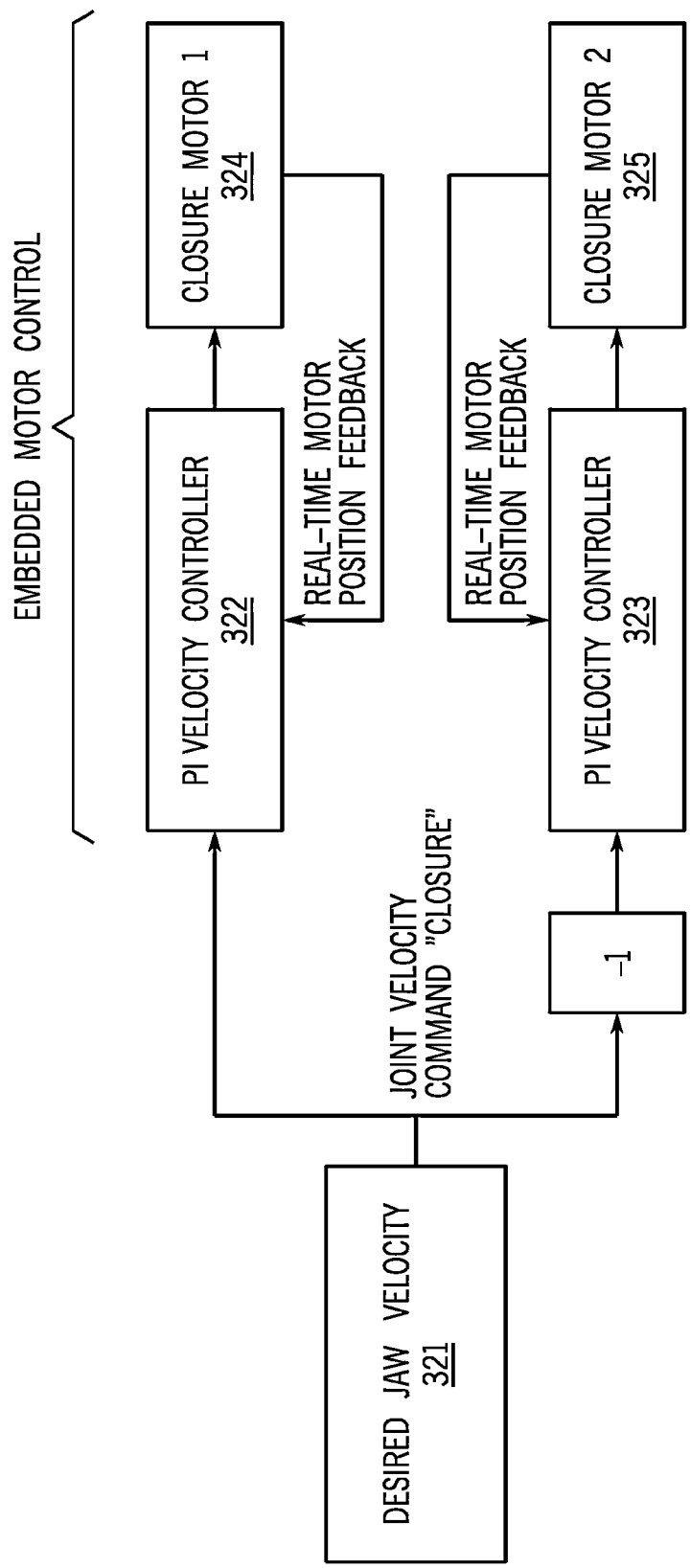
FIG. 14 illustrates an example block diagram of a velocity control mode for calibration.

FIG. 14 illustrates a block diagram of velocity control mode for closure control during calibration. The model for the relationship between the motion at the surgical instrument 240 and the motion of the actuator or elsewhere in the drive stack may include a mapping between actuator angle and jaw angle. In the surgical instrument 240, it may be assumed that two axes which are coupled and drive the jaw mechanism are symmetric. That simplifies the process of calibration to find only the empirical relationship between one of the measured actuator angles and measured jaw angle.

A desired velocity (e.g., jaw velocity 321) is provided to a first PI velocity controller 322 and a second PI velocity controller 323, which may be referred to collectively as velocity controller. The first PI velocity controller 322 and the second PI velocity controller 323 may be implemented by a single device such as control unit 210. The low-level PI control scheme presented in FIG. 7 may also be utilized to implement the velocity controllers 322 and 323 at the embedded-level. Control gains, saturation limits and all other motor control parameters are specified in the configuration settings.

The first PI velocity controller 322 provides commands to a first motor (e.g., first closure joint motor) and receives feedback from the first motor. The second PI velocity controller 323 provides commands to a second motor (e.g., second closure joint motor) and receives feedback from the second motor.

To control the instrument during calibration for development of the model for the relationship between the motion at the surgical instrument 240 and the motion of the actuator, the velocity controller with current saturation is implemented. To this end, a constant velocity is sent to the velocity controller to open the jaw at a fixed rate. Once the jaw fully opens, it hits its internal opening hard stop so it maintains its position as motor current (or torque) is saturated. Depending on the setting of current saturation in embedded velocity controller, the torque value at hardstop location can be adjusted. To maintain safety of the device, the torque is set to be below a threshold. To close the jaw, a negative velocity command is sent through the same control scheme. At fully closed configuration, the jaw hits its internal closing hardstop and motor current (or torque) is saturated at the opposite direction of opening regime. Closing torque threshold is set slightly larger than the opening threshold since jaw requires to overcome compliance of a pad placed in the inner side of the jaw that is pushed against tip blade during closing regime.

Figure 15:
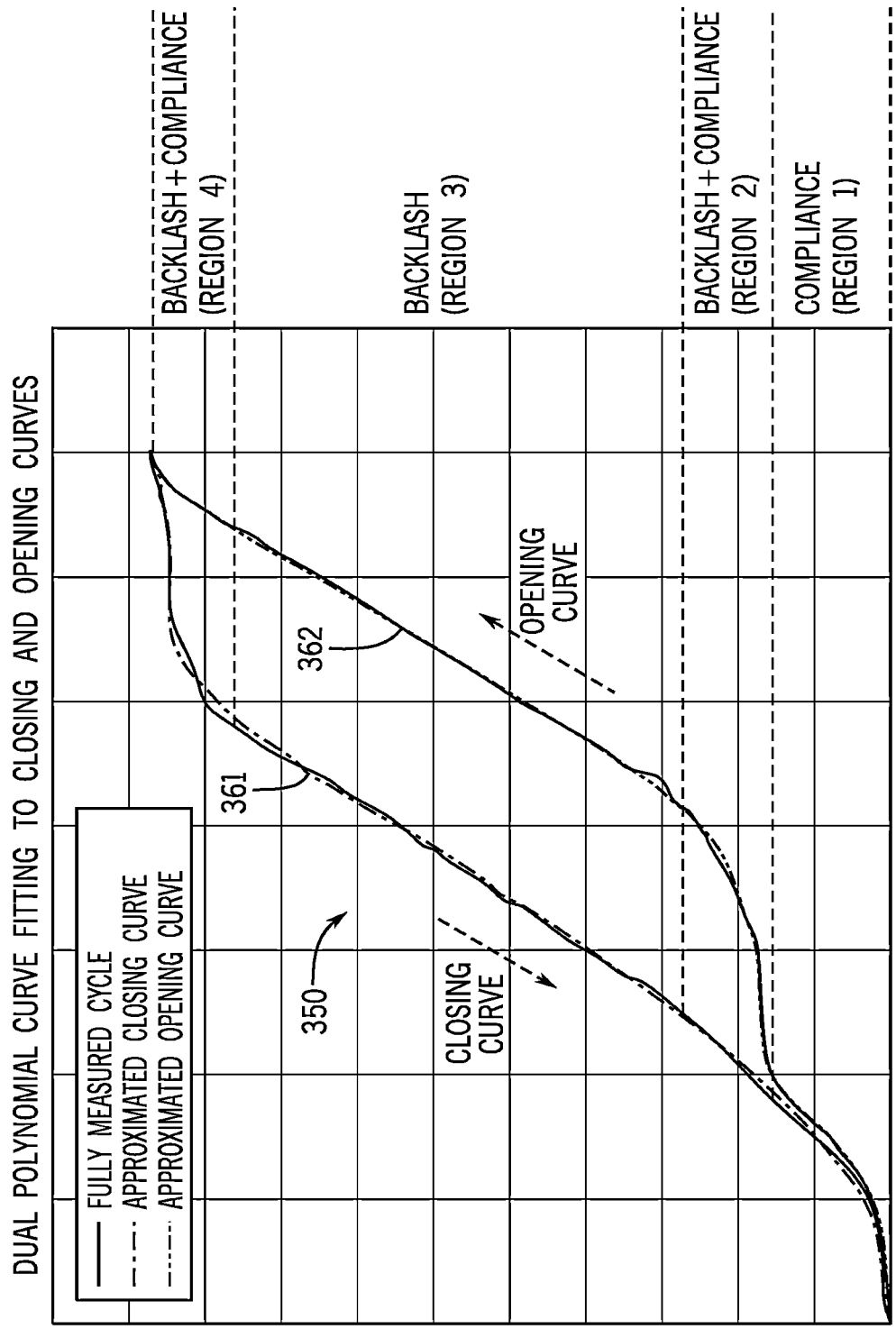
FIG. 15 illustrates a mapping for a closure joint.

FIG. 15 illustrates an example an example model for the relationship between the motion at the surgical instrument 240 and the motion of the actuator. In one example, the relationship is a jaw mapping 350 for the closure angle of the jaw. The jaw mapping 350 may include closing portion 361 for the closing curve when the jaw is closing and an opening portion 362 for the opening curve when the jaw is opening. The input, or horizontal axis, represents the actuator angle measured by the internal tracking device 305, which may include the motor's encoder and/or a gear ratio of the motor driver. The output is the measurement at the end effector 245, such as a jaw orientation angle reported by the external tracking device 306.

As designated by the dotted line in FIG. 15, the jaw mapping 350 has at least four distinct regions or behaviors for the operational relationship between the motor instructions and the measured position. The model for the relationship between the motion at the surgical instrument 240 and the motion of the actuator accounts for these regions or operational relationships, which include at least one compliance relationship in which the source of hysteresis or recoil is substantially from compliance, at least one backlash relationship in which the source of hysteresis or recoil is substantially from backlash, at least one combination relationship in which the source of hysteresis or recoil is from backlash and compliance. Thus, the motion profile of the jaw mapping 350 includes four different regions exhibiting pure compliance (region 1), backlash plus compliance (regions 2 and 4) as well as pure backlash (region 3). In region 1 the only substantial mechanical recoil hysteresis is compliance. In region 3 the only substantial mechanical recoil hysteresis is backlash. In regions 2 and 4, the system experiences substantial backlash and compliance.

A curve fitting approach is applied to the jaw mapping 350 to find one or more functions to the collected data. The functions may be polynomials having a predetermined order or an order calculated by the curve fitting approach. The curve fitting approach may be a least squares technique, regression technique, interpolation technique, or another technique. The curving fitting approach may generate multiple polynomials. In one example, a first polynomial is applied to the closing curve of the jaw mapping 350 and a second polynomial is applied to the opening curve of the jaw mapping. The polynomials are used as inverse kinematics of the end effector 246 closure joint for real-time orientation control.

Figure 16:
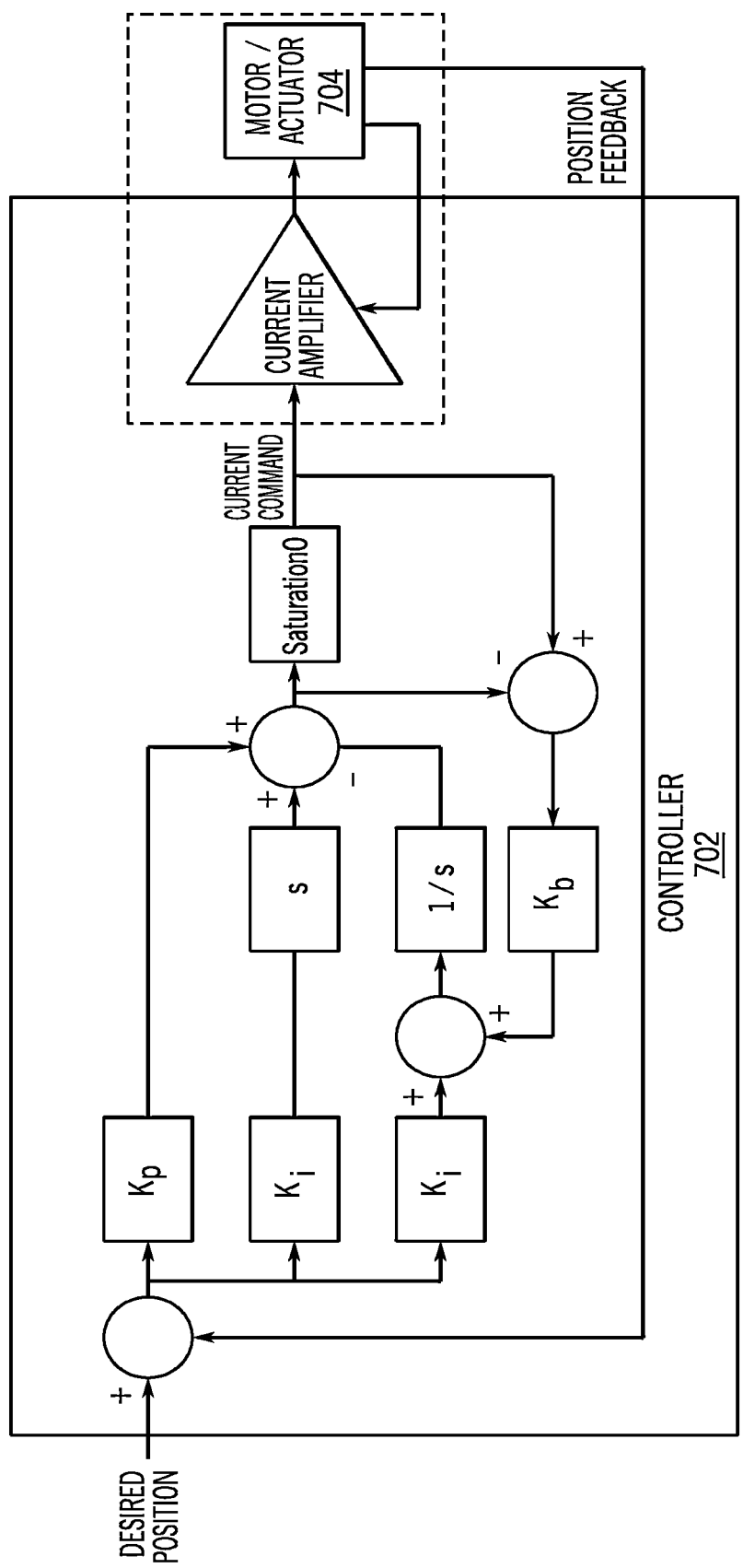
FIG. 16 illustrates an example block diagram for a position control mode.

FIG. 16 illustrates an example block diagram for a position control mode including a feedback loop implemented by a controller 702 for the rotary motor of the tool driver 230 (e.g., the controller 702 may be implemented by the control unit 210 and/or the processor 312). The position control mode may be a PID position controller with anti-windup for both closure motors. In one embodiment, controller 702 is a proportional-integral (PI) controller may be implemented in part as hardware, firmware, software, or a combination thereof.

In this embodiment, the motor is placed in position control mode, and is commanded to be at a position. A position command (e.g., control setpoint) is received by controller 702. The controller 702 provides a loop/feedback mechanism to adjust and provide an appropriate current (e.g., the controller output) to drive motor/actuator 704 at a velocity and direction to the position command/setpoint. In one embodiment, the controller 702 may use various values, such as desired torque to achieve the velocity, current to achieve the velocity, etc. as a measure for generating the controller's current output to motor/actuator 704.

Adjustments are made to the original velocity command, such as proportional adjustment (e.g., block with $k_p$) to adjust the position proportional to an error (e.g., as determined by the feedback) and adjust the position according to a derivative term at block with s, as well as an integral adjustment (e.g., block with 1/s and block with $k_i$) to adjust the position to account for past error integrated over time. The integral adjustment may further be adjusted using a restoring term generated by block $k_b$ which is in feedback loop for anti-windup, to further adjust the value of the integral adjustment. The integral adjusted value output from block 1/s may be added to the proportional setpoint adjusted value).

Figure 17:
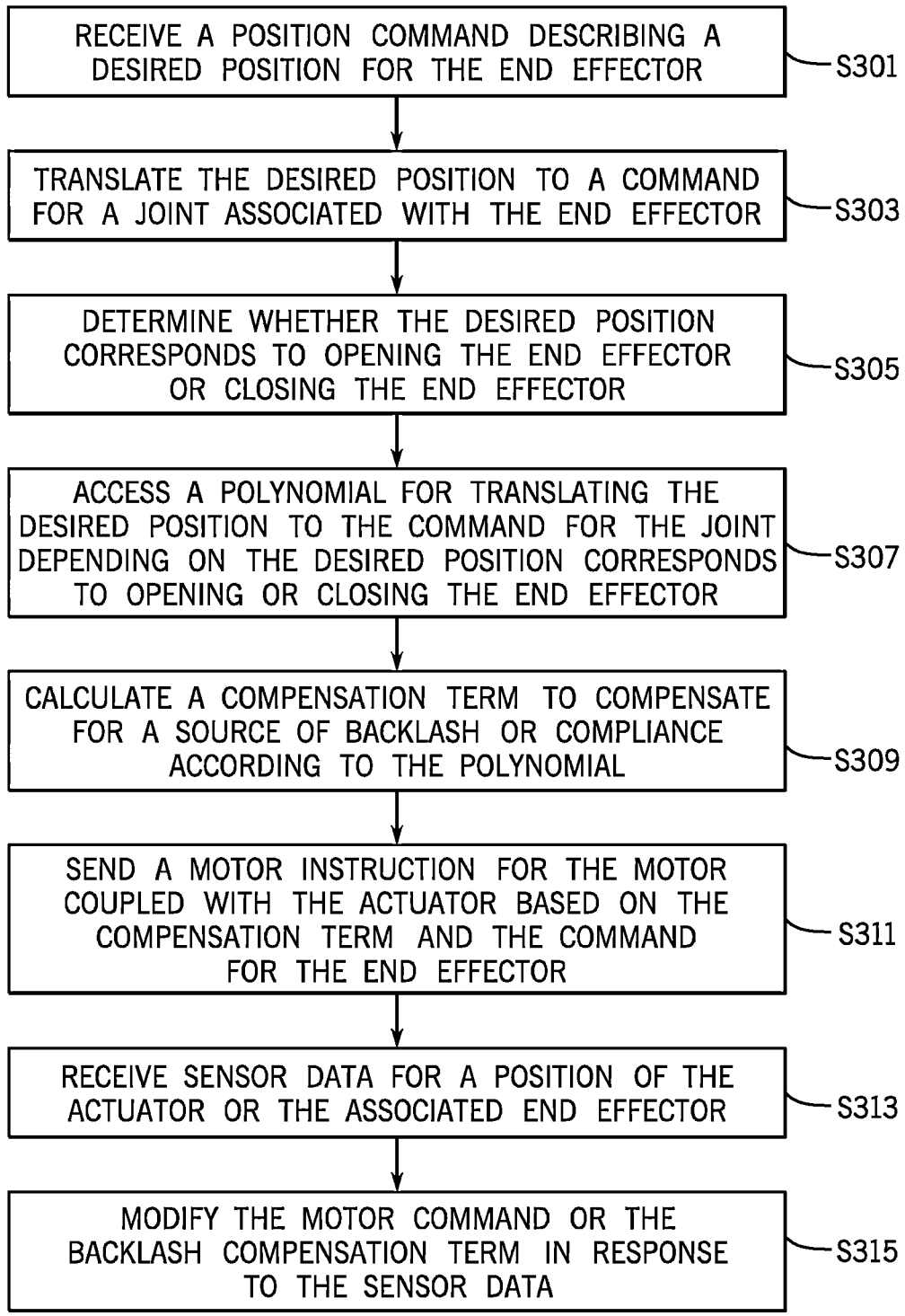
FIG. 17 illustrates an example flow chart for joint control.

FIG. 17 illustrates an example flow chart for one or more algorithms or processes for joint control using a model for the relationship between the motion at the surgical instrument 240 and the motion of the actuator. The process may be performed by a programmed processor (also referred to here as processor or controller), configured according to instructions stored in memory (e.g., the processor 312 and the memory 314 of FIG. 3, where the processor 312 is configured according to the instructions of the tool control 320 and the engagement control 316). Additional, different, or fewer acts than those in FIG. 17 may be performed.

Figure 18:
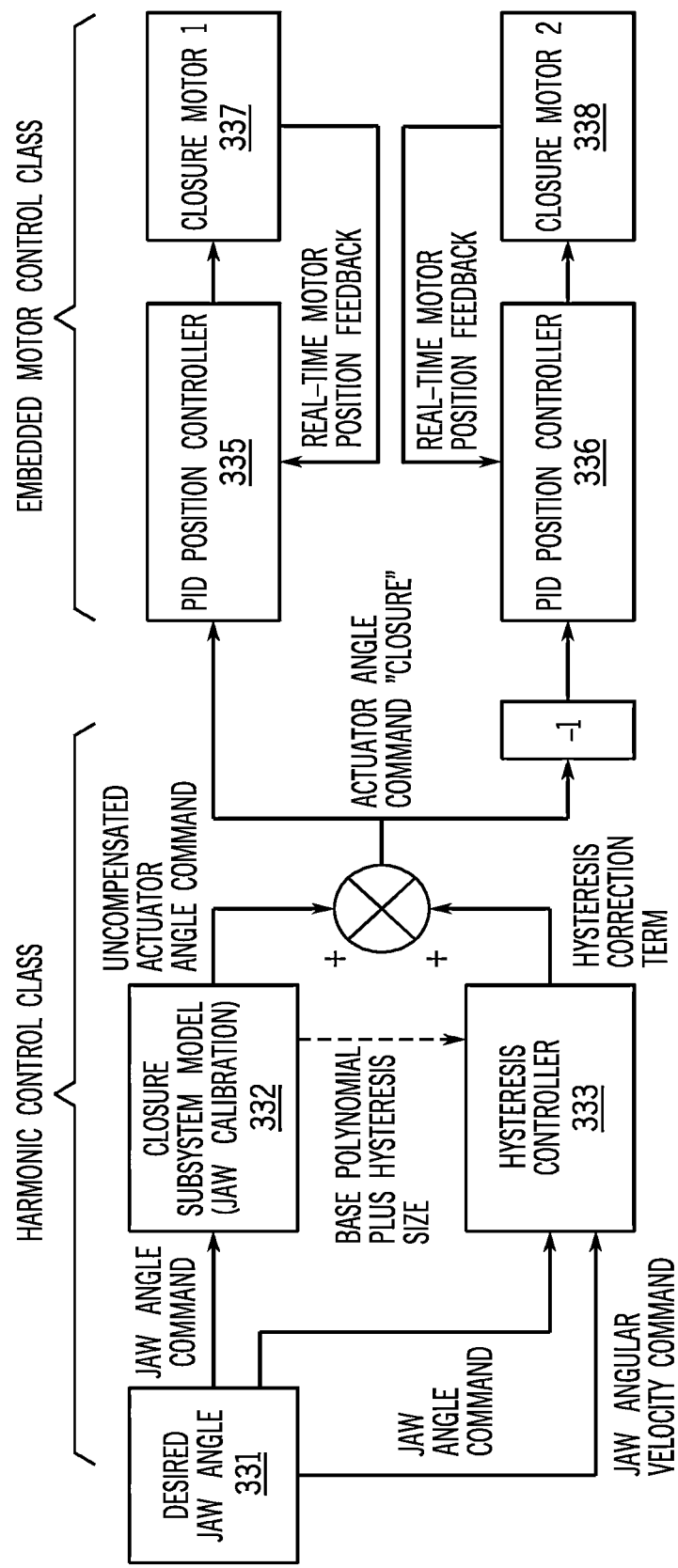
FIG. 18 illustrates an example block diagram for the closure joint control with position tracking.

FIG. 18 illustrates an example block diagram for one implementation of the algorithm of FIG. 17 as applied to the closure joint control with position tracking for implementation. A desired position (e.g., jaw angle 331) is provided to a closure subsystem model 332 and a hysteresis controller 333 (e.g., jaw mapping as described with respect to FIG. 15). The outputs of the closure subsystem model 332 for no recoil (backlash and/or compliance) are combined with the outputs with the hysteresis controller 333 to account for recoil. This result is provided to a first PID position controller 335 and a second PID position controller 336, which may be referred to collectively as position controller. The first PID position controller 335 and the second PID position controller 323 may be implemented by a single device such as control unit 210. The closure subsystem model 332 and the hysteresis controller 333 may also be provided by the control unit 210. Any of these controllers may be referred to as processor 312. The low-level PID control scheme presented in FIG. 16 may also be utilized to implement the position controllers 335 and 336 at the embedded-level. Control gains, saturation limits and all other motor control parameters are specified in the configuration settings.

Thorough real time motor position feedback, first PID position controller 335 and the second PID position controller 323 control the closure motor 337 and the closure motor 338, respectively, to the desired jaw angle 331. The mapping between two actuators and jaw angle is symmetric in the instrument so the same actuator command generated for closure motor 337 by instrument control method is mirrored and is applied to closure motor 338 through the embedded position controller.

At act S301, the processor 312 receives a position command describing a desired position for the end effector. The desired position may be a jaw angle 331. For example, angle α illustrated in FIG. 10B is the desired position. The angle may be measured from the rotational axis of the jaw closure 251. In other examples, when the end effector is another type of device, the desired position may be any degree of freedom for an angle or position of the end effector (e.g., roll angle, yaw angle, pitch angle, x-distance, y-distance, z-distance).

At act S303, the processor 312, via the closure subsystem model 332, translates the desired position to a command for a joint associated with the end effector. The command may be an uncompensated actuator angle command. In the example of the jaw closure 251, the closure subsystem model 332 inputs the jaw angle command and outputs the uncompensated actuator angle for the rotary device associated with the closure joint of the jaw closure 251. The processor 312 may access a lookup table from memory 314 for the uncompensated actuator angle command that matches positions with uncompensated actuator angles.

At act S305, the processor 312 determines whether the desired position corresponds to opening the end effector or closing the end effector. For example, the processor 312 may compare the last stored position or angle from memory 314 and compare the desired angle to the last known position or angle. The processor 312 may subtract the values and determine whether the difference is a positive value, corresponding to opening the end effector, or the difference is a negative value, corresponding to closing the end effector (i.e., positive jaw angular velocity command corresponds to opening while negative velocity causes closing of the jaw). Different sign conventions are possible (e.g., positive values may correspond to opening the end effector and negative values may correspond to closing the end effector). The sign of the difference between the desired angle and the last known angle may be stored as a difference value (e.g., single bit) that indicates opening or closing. Stated another way, the processor 312 may determine whether the desired position corresponds to a clockwise rotation or a counter-clockwise rotation for the joint.

At act S307, the processor 312 (e.g., hysteresis controller 333) accesses the difference value or otherwise determines whether the difference between the desired angle and last known angle is negative or positive, or whether the desired motion is clockwise or counterclockwise, and selects one of the polynomials fit as the model. The processor 312 may access a first polynomial for translating the desired position to the command for the joint when the desired position corresponds to opening the end effector; and access a second polynomial for translating the desired position to the command for the joint when the desired position corresponds to closing the end effector.

At act S309, the processor 312 (e.g., hysteresis controller) calculates a compensation term to compensate for a source of hysteresis for backlash and/or compliance. The compensation term may be selected or calculated by applying the desired angle 331 to the polynomial selected in act S307. In other words, the polynomial may define the compensation term as a function of the desired angle 331. In addition, because the polynomial is selected according to the direction of rotation or difference value, it follows that the compensation term is selected according to whether motion corresponds to clockwise rotation or counter-clockwise rotation and/or whether the difference value is negative or positive.

The uncompensated actuator angle command and the compensation term may be combined to form an actuator angle command. In some examples, the uncompensated actuator angle command is added to the compensation term to calculate the actuator angle command. The actuator angle command is sent to the corresponding rotary device.

At act S311, the processor 312 (e.g., position controller 335 and/or position controller 336) sends a motor command for the motor coupled with the actuator based on the compensation term and the command for the end effector. So depending on the direction of motion, which can be either opening or closing, either the first polynomial is selected that was fit to opening portion 362 to solve the inverse kinematics of the closure joint or the second polynomial is selected that was fit to the closing portion 361 to solve the inverse kinematics of the closure joint. The direction is determined based on the velocity of commanded closure angle.

At act S313, the processor 312 receives sensor data for the position of the actuator. In some examples, after the motor command is sent for the actuator angle command, additional instructions are sent in response to feedback from sensor data from the position sensor 343 that describes the position of the rotary device such as the actuator, motor, drive disk 234 and/or tool disk 244. The feedback may alternatively be provided by another sensor such as torque sensor 342, electrical sensor 345, optical sensor 347, and force sensor 348. For example, the feedback may be provided by a detection of the end effector or jaw closure 251 detected by the optical sensor 347.

At act S315, the processor 312 modifies the motor command for the motor coupled with the actuator in response to the sensor data. For example, the process may be repeated to modify the compensation term in response to the sensor data such that the modified motor command is based on the modified compensation term. The processor 312 may access the models in response to the feedback sensor data, select the polynomial in response to the feedback sensor data, and generate the compensation term. The first PID position controller 335 provides subsequent commands to the first motor (e.g., first closure joint motor 337) and may receive subsequent feedback from the first motor. The second PID position controller 336 provides commands to the second motor (e.g., second closure joint motor 338) and may receive subsequent feedback from the second motor. The feedback loops may repeat substantially indefinitely, which means until interrupted by user action such as powering down the tool driver 230 or the surgical tool 240 or detachment of the surgical tool 240 from the tool driver 230.

Figure 19:
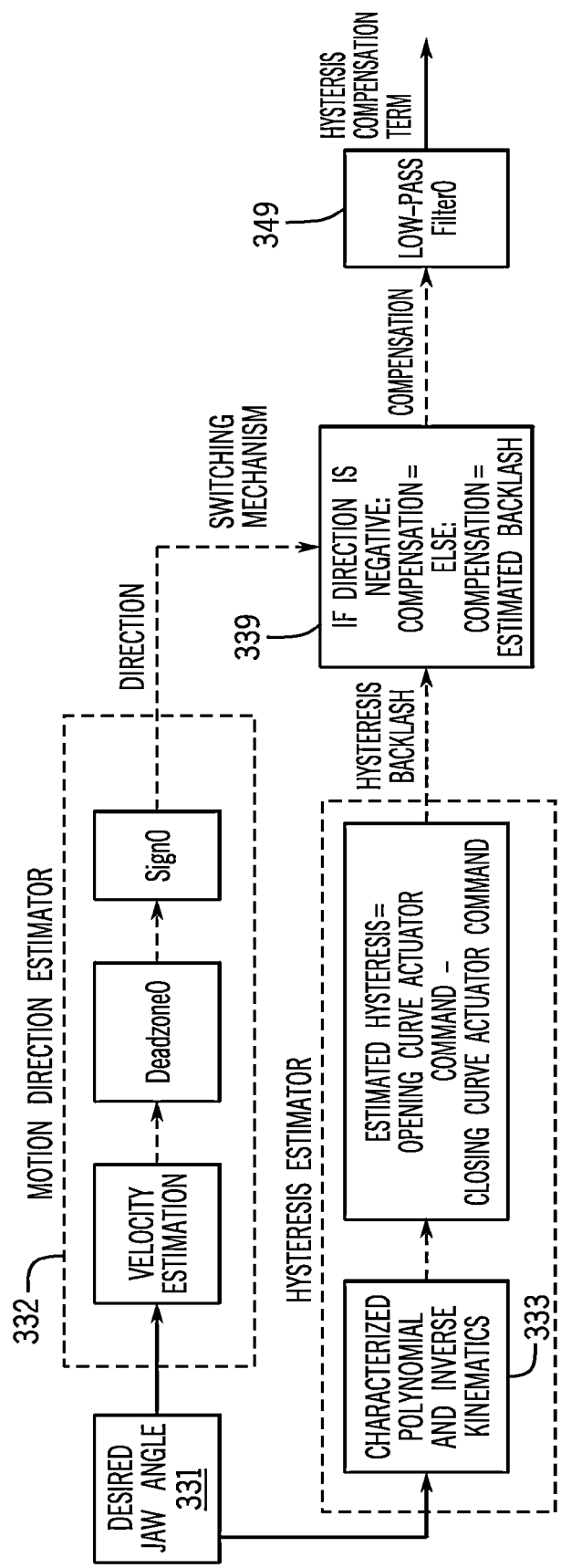
FIG. 19 illustrates an example block diagram for backlash compensation.

FIG. 19 illustrates an example block diagram for backlash/compliance compensation. As an alternative to selection of a different polynomial depending on whether the end effector is opening or closing, the example of FIG. 19 uses the closing curve polynomial as the base. As a result, if commanded jaw velocity is negative (closing regime), the output of hysteresis controller is set to be zero since no compensation is required. However, if motion is in the opposite direction (opening regime), the hysteresis compensation term is calculated as the difference between actuator commands for opening and closing curves for a given jaw angle. This term is added to the base actuator command to generate the compensated command.

The closure subsystem model 332 is illustrated in functional blocks for velocity estimation, deadzone determination, and sign determination. As described previously, velocity estimation is determined from a comparison of the desired jaw angle 331 and the current angle or position (e.g., detected by one or more sensors 236). The deadzone determination may be implemented as a minimum threshold for the velocity estimation. The deadzone determination is used to exclude noise in velocity estimation and detect only actual movement. Therefore, whenever velocity is smaller than a threshold set in the configuration, it is considered as noise so hysteresis controller 333 is not triggered. The sign block represents the determination of rotation direction (positive/negative or clockwise/counterclockwise) as described above.

The hysteresis controller 333 is illustrated in functional blocks to represent the characterized polynomials and inverse kinematics for the model for the relationship between the motion at the surgical instrument 240 and the motion of the actuator, which when provided with the desired jaw angle 331 outputs an estimated hysteresis as the difference between the opening curve actuator command and the closing curve actuator command.

A switching mechanism or direction switch 339 is another function block implemented by the processor 312 to determine whether the direction or the sign indication that the direction is negative or closing. When the direction is negative, no compensation term is used. When the direction is positive (sufficient to overcome the deadzone threshold), the compensation term is the hysteresis compensation term from the difference between the opening curve actuator curve and the closing curve actuator curve of FIG. 15.

A low pass filter 349 is configured to account for the switching nature of this controller that depends on the velocity. The low-pass filter 349 allows smooth and safe transition between two curves as the direction of motion alters.

Figure 20:
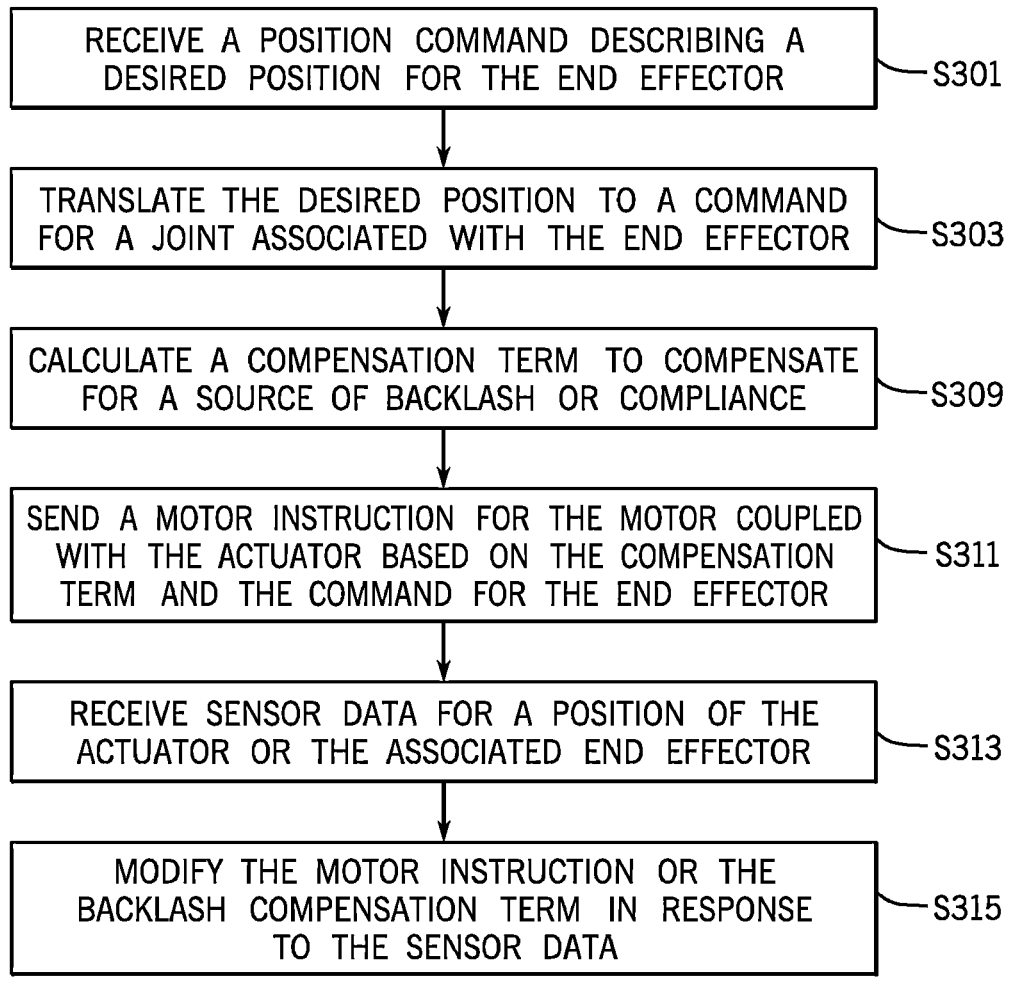
FIG. 20 illustrates an example flow chart for engagement of a closure joint or a roll joint.

FIG. 20 illustrates an example flow chart for one or more algorithms or processes for backlash/compliance compensation for joint control using a model for the relationship between the motion at the surgical instrument 240 and the motion of the actuator. The process may be performed by a programmed processor (also referred to here as processor or controller), configured according to instructions stored in memory (e.g., the processor 312 and the memory 314 of FIG. 3, where the processor 312 is configured according to the instructions of the tool control 320 and the engagement control 316). Additional, different, or fewer acts than those in FIG. 20 may be performed.

FIG. 20 is a simplified flowchart similar to FIG. 17 and similarly labeled acts are performed in substantially the same manner. It should be noted that acts S305 and S307 are not included in FIG. 20. Rather than select polynomials, the embodiment of FIG. 20 calculates a compensation term for backlash and/or compliance.

The example of flowchart may be applied when the joint is a closure joint and the desired position includes a closure angle or when the joint is a roll joint and the desired position includes a roll angle. However, certain aspects may be specific to a roll joint.

Figure 21:
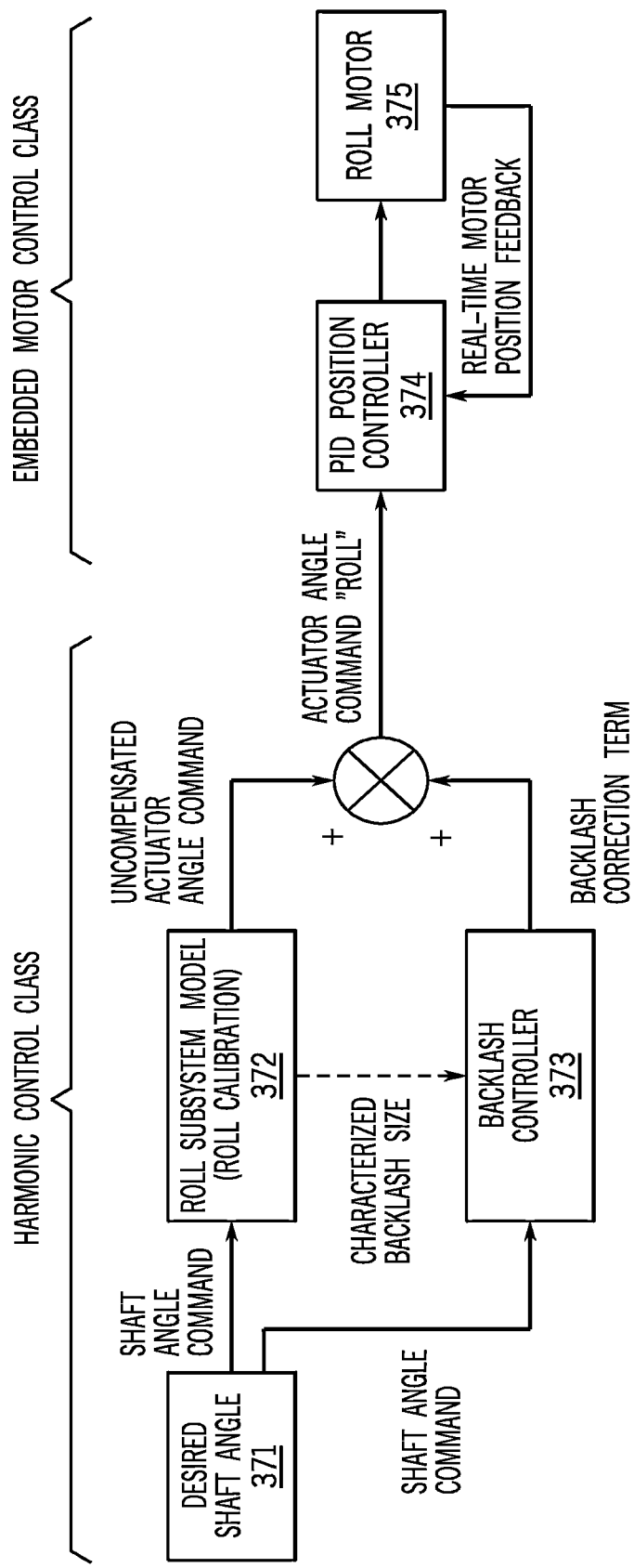
FIG. 21 illustrates an example block diagram for the roll joint with position tracking.

FIG. 21 illustrates an example block diagram for the roll joint with position tracking. The desired shaft angle 371, which may be a roll angle or position for the roll joint, is received at act S301 as a position command describing a desired position for the end effector. The desired shaft angle 371 may be converted by the processor 312 to a shaft angle command or a shaft angular velocity command, which is provided to both the roll subsystem model 372 and the backlash controller 373. The roll subsystem model 372 performs roll calibration to translate the desired position to an uncompensated command for the actuator of the roll joint at act S303.

Act S309 is modified so the processor 312 (e.g., backlash controller 373) calculates the compensation term not based on selection of a polynomial, but rather based on a one-to-one mapping denoting gear ratio plus pure backlash between the angle at the joint and actuator angles. For example, for roll joints, compliance is less dominant in the jaw closure. As a result, clockwise and counterclockwise motion in roll degree of freedom only differ by an offset representing backlash in the drive mechanism and instrument. Therefore, positive and negative regimes are only modeled by a first order polynomial, and the backlash term is defined as the average difference between the two curves across range of motion. At act S311 a motor command for the roll motor 375 based on the compensation term and the shaft angle command (e.g., summation of the compensation term and the shaft angle command).

At act S313, the processor 312 (e.g., PID position controller 374) receives sensor data for the position of the actuator for the roll angle of the end effector. The sensor data is feedback of real time rotary device of roll motor 375 position for the roll angle that is provided to the PID position controller 374. At act S315, the processor 312 (e.g., PID position controller 374) modifies the motor command or the backlash compensation term in response to the sensor data for the roll angle.

Safety Mechanism or Safety Mode (Roll and Closure)

One or more embodiments to enhance the safety of the instrument when it interacts with the environment are described. These embodiments protect the device against overloading and breakage when an estimated force at the distal end or tip of the surgical tool (e.g., tip force) exceeds a limit. A control algorithm is presented that incorporates a virtual trajectory method via admittance control for safe position control. These embodiments may be applied to any degree of freedom for an angle or position of the end effector (e.g., roll angle, yaw angle, pitch angle, x-distance, y-distance, z-distance). The control algorithm may be applied to the roll degree of freedom or the closure degree of freedom.

The following embodiments include admittance control and a virtual trajectory to improve safety. The algorithm may run in real time or near real time to actively adjust joint motion to account for interaction between the instrument and its environment. The term "near real time" may include delays to account for processing data and communication of data between components.

In general, a position controller for a surgical tool is designed with a high stiffness for accurate tracking of planned trajectories. However, such a scheme may be potentially dangerous once the instrument collides with an unknown or undesired environment. An undesired environment can be any location except the designated location for a surgical operation such as cutting, grasping, poking, or emitting energy.

The following embodiments improve safety of the interaction between the surgical tool and its environment using torque sensing to shape the interaction. Mechanical interaction is essential for robotic manipulation. The general approach here termed interaction control refers to active regulation of the system's dynamic behavior as impact with the environment occurs. Interaction dynamics can be characterized by mechanical impedance, which may be a dynamic extension of stiffness. The mechanical impedance may alternatively be a degree of resistance to motion that the portion of the tool provides when subjected to a harmonic force. The inverse of mechanical impedance is called admittance.

In addition, a pass/fail safety check is added to the closure control scheme to avoid a potentially hazardous performance scenario. In this case, if such a failure is detected, the control unit 210 designates a hold mode and operation stops for the surgical tool 240 and tool driver 230. This addresses safety concerns and protects the instrument against overloading. Calibrating the instrument, the inverse of the mapping, is utilized as inverse kinematics of the instrument to convert a desired joint angle to the corresponding commanded actuator angles. The underlying control scheme is a PID position control, and the same calculated command is concurrently sent to two driving motors. In addition, symmetricity of closure drive mechanism is evaluated in real-time to stop asymmetric motion, in case it is detected. The Jacobian of forward kinematics is used to calculate joint torque (defined at the distal side) from motor torque (measured at the proximal side). Knowing the geometry of the instrument, joint torque is converted to joint force at the tip of jaw and is utilized to generate a virtual trajectory employed in overload protection algorithm.

A system with infinite impedance or zero admittance implies no motion in response to any applied force. In other words, it generates a motion command and the controller aims to reach the command that is unaffected by environmental force. Such a pure position control scheme maximizes tracking performance; however, safety concerns may arise. Therefore, an outer control loop is added to modify the inner loop motion command, and make instrument interaction compliant in response to environmental loads. The modified movement is called virtual trajectory since it does not have to be a physically realizable trajectory.

Admittance control to improve joint control safety may involve a desired command $X_d$ and an internal command $X_r$, which may be referred to a virtual command. The X variables may refer to Cartesian-space quantities (e.g., joint values either commands or measurements). The desired command and the internal command correspond to the same degree of freedom. The desired command and the internal command may correspond to the closure joint or the roll joint. This control scheme modifies the outer loop desired command $X_d$ through impedance parameters, and creates an internal command $X_r$.

The virtual command may be described as virtual because it does not have to be a physically realizable trajectory. The virtual command is applied to the system, but not directly measurable. The virtual command indirectly shapes the desired impedance (or admittance) which is the target of the control system.

Equation 1 demonstrates a control law that estimates a tip force or interaction force $F_{interaction}$ based on the geometry and torque measurement for the surgical instrument 240, which may be described by a plurality of constants (tuning values or gain values for impedance parameters) including $K_m$, $K_b$ and $K_p$. The impedance parameters may be stored in a configuration file in memory 314 or elsewhere. The selection of the tuning values impacts the performance of the control system. For example, if Km is too small, initial acceleration during impact will be large. If Kp is too large, the interaction may be very rigid and not help to improve safety. Also, if step response is very slow, recovery and catch-up may not be fast, which is not desirable by user.

$$K_m(X_d''-X_r'')+K_b(X_d'-X_r')+K_p(X_d-X_r)=F_{interaction} \quad \text{Eq. 1}$$

Figure 22:
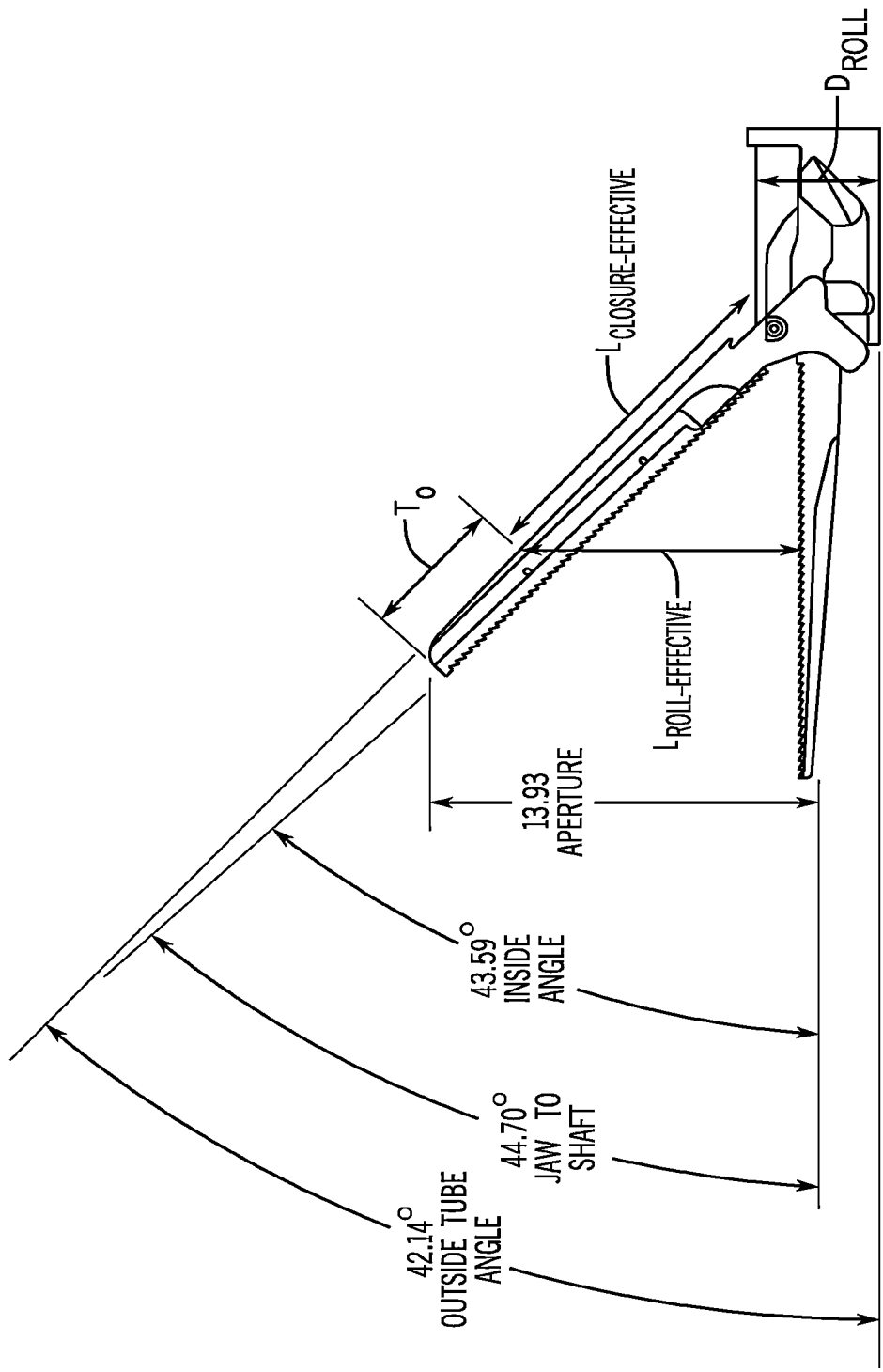
FIG. 22 illustrates an example closure end effector.

Equations 2 and 3 demonstrate tip force as a function of effective length of the joint and joint torque. Equation 2 demonstrates a relationship between tip force $F_{closure-tip}$, the effective geometry (e.g., length) of the closure joint $L_{closure-effective}$ and closure joint torque $\tau_{closure-joint}$. The effective length of the closure joint $L_{closure-effective}$ represents the effective length of the jaw with respect to its pivot point. FIG. 22 illustrates an example jaw closure 251 with effective length for the closure joint, as well as the roll joint described below.

$$F_{closure-tip}=L_{closure-effective} \times \tau_{closure-joint} \quad \text{Eq. 2}$$

Thus, Equation 3 applies the control law of Equation 1 to the closure joint with a single dot in the superscript represents a first derivative such that $X_d'$ is the first derivative of $X_d$, for example, and two dots in the superscript representing a second derivative such that $X_d''$ is the second derivative of $X_d$, for example.

$$K_{in}(X_d''-X_r'')+K_b(X_d'-X_r')+K_p(X_d-X_r)=F_{closure-tip} \quad \text{Eq. 3}$$

The joint torque (for the closure joint, roll joint, or another joint) may be calculated using motor torque described by sensor data from one or more sensors 236. For example, sensor data from the torque sensor 342 integrated in the drive stack may describe torque on any rotary device such as the motor, the actuator, the drive disk 234, and/or the tool disk 244.

As described by Equation 4, the closure joint torque may be calculated using an inverse Jacobian of forward kinematics evaluated at a given actuator angle ($\theta_{closure-motor}$) However, to avoid singularity and improve numerical performance, the Jacobian of inverse kinematics ($J_{closure-IK}$) may be selected to map motor torque ($\tau_{closure-motor}$) to joint torque. A feed forward technique may be used for the desired closure joint angle command ($X_{closure-desired}$) to update the Jacobian instead of the internally modified trajectory, as described by Equation 5.

$$\tau_{closure-joint}=J_{closure-FK}^{-1}(\theta_{closure-motor}) \times \tau_{closure-motor} \quad \text{Eq. 4}$$

$$\tau_{closure-joint}=J_{closure-IK}(X_{closure-desired}) \times \tau_{closure-motor} \quad \text{Eq. 5}$$

Using the Laplace operator and replacing $X_{closure-desired}$ with $X_d$ to represent a general case, the Laplace-transformed interaction control equation is expressed as described in Equation 6:

$$X_r(s) = X_d(s) - \frac{F_{closure-tip}(s)}{K_m s^2 + K_b s + K_p} \quad \text{Eq. 6}$$

Overload protection may be applied only to the opening side of the closure joint. During closing, it not desirable to limit force because such as limit may impact clamping performance. For this reasons, overload protection may be applied to only one side of the closure joint. In addition, overload protection is activated when estimated tip force exceeds a tip force threshold $F_{closure-threshold}$ defined by a setting or configuration file (e.g., stored in memory 314). On the other hand, when the jaw is commanded to close, the overload protection may be disabled to ensure that maximum desired clamp force is achieved by the surgical instrument 240. As described in more detail below, a compensation term may be calculated for overload protection for the motor when the tip force exceeds the tip force threshold or other thresholds established by these relationships.

Another approach is also applicable to roll degree of freedom for compliance control. One difference is the calculation of the interaction force. In this case, tip force ($F_{roll\text{-}tip}$) is in the direction of twisting the shaft and is estimated using Equations 7 and 8:

$$F_{roll\text{-}tip} = L_{roll\text{-}effective} \times \tau_{roll\text{-}joint} \qquad \text{Eq. 7}$$

where $L_{roll\text{-}effective}$ is calculated as $$L_{closure\text{-}effective} \times \sin(X_{closure\text{-}desired}) + \frac{D_{roll}}{2} \qquad \text{Eq. 8}$$

where $D_{roll}$ is shaft's diameter. Saturation is also defined double-sided for roll degree of freedom.

The overload protection may be performed in a safety mode implemented by the surgical instrument 240 and the tool driver 230. The safety mode may contrast with a normal mode in which overload protection is not applied. That is, these embodiments may be applied only at certain times, when safety mode has been enabled. The safety mode may also be activated at all times or may be activated based on a safety event. The safety event may be a default setting the first time the surgical instrument 240 is turned on but may be subsequently deactivated by the user. The safety event may occur when a certain procedure is selected by the user. The safety event may occur when a specific task such as cutting, grasping, poking, or energy emission is selected by the user. The safety may occur based on a characteristic of the patient such as age (e.g., infants or elderly patients may have a higher risk), weight, height, or medical conditions.

Figure 23:
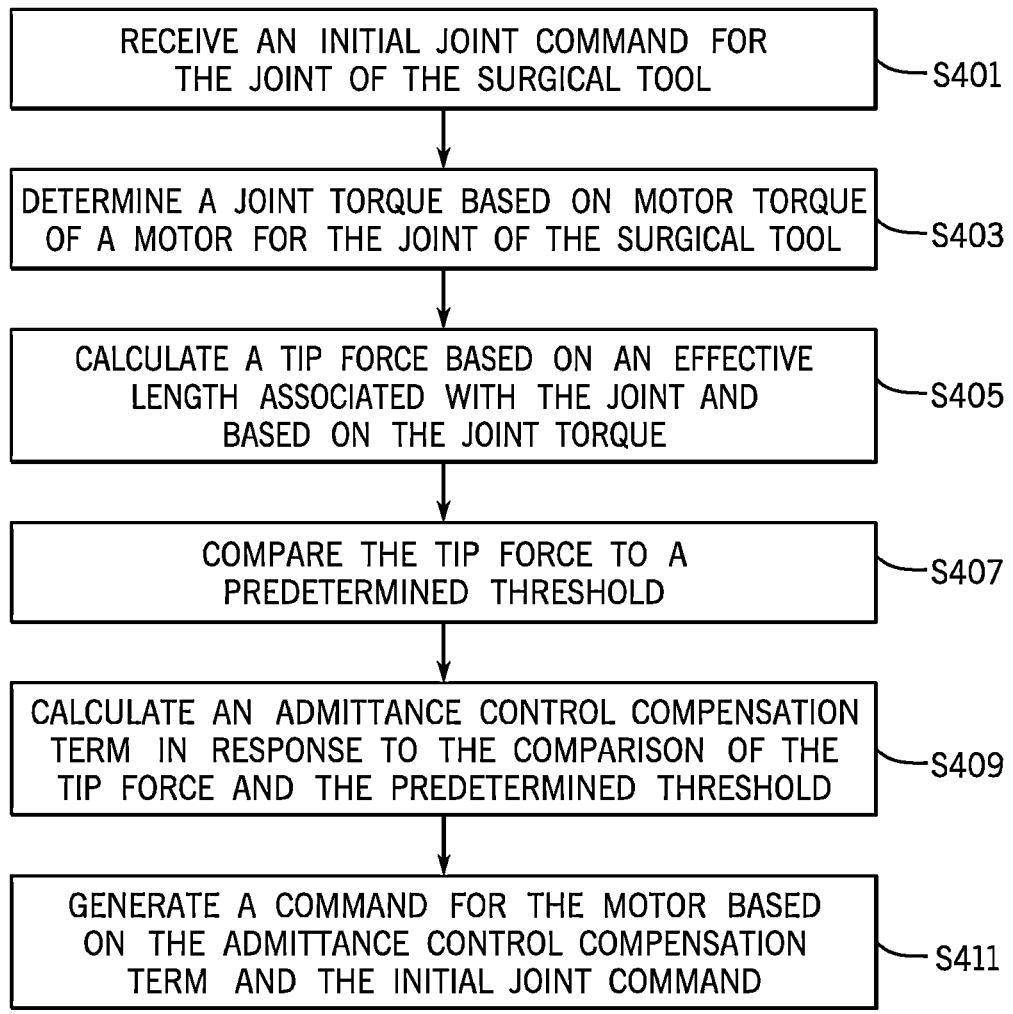
FIG. 23 illustrates an example flow chart for a safety mode of a surgical tool.

FIG. 23 illustrates an example flow chart for a safety mode of a surgical tool. The process may be performed by a programmed processor (also referred to here as processor 312), configured according to instructions stored in memory 314 and executed by the processor 312 of FIG. 3, where the processor 312 is configured according to the instructions of the tool control 320 and the engagement control 316. Additional, different, or fewer acts than those in FIG. 23 may be performed.

Figure 24:
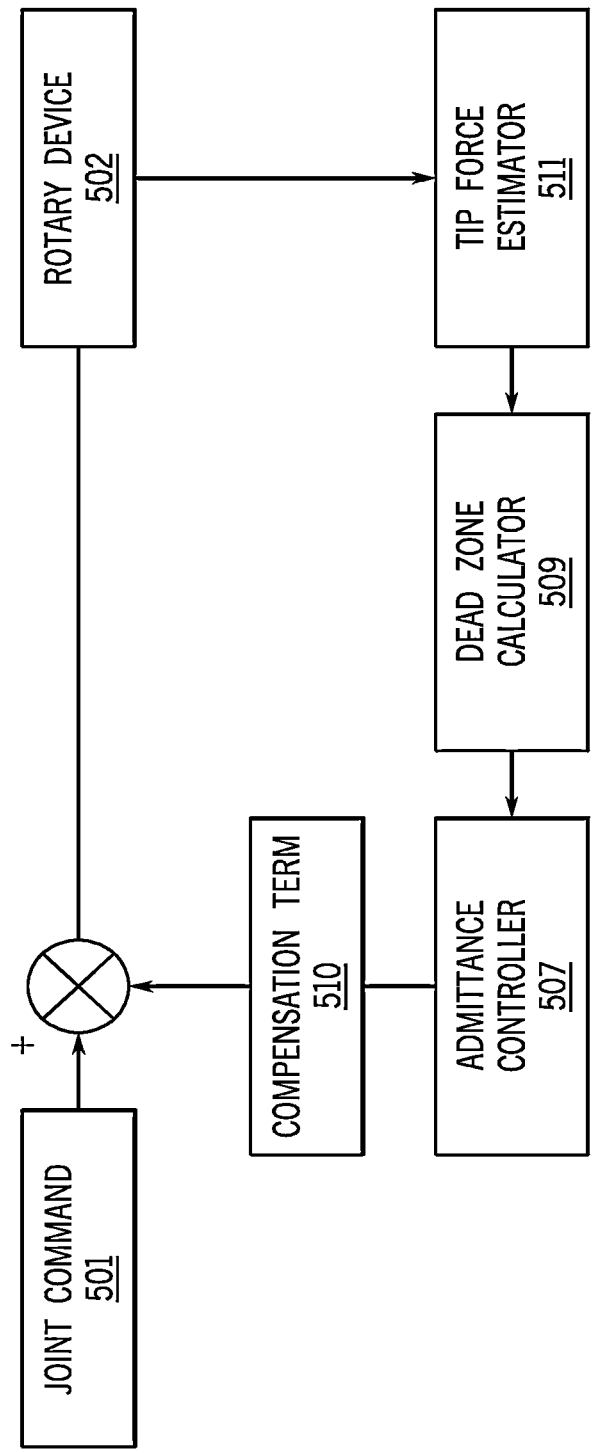
FIG. 24 illustrates an example block diagram for the safety mode.

The acts of FIG. 23 are described below with respect to the system of FIG. 24. FIG. 24 illustrates an example block diagram for the safety mode. The control system has an input for a joint command 501 that is combined with a compensation term 510 and provided to a rotary device 502. A outer feedback loop includes a tip force estimator 511, a dead zone calculator 509, and an admittance controller 507. Additional, different, or fewer components may be included.

At act S401, the processor 312 receives an initial joint command 501 for the joint of the tool. The joint command 501 may describe a desired position or angle for one or more degrees of freedom of the surgical instrument 240. In the case of one example a two degree of freedom surgical instrument 240, the joint command 501 may specify a roll angle and/or a closure angle.

At act S403, the processor 312 may determine a joint torque based on operation of the rotary device 502 (e.g., motor torque of the motor). The joint torque may be values filtered or otherwise sampled from sensor data from the torque sensor 342 or another sensor that measures the operation of a rotary device such as the motor, the actuator, the drive disk 234, and/or the tool disk 244.

At act S405, the processor 312 (e.g., the tip force estimator 511) calculates a tip force based on an effective geometry or effective length associated with the joint and based on the joint torque. Referring to FIG. 22, the effective length of the joint represents the length between an effective or representative distal end of the portion of the tool corresponding to the joint and the joint itself. For example, in the jaw closure 251, the effective geometry of the roll joint $L_{roll\text{-}effective}$ corresponds to a first distance or radius for the roll (e.g., in a first dimension or axis) and the effective length of the closure joint $L_{closure\text{-}effective}$ corresponds to the effective length for the closure joint (e.g., in a second dimension or axis). In addition, the $L_{closure\text{-}effective}$ may be defined using an offset $T_o$ with respect to the tip. The reason for the offset may be that the clamp force may be regulated not necessarily at the tip, but at a distance from the tip. The offset distance may be stored in a configuration file in memory 314 or elsewhere. The offset distance may be variable, predetermined, and/or defined according to a user input, a characteristic of the tool driver 230, and/or a characteristic of the surgical tool 240, and may be retrieved from a lookup table based on any of the attributes or identifiers described herein.

At act S407, the processor 312 compares the tip force to a predetermined tip force threshold. The predetermined tip force threshold is the force beyond which the overload protection is activated. The predetermined tip force threshold may be calculated by the processor 312 based on feedback from the operation of the surgical tool 240. The predetermined tip force threshold may be determined according to a user input, a characteristic of the tool driver 230, and/or a characteristic of the surgical tool 240, and may be retrieved from a lookup table based on any of the attributes or identifiers described herein.

The processor 312 (e.g., dead zone calculator 509) may calculate a tip force saturation value $F_{closure\text{-}sat}$ using a dead-zone operator according to a comparison of the tip force $F_{closure\text{-}tip}$ and the predetermined tip force threshold $F_{closure\text{-}threshold}$ as described by Equations 9 and 10.

$$\text{if } F_{closure\text{-}tip} \geq F_{closure\text{-}threshold} : F_{closure\text{-}sat} = F_{closure\text{-}tip} - F_{closure\text{-}threshold} \qquad \text{Eq. 9}$$

$$\text{if } F_{closure\text{-}tip} < F_{closure\text{-}threshold} : F_{closure\text{-}sat} = 0 \qquad \text{Eq. 10}$$

Thus, tip force saturation value $F_{closure\text{-}sat}$ is calculated as the difference between the tip force $F_{closure\text{-}tip}$ and the predetermined tip force threshold $F_{closure\text{-}threshold}$ when the tip force $F_{closure\text{-}tip}$ exceeds the tip force threshold $F_{closure\text{-}threshold}$. In response, the tip force saturation value $F_{closure\text{-}sat}$ is passed to the admittance controller 507 specified by ($K_m$, $K_b$, $K_p$) impedance parameters for subsequent determination of the admittance control compensation term 510. Also, the tip force saturation value $F_{closure\text{-}sat}$ is calculated zero (or omitted) when the tip force $F_{closure\text{-}tip}$ is less than the tip force threshold $F_{closure\text{-}threshold}$. In response, the tip force saturation value $F_{closure\text{-}sat}$ of zero is passed to the admittance controller 507, or no tip force saturation value $F_{closure\text{-}sat}$ is passed to the admittance controller 507.

For the roll degree of freedom, the processor 312 (e.g., dead zone calculator 509) calculates a tip force saturation value $F_{roll\text{-}tip}$ using a dead-zone operator according to Equations 11, 12 and 13.

$$F_{roll\text{-}tip} \geq F_{roll\text{-}threshold} : F_{roll\text{-}sat} = F_{roll\text{-}tip} - F_{roll\text{-}threshold} \qquad \text{Eq. 11}$$

$$F_{roll\text{-}tip} \leq -F_{roll\text{-}threshold} : F_{roll\text{-}sat} = F_{roll\text{-}threshold} + F_{roll\text{-}tip} \qquad \text{Eq. 12}$$

$$\text{if } |F_{roll\text{-}tip}| < F_{roll\text{-}threshold} : F_{roll\text{-}sat} = 0 \qquad \text{Eq. 13}$$

In this example, for the roll degree of freedom, the $F_{roll-threshold}$ is the force threshold beyond which overload protection is activated. $F_{roll-sat}$ is subsequently passed to the admittance controller 507. In one example, tip force saturation value $F_{roll-sat}$ is calculated as the difference between the tip force $F_{roll-tip}$ and the predetermined tip force threshold $F_{roll-threshold}$ when the tip force $F_{roll-tip}$ exceeds (alternatively, greater than or equal to) the tip force threshold $F_{roll-threshold}$ The tip force saturation value $F_{roll-sat}$ is calculated as the summation of the tip force $F_{roll-tip}$ and the predetermined tip force threshold $F_{roll-threshold}$ when the tip force $F_{roll-tip}$ is less than (alternatively, less than or equal to) the negative value, or opposite direction, tip force threshold $-F_{roll-threshold}$. In response to either of these conditions in Equations 11 and 12, the tip force saturation value $F_{roll-sat}$ is passed to the admittance controller 507 specified by ($K_m$, $K_b$, $K_p$) impedance parameters for subsequent determination of the admittance control compensation term 510.

Turning to Equation 13, the tip force saturation value $F_{roll-sat}$ is zero (or omitted) when the absolute value of the tip force $F_{roll-tip}$ is less than the tip force threshold $F_{roll-threshold}$. In response, the tip force saturation value $F_{roll-sat}$ of zero is passed to the admittance controller 507, or no tip force saturation value $F_{roll-sat}$ is passed to the admittance controller 507.

In the example of a closure joint, the dead zone calculator 509 is a one sided calculator and the dead zone operator is a one sided dead zone operator, as shown by the two conditions in Equations 9 and 10. In the example of a roll joint, the end zone calculator 509 is a double sided calculator and the dead zone operator is a double sided dead zone operator, as shown by the three conditions in Equations 11, 12, and 13.

At act S409, the processor 312 (e.g., admittance controller 507) calculates the admittance control compensation term 510 in response to the tip force exceeding the predetermined threshold. The admittance controller 507 may receive the impedance parameters specified by ($K_m$, $K_b$, $K_p$) impedance parameters to calculate the admittance control compensation term 510 based on the tip force saturation value $F_{sat}$ according to Equation 14, which may be applied to any degree of freedom (e.g., the closure joint and the tip force saturation value $F_{closure-sat}$ or the roll joint tip and the force saturation value $F_{roll-sat}$) The admittance control compensation term 510 may be an adjustment to a subsequent joint command and may be calculated as the difference between the virtual joint command and the initial joint command 501 received command at act S401.

$$X_r(s) = X_d(s) - \frac{F_{closure-sat}(s)}{K_m s^2 + K_b s + K_p} \quad \text{Eq. 15}$$

At act S411, the processor 312 generates a command for the rotary device 502 (e.g., motor) based on the admittance control compensation term and the initial joint command 501. The command may provide a position instruction, angle instruction, or velocity instruction for the motor, actuator 238, drive disk 234, or tool disk 244, for any degree of freedom of the surgical instrument 240 (e.g., roll angle, yaw angle, pitch angle, x-distance, y-distance, z-distance). For example, the following detailed example is applied to the closure joint.

Figure 25:
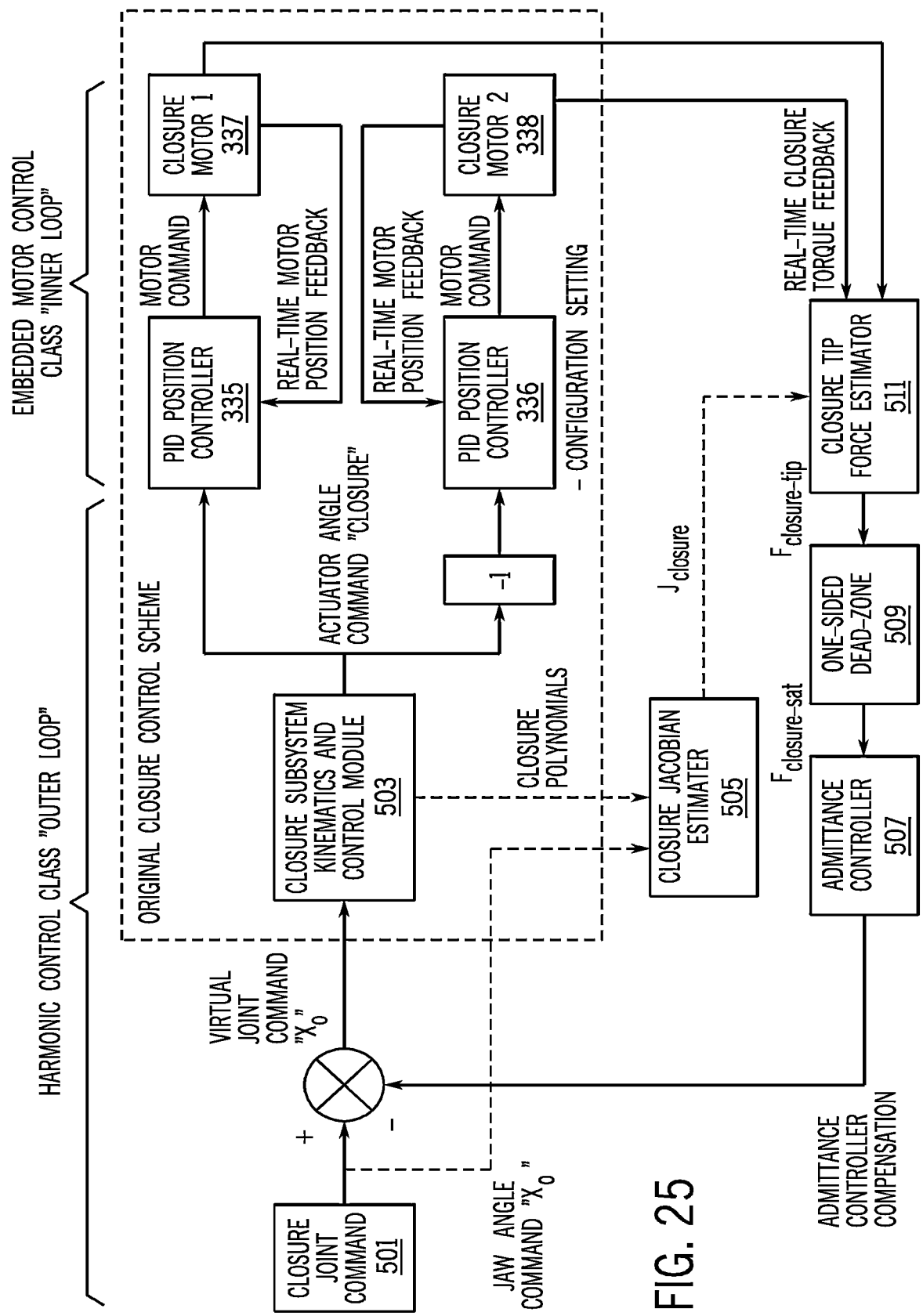
FIG. 25 illustrates is an example block diagram of a two-layer control scheme for safe closure joint control

FIG. 25 illustrates is an example block diagram of a two-layer control scheme for safe closure joint control including the overload mechanism described in FIGS. 22 and 23. The block diagram includes a harmonic control class or outer loop and an embedded motor control class or inner loop. The modified command ($X_r$), called a virtual trajectory, is applied to closure joint control algorithm (e.g., as described herein with respect to at least FIGS. 17 and 18) to calculate actuator commands via the outer control loop. In the inner loop, the underlying control algorithm is a PID position controller at the embedded level used for both closure motors.

The closure joint command 501 is provided to the closure subsystem kinematics and control system module 503, which calculates one or more closure polynomials. The closure polynomials may be the polynomials for the curve fitting approach described herein. The Jacobian curve may be obtained by taking the first derivative of the polynomials.

The closure Jacobian estimator 505 calculates the tip force saturation value $F_{closure-sat}$ and the Jacobian of inverse kinematics value $J_{closure-FK}^{-1}$ $$\tau_{closure-joint} = J_{closure-FK}^{-1}(\theta_{closure-motor}) \times \tau_{closure-motor} = \quad \text{Eq. 16}$$
$$J_{closure-IK}(X_{closure-desired}) \times \tau_{closure-motor}$$

Through replacing $X_{closure-desired}$ with $X_d$ to make equations more generic, the Laplace-transformed interaction control equation such as described in Equations 6 and 15. The Jacobian value $J_{closure}$ is provided to the closure tip force estimator 511. As described above, to calculate the closure tip force, estimator 511 calculates the tip force $F_{closure-tip}$ based on an effective length of the closure joint and torque values for the closure joint. The one-sided dead zone 509 calculates the tip force saturation value $F_{closure-sat}$ according to Equations 9 and 10. The admittance filter calculates the admittance controller compensation for the closure joint as a function of impedance parameters and the $F_{closure-sat}$ value (e.g., using the Laplace-transformed interaction control equation such as Equations 15).

In addition, the closure subsystem kinematics and control system module 503 provides an input for the actuator angle command to the first PID position controller 335 and the second PID position controller 336 to control the closure motor 337 and the closure motor 338, respectively, to the actuator angle, which is the angle in the closure joint command 501 modified by the admittance controller compensation.

According to the closure control method, the coupled constraint mechanism may be assumed to be symmetric so the same control law is applied to both actuators associated with the same degree of freedom (e.g., closure joint). However, due to tolerances between mechanical components in two drive stacks as well as variation in dynamic effects such as frictional forces, two driving axes undergo different torques during operation. For example, as an extreme case, one actuator can be blocked due to excessive friction in its internal gear train while the second one can freely move.

Therefore, one important metric which may be checked (e.g., in real-time) is torque symmetricity and position symmetricity between two axes. The processor 312 may determine or identify a torque value for two associated actuators or other rotary devices (e.g., from a first torque sensor and a second torque sensor) and determine the difference between the torque values. If the torque difference between two sensors exceeds a torque threshold for a certain amount of time, i.e., asymmetricity dwell time, the processor 312 may generate an error state, and control the motors to enable an active safe hold mode.

The torque threshold and dwell time are configurable parameters stored in the configuration file of memory 314. These and other asymmetricity detection parameters, which may also be stored in the configuration file of memory 314, are tuned or set according to user input, automatic calibration by the control unit 210, or according to one or more identifiers for the surgical instrument 240 or the tool driver 230. The parameters may be tuned such that in a realistically fast motion (e.g., open/close jaw) which creates the largest dynamic torque imbalance using a statistically valid number of instruments, joint asymmetricity is not triggered.

Position symmetricity may also be checked in the same fashion. That is, the processor 312 may determine or identify a position value for two associated actuators or other rotary devices (e.g., from a first position sensor and a second position sensor) and determine the difference between the position values. If the position difference between two sensors exceeds a position threshold for a certain amount of time, i.e., asymmetricity dwell time, the processor 312 may generate an error state and control the motors to enable an active safe hold mode.

The position threshold and dwell time are configurable parameters stored in the configuration file of memory 314. These and other asymmetricity detection parameters, which may also be stored in the configuration file of memory 314, are tuned or set according to user input, automatic calibration by the control unit 210, or according to one or more identifiers for the surgical instrument 240 or the tool driver 230.

In case of breaking or severe wearing of one drive mechanism or disengaging of one closure axis, motor positions become asymmetric so this safety feature is activated. As opposed to overload protection safety mechanism, this safety feature imposes a pass/fail criterion on motion controller. Thus, as soon as asymmetricity is detected, active motion control is halted by the processor 312, motors switch to active safe position hold mode and user receives an alarm on the display (e.g., display unit 319) to remove the instrument. This mode may be considered an unrecoverable error state and/or tool replacement may be recommended.

Herein, the phrase "coupled with" is defined to mean directly connected to or indirectly connected through one or more intermediate components. Such intermediate components may include both hardware- and software-based components. Further, to clarify the use in the pending claims and to hereby provide notice to the public, the phrases "at least one of <A>, <B>, . . . and <N>" or "at least one of <A>, <B>, . . . <N>, or combinations thereof" are defined by the Applicant in the broadest sense, superseding any other implied definitions hereinbefore or hereinafter unless expressly asserted by the Applicant to the contrary, to mean one or more elements selected from the group comprising A, B, . . . and N, that is to say, any combination of one or more of the elements A, B, . . . or N including any one element alone or in combination with one or more of the other elements which may also include, in combination, additional elements not listed.

The disclosed mechanisms may be implemented at any logical and/or physical point(s), or combinations thereof, at which the relevant information/data (e.g., message traffic and responses thereto) may be monitored or flows or is otherwise accessible or measurable, including one or more gateway devices, modems, computers or terminals of one or more market participants, e.g., client computers, etc.

One skilled in the art will appreciate that one or more modules described herein may be implemented using, among other things, a tangible computer-readable medium comprising computer-executable instructions (e.g., executable software code). Alternatively, modules may be implemented as software code, firmware code, specifically configured hardware or processors, and/or a combination of the aforementioned.

The operations of computer devices and systems shown in FIGS. 1-25 may be controlled by computer-executable instructions stored on a non-transitory computer-readable medium. For example, the exemplary computer device or control unit 210 may store computer-executable instructions, generate electronic messages, extracting information from the electronic messages, executing actions relating to the electronic messages, and/or calculating values from the electronic messages to facilitate any of the algorithms or acts described herein. Numerous additional servers, computers, handheld devices, personal digital assistants, telephones and other devices may also be connected to control unit 210.

As illustrated in FIG. 3, the computer system may include a processor 312 implemented by a central processing unit (CPU), a graphics processing unit (GPU), or both. The processor 312 may be a component in a variety of systems. For example, the processor 312 may be part of a standard personal computer or a workstation. The processor 312 may be one or more general processors, digital signal processors, specifically configured processors, application specific integrated circuits, field programmable gate arrays, servers, networks, digital circuits, analog circuits, combinations thereof, or other now known or later developed devices for analyzing and processing data. The processor 312 may implement a software program, such as code generated manually (i.e., programmed).

The computer system includes memory 314 that can communicate via a bus. The memory 314 may be a main memory, a static memory, or a dynamic memory. The memory 314 may include, but is not limited to, computer-readable storage media such as various types of volatile and non-volatile storage media, including but not limited to random-access memory, read-only memory, programmable read-only memory, electrically programmable read-only memory, electrically erasable read-only memory, flash memory, magnetic tape or disk, optical media and the like. In one embodiment, the memory 314 includes a cache or random-access memory for the processor 312. In alternative embodiments, the memory 314 is separate from the processor 312, such as a cache memory of a processor, the system memory, or other memory. The memory 314 may be an external storage device or database for storing data. Examples include a hard drive, compact disk ("CD"), digital video disc ("DVD"), memory card, memory stick, floppy disk, universal serial bus ("USB") memory device, or any other device operative to store data. The memory 314 is operable to store instructions executable by the processor 312. The functions, acts or tasks illustrated in the figures or described herein may be performed by the programmed processor 312 executing the instructions stored in the memory 314. The functions, acts or tasks are independent of the particular type of instructions set, storage media, processor or processing strategy and may be performed by software, hardware, integrated circuits, firmware, microcode and the like, operating alone or in combination. Likewise, processing strategies may include multiprocessing, multitasking, parallel processing and the like.

The computer system may further include a display unit 319, such as a liquid crystal display (LCD), an organic light emitting diode (OLED), a flat panel display, a solid-state display, a cathode ray tube (CRT), a projector, a printer or other now known or later developed display device for outputting determined information. The display 319 may act as an interface for the user to see the functioning of the processor 312, or specifically as an interface with the instructions stored in the memory 314 or elsewhere in the control unit 214.

Additionally, the computer system may include an input device 317 configured to allow a user to interact with any of the components of system. The input device 317 may be a number pad, a keyboard, or a cursor control device, such as a mouse, or a joystick, touch screen display, remote control or any other device operative to interact with the control unit 310.

The present disclosure contemplates a computer-readable medium that includes instructions or receives and executes instructions responsive to a signal, so that a device connected to a network can communicate voice, video, audio, images or any other data over the network. Further, the instructions may be transmitted or received over the network via a communication interface 318. The communication interface 318 may be a part of the processor 312 or may be a separate component. The communication interface 218 may be a physical connection in hardware. The communication interface 318 is configured to connect with a network, external media, the display unit 319, or any other components in the system, or combinations thereof. The connection with the network may be a physical connection, such as a wired Ethernet connection or may be established wirelessly. Likewise, the additional connections with other components of the system may be physical connections or may be established wirelessly.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings and described herein in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the described embodiments should not be understood as requiring such separation in all embodiments, and it should be understood that the described program components and systems can generally be integrated together in a single software product or packaged into multiple software products.

What is claimed is:

1. A surgical robotic system comprising:
   an end effector of a surgical tool coupled to a tool driver;
   an actuator of the tool driver, the actuator configured to drive the end effector; and
   one or more processors configured to:
      receive a position command describing a desired angle for the end effector;
      translate the angle to a command for the actuator with a compensation term,
      wherein the compensation term is based on a source of hysteresis for backlash or compliance; and
      send the command with the compensation term to the actuator.

2. The surgical robotic system of claim 1, the one or more processors configured to:
   access a first polynomial for translating the desired angle to the command when the desired angle corresponds to opening a joint associated with the end effector; and
   access a second polynomial for translating the desired angle to the command when the desired angle corresponds to closing the joint associated with the end effector.

3. The surgical robotic system of claim 2, wherein the first polynomial or the second polynomial includes the compensation term.

4. The surgical robotic system of claim 1, the one or more processors configured to:
   determine whether the desired angle corresponds to a clockwise rotation or a counter-clockwise rotation for a joint associated with the end effector, wherein the compensation term is selected according to the clockwise rotation or the counter-clockwise rotation.

5. The surgical robotic system of claim 1, wherein the compensation term compensates for a plurality of regions in a relationship between the actuator and a measured position for the end effector.

6. The surgical robotic system of claim 5, wherein the plurality of regions includes a compliance region in which a hysteresis or recoil is substantially from compliance, or wherein the plurality of regions includes a backlash region in which the hysteresis or recoil is substantially from backlash.

7. The surgical robotic system of claim 5, wherein the plurality of regions includes a combination region in which a hysteresis or recoil is from backlash and compliance.

8. A surgical robotic system comprising:
   an end effector of a surgical tool coupled to a tool driver;
   an actuator of the tool driver, the actuator configured to drive the end effector; and
   one or more processors configured to:
      receive a position command describing a desired angle for the end effector;
      translate the angle to a command for the actuator with a compensation term; and send the command with the compensation term to the actuator, wherein the compensation term compensates for a plurality of regions in a relationship between the actuator and a measured position for the end effector, wherein the plurality of regions includes a compliance region in which a hysteresis or recoil is substantially from compliance, or wherein the plurality of regions includes a backlash region in which the hysteresis or recoil is substantially from backlash.

9. A surgical robotic system comprising:

an end effector of a surgical tool coupled to a tool driver;

an actuator of the tool driver, the actuator configured to drive the end effector; and one or more processors configured to:
- receive a position command describing a desired angle for the end effector;
- translate the angle to a command for the actuator with a compensation term; and
- send the command with the compensation term to the actuator, wherein the compensation term compensates for a plurality of regions in a relationship between the actuator and a measured position for the end effector, wherein the plurality of regions includes a combination region in which a hysteresis or recoil is from backlash and compliance.

\* \* \* \* \*